US012123011B2

(12) United States Patent
Bowen et al.

(10) Patent No.: US 12,123,011 B2
(45) Date of Patent: *Oct. 22, 2024

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Todd A. Ciche, San Diego, CA (US); Stanislaw Flasinski, Ballwin, MO (US); Arlene R. Howe, Clarkson Valley, MO (US); Jason S. Milligan, Troy, IL (US); James K. Roberts, Chesterfield, MO (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,016

(22) Filed: Oct. 4, 2022

(65) Prior Publication Data

US 2023/0108260 A1 Apr. 6, 2023

Related U.S. Application Data

(62) Division of application No. 16/895,921, filed on Jun. 8, 2020, now Pat. No. 11,492,640, which is a division of application No. 15/846,796, filed on Dec. 19, 2017, now Pat. No. 10,717,989.

(60) Provisional application No. 62/436,736, filed on Dec. 20, 2016.

(51) Int. Cl.
*C12N 15/82* (2006.01)
(52) U.S. Cl.
CPC ................. *C12N 15/8286* (2013.01)
(58) Field of Classification Search
CPC .................................................. C12N 15/8286
See application file for complete search history.

(56) References Cited

U.S. PATENT DOCUMENTS

| | | | |
|---|---|---|---|
| 8,344,207 B2 | 1/2013 | Bogdanova et al. | |
| 8,716,443 B2 | 5/2014 | Druilhe et al. | |
| 10,717,989 B2 * | 7/2020 | Bowen | C07K 14/195 |
| 11,492,640 B2 * | 11/2022 | Bowen | A01N 37/46 |
| 2016/0186204 A1 | 6/2016 | Liu et al. | |

FOREIGN PATENT DOCUMENTS

| | | |
|---|---|---|
| WO | WO 2015/021354 | 2/2015 |
| WO | WO 2015/023846 | 2/2015 |
| WO | 2015114552 | 8/2015 |

OTHER PUBLICATIONS

Friedberg (Automated protein function prediction—the genomic challenge. Brief. Bioinformatics. 7:225-242, 2006) (Year: 2006).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Fourgoux-Nicol et al (Isolation of rapeseed genes expressed early and specifically during development of the male gametophyte. Plant Molecular Biology 40: 857-872, 1999) (Year: 1999).*
Ali et al (Ex Vivo Application of Secreted Metabolites Produced by SoilInhabiting Bacillus spp. Efficiently Controls Foliar Diseases Caused by Alternaria spp. Applied and Environmental Microbiology, 82: 478-490, 2015) (Year: 2015).*
Kiss et al (Complete genome sequence of the filamentous gliding predatory bacterium *Herpetosiphon aurantiacus* type strain (114-95T). Standards in Genomic Sciences. 5:356-370, 2011). (Year: 2011).*
GENBANK Accession No. WP_054772431.1, dated Oct. 15, 2015.
PATRIC fig|759811.5.peg.8510| hypothetical protein [*Lysinibacillus pakistanensis* strain JCM 18776 | 759811.5], available at https://www.bv-brc.org/view/FASTA/dna/?in(feature_id,(PATRIC.759811.5.BBDJ01000053.CDS.7071.7895.rev)), accessed Dec. 15, 2023.
International Search Report and Written Opinion regarding International Application No. PCT/US2017/067019, dated Jun. 6, 2018.
Gill, "What's Good for Whitefly Control on Poinsettias," Greenhouse TPM/IPM Report. Central Maryland Research and Education Center. University of Maryland—Extension—Ellicot City, MD. Jul. 23, 2015.
NCBI GenBank WP_054772431.
*Lysinibacillus pakistanensis* strain JCM 18776, PATRIC database, 2015.
Extended European Search Report regarding European App. No. 17884172.2, dated Sep. 11, 2020.
Fourgoux-Nicol et al. (Plant Molecular Biology 40:857-872, 1999) (Year: 1999).
Ali et al. (Ex Vivo Application of Secreted Metabolites Produced by SoilInhabiting Bacillus spp. Efficiently Controls Foliar Diseases Caused by Alternaria spp. Applied ad Environmental Microbiology, 82:478-490, published online Oct. 2015) (Year: 2015).

* cited by examiner

*Primary Examiner* — Charles Logsdon
*Assistant Examiner* — Wayne Zhong
(74) *Attorney, Agent, or Firm* — Dentons US LLP; David Lanzotti

(57) ABSTRACT

Pesticidal proteins exhibiting toxic activity against Coleopteran, Lepidopteran, Hemipteran, and Thysanopteran pest species are disclosed, and include, but are not limited to, TIC6280, TIC6281, TIC6282, TIC6283, TIC8808, TIC9480, TIC9257, TIC7106, TIC7017, TIC7107, TIC7108, TIC7109, TIC7110, TIC7111, TIC7589, TIC9258, and TIC9259. DNA constructs are provided which contain a recombinant nucleic acid sequence encoding the pesticidal proteins provided. Transgenic plants, plant cells, seed, and plant parts resistant to Lepidopteran, Coleopteran, Hemipteran and Thysanopteran infestation are provided which contain recombinant nucleic acid sequences encoding the disclosed pesticidal proteins. Methods for detecting the presence of the recombinant nucleic acid sequences or the protein of the present invention in a biological sample, and methods of controlling Coleopteran, Lepidopteran, Hemipteran, and Thysanopteran species pests using the disclosed pesticidal proteins are also provided.

26 Claims, 1 Drawing Sheet

Specification includes a Sequence Listing.

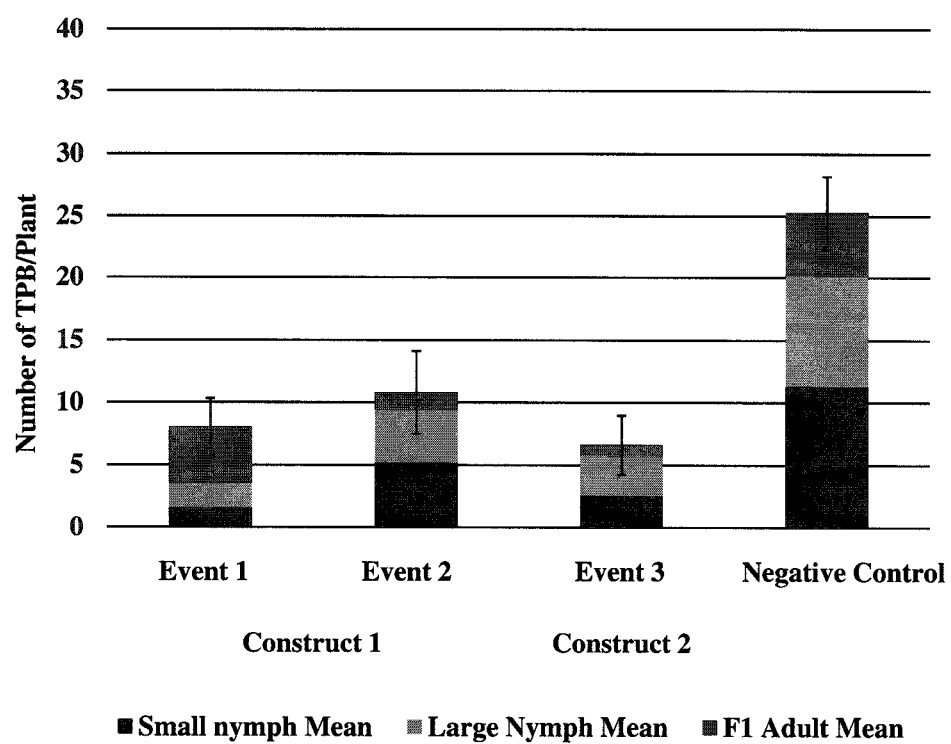

SEQUENCE LISTING

```
Sequence total quantity: 99
SEQ ID NO: 1            moltype = DNA  length = 891
FEATURE                 Location/Qualifiers
misc_feature            1..891
                        note = Nucleic acid sequence obtained from the
                         Lysinibacillus sphaericusspecies AG0067H07 encoding a
                         TIC6280 pesticidal protein with aHistidine tag operably
                         linked to the 3' end, TIC6280-His.
source                  1..891
                        mol_type = other DNA
                        organism = synthetic construct
SEQUENCE: 1
atgtcaaatc aagatttaca gatggaaagc tggttaacat taaatgatgt ttcccttcat  60
caaaatattc aaacaccact ttctttcgac cttacttcct ctttacaaga tgctgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgat  480
gaaatcagta atttatatga tggcatcaca gaaaaagata aagagaaaat taaaaatagt  540
ttacaagctt tagcagaagc tgcttcttca agatcaaatc aagccaatac agaaaatata  600
tttgctcaaa atgttattgt gtgcaatgat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgttcaccac catcacgctc accatcactg a          891

SEQ ID NO: 2            moltype = AA  length = 296
FEATURE                 Location/Qualifiers
REGION                  1..296
                        note = Amino acid sequence of the TIC6280-His protein.
source                  1..296
                        mol_type = protein
                        organism = synthetic construct
SEQUENCE: 2
MSNQDLQMES WLTLNDVSLH QNIQTPLSFD LTSSLQDAAP VQDTISGGLI IGNTQNEAID  60
ANNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAID EISNLYDGIT EKDKEKIKNS  180
LQALAEAASS RSNQANTENI FAQNVIVCND EEIEFCIYSS SVTMLYSGGK NTVRQVDFTL  240
NETHIRFTKE LWSRYSDKVL DKHLALIDDW LLGISTPNSD KTTLACFVHH HHAHHH      296

SEQ ID NO: 3            moltype = DNA  length = 891
FEATURE                 Location/Qualifiers
misc_feature            1..891
                        note = Nucleic acid sequence obtained from the
                         Lysinibacillus sphaericusspecies AG0067H03 encoding a
                         TIC6281 pesticidal protein with aHistidine tag operably
                         linked to the 3' end, TIC6281-His.
source                  1..891
                        mol_type = other DNA
                        organism = synthetic construct
SEQUENCE: 3
atgtcaaatc aagatttaca gatggaaagc tggttaacat taaatgatgt ttcccttcat  60
caaaatattc aaacaccact ttctttcgac cttacttcct ctttacaaga tgctgcacct  120
gtccaagata ctataagtgg aggtttaatt attggtaaca cacaaaacga agctatcgat  180
gccagtaata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgat  480
gaaatcagta atttatatga tggcatcaca gaaaaagata aagagaaaat taaaaatagt  540
ttacaagctt tagcagaagc tgcttcttca agatcaaatc aagccaatac agaaaatata  600
tttgctcaaa atgttattgt gtgcaataat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
```

```
gataaacact tagcgttgat agatgattgg ctacttggaa ttagtactcc taatagtgat  840
aaaactactc tcgcttgctt tgttcaccac catcacgctc accatcactg a           891

SEQ ID NO: 4           moltype = AA  length = 296
FEATURE                Location/Qualifiers
REGION                 1..296
                       note = Amino acid sequence of the TIC6281-His protein.
source                 1..296
                       mol_type = protein
                       organism = synthetic construct
SEQUENCE: 4
MSNQDLQMES WLTLNDVSLH QNIQTPLSFD LTSSLQDAAP VQDTISGGLI IGNTQNEAID  60
ASNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAID EISNLYDGIT EKDKEKIKNS  180
LQALAEAASS RSNQANTENI FAQNVIVCNN EEIEFCIYSS SVTMLYSGGK NTVRQVDFTL  240
NETHIRFTKE LWSRYSDKVL DKHLALIDDW LLGISTPNSD KTTLACFVHH HHAHHH      296

SEQ ID NO: 5           moltype = DNA  length = 891
FEATURE                Location/Qualifiers
misc_feature           1..891
                       note = Nucleic acid sequence obtained from the
                        Lysinibacillus sphaericusspecies AG0069H08 encoding a
                        TIC6282 pesticidal protein with aHistidine tag operably
                        linked to the 3' end, TIC6282-His.
source                 1..891
                       mol_type = other DNA
                       organism = synthetic construct
SEQUENCE: 5
atgtcaaatc aagatttaca gatggaaagc tggttaacag taaatgatgt ttcccttcat  60
caaaatattc aaacaccact ttctttcgac cttacatcct ctttacaaga tgctgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgag  480
gaaatcagta atttatatga tggcatcaca gaaaaagata aagagaaaat taaaaatagt  540
ttacaagctt tagcagaagc tgcctcttca agatcaaatc aagccaatac agaaaatata  600
tttgctcaaa atgttattgt gtgcaatgat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgttcaccac catcacgctc accatcactg a           891

SEQ ID NO: 6           moltype = AA  length = 296
FEATURE                Location/Qualifiers
REGION                 1..296
                       note = Amino acid sequence of the TIC6282-His protein.
source                 1..296
                       mol_type = protein
                       organism = synthetic construct
SEQUENCE: 6
MSNQDLQMES WLTVNDVSLH QNIQTPLSFD LTSSLQDAAP VQDTISGGLI IGNTQNEAID  60
ANNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAIE EISNLYDGIT EKDKEKIKNS  180
LQALAEAASS RSNQANTENI FAQNVIVCND EEIEFCIYSS SVTMLYSGGK NTVRQVDFTL  240
NETHIRFTKE LWSRYSDKVL DKHLALIDDW LLGISTPNSD KTTLACFVHH HHAHHH      296

SEQ ID NO: 7           moltype = DNA  length = 891
FEATURE                Location/Qualifiers
misc_feature           1..891
                       note = Nucleic acid sequence obtained from the
                        Lysinibacillus sphaericusspecies AG0025E04 encoding a
                        TIC6283 pesticidal protein with aHistidine tag operably
                        linked to the 3' end, TIC6283-His
source                 1..891
                       mol_type = other DNA
                       organism = synthetic construct
SEQUENCE: 7
atgtcaaatc aagatttaca gatggaaagc tggttaacag taaatgatgt ttcccttcat  60
caaaatattc aaacaccact ttctttcgac cttacatcct ctttacaaga tgttgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa ttacacaaaa cgaacttcta actggaagac agctattgag  480
gaaatcagta atttatatga tggcatcaca gaaaaagata aagagaaaat taaaaatagt  540
ttacaagctt tagcagaagc tgcctcttca agatcaaatc aagccaatac agaaaatata  600
```

-continued

```
tttgctcaaa atgttattgt gtgcaatgat gaagaaattg aattttgtat ttattcaagt    660
tcagttacaa tgctttatag tggtggtaaa ataccgtaaa gacaggttga tttcactcta    720
aacgaaaccc acattagatt tacaaaagag ttatggagta gatactctga taaagtttta    780
gataaacact tagcgttgat agatgattgg ctacttggaa ttagtactcc taatagtgat    840
aaaactactc tcgcttgctt tgttcaccac catcacgctc accatcactg a             891
```

```
SEQ ID NO: 8            moltype = AA  length = 296
FEATURE                 Location/Qualifiers
REGION                  1..296
                        note = Amino acid sequence of the TIC6283-His protein.
source                  1..296
                        mol_type = protein
                        organism = synthetic construct
SEQUENCE: 8
MSNQDLQMES WLTVNDVSLH QNIQTPLSFD LTSSLQDVAP VQDTISGGLI IGNTQNEAID     60
ANNNVKNALQ TYGRFSNEVK ESAQVSPIVG LTTILDIARI VSNYNPALPT DQENDETKKA    120
RVIAYNQYIT KVLQNPLMHL KSNYEKNYTK RTSNWKTAIE EISNLYDGIT EKDKEKIKNS    180
LQALAEAASS RSNQANTENI FAQNVIVCND EEIEFCIYSS SVTMLYSGGK NTVRQVDFTL    240
NETHIRFTKE LWSRYSDKVL DKHLALIDDW LLGISTPNSD KTTLACFVHH HHAHHH        296
```

```
SEQ ID NO: 9            moltype = DNA  length = 849
FEATURE                 Location/Qualifiers
misc_feature            1..849
                        note = Nucleic acid sequence obtained from the
                        Lysinibacillus sphaericusspecies EGBS0420 encoding a
                        TIC7016 pesticidal protein with aHistidine tag operably
                        linked to the 3' end, TIC7016-His.
source                  1..849
                        mol_type = other DNA
                        organism = synthetic construct
SEQUENCE -continued

```
tggaatgaag caattgacca aattgccaat ttatataatg gcatttcggc agctgacaaa  480
ggaaaaattg tagaaagctt aaaagcatta gcaaaatccg cctcttcttc tagctctgaa  540
aaacaaacgg aaaaactatt tactcaaagt acgattaact gtgaggaaaa tattgatatt  600
tatatttact ctagctctgt cacaatggag gagcacagcg gtaagcataa tgtaaagcag  660
gttgaatttg aaatacaaga aacacaatta agatttacaa aagaattgtg gagtttatac  720
tcagatgctg tgttagctaa acatctagca ttaatggatg attggctgaa tggcattgat  780
acaaaagcag acaaccgttt atccactctt acatgcttag ttcaccacca tcacgctcac  840
catcactga                                                          849

SEQ ID NO: 12          moltype = AA  length = 282
FEATURE                Location/Qualifiers
REGION                 1..282
                       note = Amino acid sequence of the TIC7017-His protein.
source                 1..282
                       mol_type = protein
                       organism = synthetic construct
SEQUENCE: 12
MTNLDLKMES WLALNDISLH QNLEPVAIKL ATSDQTVVSQ GIFVGNQLSE ARIADNQVQQ  60
ALQSFGRYSA AVKEAAKIAP TTGLTTILDI ARIVSNFNPA LPNDKNNVPA YEKYVSKILQ  120
NPLIHLLNSS VKSFKRTTSD WNEAIDQIAN LYNGISAADK GKIVESLKAL AKSASSSSSE  180
KQTEKLFTQS TINCEENIDI YIYSSSVTME EHSGKHNVKQ VEFEIQETQL RFTKELWSLY  240
SDAVLAKHLA LMDDWLNGID TKADNRLSTL TCLVHHHHAH HH                     282

SEQ ID NO: 13          moltype = DNA  length = 849
FEATURE                Location/Qualifiers
misc_feature           1..849
                       note = Nucleic acid sequence obtained from the
                        Lysinibacillus sphaericusspecies AG0025E04 encoding a
                        TIC7107 pesticidal protein with aHistidine tag operably
                        linked to the 3' end, TIC7107-His.
source                 1..849
                       mol_type = other DNA
                       organism = synthetic construct
SEQUENCE: 13
atgacaaatc ttgacttaaa aatggaaagc tggttagcac taaatgatat ttctctgcat  60
caaaatttag agcctgttgc tattaaactt gctccatcag atcaaacagt tgtcagtcaa  120
ggaatctttg ttgggagtca gctgtcggag gctagaatcg ctgacaatca agttcagcaa  180
gcacttcaaa actttggacg ctatagttct gcggtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaaacaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttcaccacca tcacgctcac  840
catcactga                                                          849

SEQ ID NO: 14          moltype = DNA  length = 849
FEATURE                Location/Qualifiers
misc_feature           1..849
                       note = Nucleic acid sequence obtained from the
                        Lysinibacillus sphaericusspecies AG0067H01 encoding a
                        TIC7108 pesticidal protein with aHistidine tag operably
                        linked to the 3' end, TIC7108-His.
source                 1..849
                       mol_type = other DNA
                       organism = synthetic construct
SEQUENCE: 14
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaattg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttcaccacca tcacgctcac  840
catcactga                                                          849

SEQ ID NO: 15          moltype = AA  length = 282
FEATURE                Location/Qualifiers
```

-continued

```
REGION                  1..282
                        note = Amino acid sequence of the TIC7108-His protein.
source                  1..282
                        mol_type = protein
                        organism = synthetic construct
SEQUENCE: 15
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSSE  180
KQIEKLFTQS TINCEENIDI YIYSSSVTME EHNGKHNVKQ VEFEIQETQL RFTKELWSLY  240
SDAVLAKHLA LMDDWLNGID TKADNRLSTL TCLVHHHHAH HH                    282

SEQ ID NO: 16           moltype = DNA  length = 849
FEATURE                 Location/Qualifiers
misc_feature            1..849
                        note = Nucleic acid sequence obtained from the
                         Lysinibacillus sphaericusspecies AG0067H03 encoding a
                         TIC7109 pesticidal protein with aHistidine tag operably
                         linked to the 3' end, TIC7109-His.
source                  1..849
                        mol_type = other DNA
                        organism = synthetic construct
SEQUENCE: 16
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttcaccacca tcacgctcac  840
catcactga                                                         849

SEQ ID NO: 17           moltype = DNA  length = 849
FEATURE                 Location/Qualifiers
misc_feature            1..849
                        note = Nucleic acid sequence obtained from the
                         Lysinibacillus sphaericusspecies AG0067H07 encoding a
                         TIC7110 pesticidal protein with aHistidine tag operably
                         linked to the 3' end, TIC7110-His.
source                  1..849
                        mol_type = other DNA
                        organism = synthetic construct
SEQUENCE: 17
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aactcaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttcaccacca tcacgctcac  840
catcactga                                                         849

SEQ ID NO: 18           moltype = AA  length = 282
FEATURE                 Location/Qualifiers
REGION                  1..282
                        note = Amino acid sequence of the TIC7110-His protein.
source                  1..282
                        mol_type = protein
                        organism = synthetic construct
SEQUENCE: 18
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLVHHHHAH HH                    282
```

```
SEQ ID NO: 19          moltype = DNA  length = 849
FEATURE                Location/Qualifiers
misc_feature           1..849
                       note = Nucleic acid sequence obtained from the
                        Lysinibacillus sphaericusspecies AG0069H08 encoding a
                        TIC7111 pesticidal protein with aHistidine tag operably
                        linked to the 3' end, TIC7111-His.
source                 1..849
                       mol_type = other DNA
                       organism = synthetic construct
SEQUENCE: 19
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttcaccacca tcacgctcac  840
catcactga                                                          849

SEQ ID NO: 20          moltype = DNA  length = 852
FEATURE                Location/Qualifiers
misc_feature           1..852
                       note = Nucleic acid sequence obtained from the
                        Lysinibacillus sphaericusspecies AG0122F12 encoding a
                        TIC7589 pesticidal protein with aHistidine tag operably
                        linked to the 3' end, TIC7589-His.
source                 1..852
                       mol_type = other DNA
                       organism = synthetic construct
SEQUENCE: 20
atgacaaatc ttgatttaaa aatggaaagt tggttggctg taaatgatgt ttctcaccac  60
cagaatcttc aacaaccata ttctgagatt tcatcaacat ctgaagaagt acttgtaagt  120
caaggattat ttgtaggtga taaattggaa aacgcaataa gtgcagatac caatgtccaa  180
caagcacttc aaacatacgg tcgttatagc gacgcagtaa aagaagcaac taaacttgca  240
ccaacaaccg gcttaacaac gttacttgat atttcacgaa ttgtttctgg ctttaatcca  300
gatttaccta atgatcctaa aaatgtccaa gcatacaatc aatacattac aacaatattg  360
aaaaatcctc tttttcattt actaaaatct gaaagagtaa agtttacgag agctacatca  420
gactggaatg aagcaattga taaaattgcg gatctttatg atggtatacc tacatctgat  480
aaaagtaaga ttgtaaaaag cttaaagaca ttagcagaag ccgcctcttc ttataccgaa  540
accaaccaaa cagattattt atttacccaa agtacagtaa attgcagtga caatattgat  600
gtttatattt actcaagtac agtgacattg aaagaaaaaa gtgggaaaca tcacgtaaaa  660
gaatctaccc ttgatatagg ctgcgtacaa ttaagattta caaaagagtt atggagtgta  720
tactctgatg aagtcttaaa aagacattta gcgttgatga ctgattggtt aaatgccatg  780
aattcgaaac caggaactaa acaatcgaaa ctcacttgct tagttcacca ccatcacgct  840
caccatcact ga                                                      852

SEQ ID NO: 21          moltype = AA  length = 283
FEATURE                Location/Qualifiers
REGION                 1..283
                       note = Amino acid sequence of the TIC7589-His protein.
source                 1..283
                       mol_type = protein
                       organism = synthetic construct
SEQUENCE: 21
MTNLDLKMES WLAVNDVSHH QNLQQPYSEI SSTSEEVLVS QGLFVGDKLE NAISADTNVQ  60
QALQTYGRYS DAVKEATKLA PTTGLTTLLD ISRIVSGFNP DLPNDPKNVQ AYNQYITTIL  120
KNPLFHLLKS ERVKFTRATS DWNEAIDKIA DLYDGIPTSD KSKIVKSLKT LAEAASSYTE  180
TNQTDYLFTQ STVNCSDNID VYIYSSTVTL KEKSGKHHVK ESTLDIGCVQ LRFTKELWSV  240
YSDEVLKRHL ALMTDWLNAM NSKPGTKQSK LTCLVHHHHA HHH                    283

SEQ ID NO: 22          moltype = DNA  length = 867
FEATURE                Location/Qualifiers
misc_feature           1..867
                       note = Nucleic acid sequence obtained from the
                        Lysinibacillus sphaericusspecies AG0067H07 encoding a
                        TIC6280 pesticidal protein.
source                 1..867
                       mol_type = genomic DNA
                       organism = Lysinibacillus sphaericus
SEQUENCE: 22
```

-continued

```
atgtcaaatc aagatttaca gatggaaagc tggttaacat taaatgatgt ttcccttcat  60
caaaatattc aaacaccact ttctttcgac cttacttcct ctttacaaga tgctgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgat  480
gaaatcagta atttatatga tggcatcaca gaaaaagata aagagaaaat taaaaatagt  540
ttacaagctt tagcagaagc tgcttcttca agatcaaatc aagccaatac agaaaatata  600
tttgctcaaa atgttattgt gtgcaatgat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgtttaa                                     867

SEQ ID NO: 23          moltype = AA  length = 288
FEATURE                Location/Qualifiers
REGION                 1..288
                       note = MISC_FEATURE - Amino acid sequence of the TIC6280
                        protein.
source                 1..288
                       mol_type = protein
                       organism = Lysinibacillus sphaericus
SEQUENCE: 23
MSNQDLQMES WLTLNDVSLH QNIQTPLSFD LTSSLQDAAP VQDTISGGLI IGNTQNEAID  60
ANNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAID EISNLYDGIT EKDKEKIKNS  180
LQALAEAASS RSNQANTENI FAQNVIVCND EEIEFCIYSS SVTMLYSGGK NTVRQVDFTL  240
NETHIRFTKE LWSRYSDKVL DKHLALIDDW LLGISTPNSD KTTLACFV              288

SEQ ID NO: 24          moltype = DNA  length = 867
FEATURE                Location/Qualifiers
misc_feature           1..867
                       note = Nucleic acid sequence obtained from the
                        Lysinibacillus sphaericusspecies AG0067H03 encoding a
                        TIC6281 pesticidal protein.
source                 1..867
                       mol_type = genomic DNA
                       organism = Lysinibacillus sphaericus
SEQUENCE: 24
atgtcaaatc aagatttaca gatggaaagc tggttaacat taaatgatgt ttcccttcat  60
caaaatattc aaacaccact ttctttcgac cttacttcct ctttacaaga tgctgcacct  120
gtccaagata ctataagtgg aggtttaatt attggtaaca cacaaaacga agctatcgat  180
gccagtaata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgat  480
gaaatcagta atttatatga tggcatcaca gaaaaagata aagagaaaat taaaaatagt  540
ttacaagctt tagcagaagc tgcttcttca agatcaaatc aagccaatac agaaaatata  600
tttgctcaaa atgttattgt gtgcaataat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgtttaa                                     867

SEQ ID NO: 25          moltype = AA  length = 288
FEATURE                Location/Qualifiers
REGION                 1..288
                       note = MISC_FEATURE - Amino acid sequence of the TIC6281
                        protein.
source                 1..288
                       mol_type = protein
                       organism = Lysinibacillus sphaericus
SEQUENCE: 25
MSNQDLQMES WLTLNDVSLH QNIQTPLSFD LTSSLQDAAP VQDTISGGLI IGNTQNEAID  60
ASNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAID EISNLYDGIT EKDKEKIKNS  180
LQALAEAASS RSNQANTENI FAQNVIVCNN EEIEFCIYSS SVTMLYSGGK NTVRQVDFTL  240
NETHIRFTKE LWSRYSDKVL DKHLALIDDW LLGISTPNSD KTTLACFV              288

SEQ ID NO: 26          moltype = DNA  length = 867
FEATURE                Location/Qualifiers
misc_feature           1..867
                       note = Nucleic acid sequence obtained from the
                        Lysinibacillus sphaericusspecies AG0069H08 encoding a
                        TIC6282 pesticidal protein.
source                 1..867
```

-continued

```
                         mol_type = genomic DNA
                         organism = Lysinibacillus sphaericus
SEQUENCE: 26
atgtcaaatc aagatttaca gatggaaagc tggttaacag taaatgatgt ttcccttcat  60
caaaatattc aaacaccact ttctttcgac cttacatcct ctttacaaga tgctgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa atacacaaaa cgaacttcta actggaagac agctattgag  480
gaaatcagta atttatatga tggcatcaca gaaaaagata aagagaaaat taaaaatagt  540
ttacaagctt tagcagaagc tgcctcttca agatcaaatc aagccaatac agaaaatata  600
tttgctcaaa atgttattgt gtgcaatgat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgtttaa                                    867

SEQ ID NO: 27            moltype = AA  length = 288
FEATURE                  Location/Qualifiers
REGION                   1..288
                         note = MISC_FEATURE - Amino acid sequence of the TIC6282
                          protein.
source                   1..288
                         mol_type = protein
                         organism = Lysinibacillus sphaericus
SEQUENCE: 27
MSNQDLQMES WLTVNDVSLH QNIQTPLSFD LTSSLQDAAP VQDTISGGLI IGNTQNEAID  60
ANNNVKNALQ TYGRFSNEVK ESAQVSPIVG LTTILDIARI VSNYNPALPT DQENDETKKA  120
RVIAYNQYIT KVLQNPLMHL KSNYEKKYTK RTSNWKTAIE EISNLYDGIT EKDKEKIKNS  180
LQALAEAASS RSNQANTENI FAQNVIVCND EEIEFCIYSS SVTMLYSGGK NTVRQVDFTL  240
NETHIRFTKE LWSRYSDKVL DKHLALIDDW LLGISTPNSD KTTLACFV              288

SEQ ID NO: 28            moltype = DNA  length = 867
FEATURE                  Location/Qualifiers
misc_feature             1..867
                         note = Nucleic acid sequence obtained from the
                          Lysinibacillus sphaericusspecies AG0025E04 encoding a
                          TIC6283 pesticidal protein.
source                   1..867
                         mol_type = genomic DNA
                         organism = Lysinibacillus sphaericus
SEQUENCE: 28
atgtcaaatc aagatttaca gatggaaagc tggttaacag taaatgatgt ttcccttcat  60
caaaatattc aaacaccact ttctttcgac cttacatcct ctttacaaga tgttgcacct  120
gtccaagata ctataagtgg aggtttaatt attggtaaca cacaaaacga agctatcgat  180
gccaataata atgtaaaaaa tgcactgcaa acatacggtc gttttagtaa tgaggtcaaa  240
gaatctgctc aagtaagtcc gattgttgga ttaacaacta tacttgatat tgcaagaata  300
gtttccaatt acaacccggc tttgcccact gatcaagaaa atgatgaaac taaaaaagca  360
agagttattg catacaacca atatattacg aaggtgttgc aaaatccttt aatgcactta  420
aaaagcaact atgaaaaaaa ttacacaaaa cgaacttcta actggaagac agctattgag  480
gaaatcagta atttatatga tggcatcaca gaaaaagata aagagaaaat taaaaatagt  540
ttacaagctt tagcagaagc tgcctcttca agatcaaatc aagccaatac agaaaatata  600
tttgctcaaa atgttattgt gtgcaatgat gaagaaattg aattttgtat ttattcaagt  660
tcagttacaa tgctttatag tggtggtaaa aataccgtaa gacaggttga tttcactcta  720
aacgaaaccc acattagatt tacaaaagag ttatggagta gatactctga taaagtttta  780
gataaacact tagcgttgat agatgattgg ctacttggaa ttagtactcc taatagtgat  840
aaaactactc tcgcttgctt tgtttaa                                    867

SEQ ID NO: 29            moltype = AA  length = 288
FEATURE                  Location/Qualifiers
REGION                   1..288
                         note = MISC_FEATURE - Amino acid sequence of the TIC6283
                          protein.
source                   1..288
                         mol_type = protein
                         organism = Lysinibacillus sphaericus
SEQUENCE: 29
MSNQDLQMES WLTVNDVSLH QNIQTPLSFD LTSSLQDVAP VQDTISGGLI IGNTQNEAID  60
ANNNVKNALQ TYGRFSNEVK ESAQVSPIVG LTTILDIARI VSNYNPALPT DQENDETKKA  120
RVIAYNQYIT KVLQNPLMHL KSNYEKNYTK RTSNWKTAIE EISNLYDGIT EKDKEKIKNS  180
LQALAEAASS RSNQANTENI FAQNVIVCND EEIEFCIYSS SVTMLYSGGK NTVRQVDFTL  240
NETHIRFTKE LWSRYSDKVL DKHLALIDDW LLGISTPNSD KTTLACFV              288

SEQ ID NO: 30            moltype = DNA  length = 825
FEATURE                  Location/Qualifiers
misc_feature             1..825
                         note = Nucleic acid sequence obtained from the
```

```
                         Lysinibacillus sphaericusspecies EGBS0420 encoding a
                         TIC7016 pesticidal protein.
source                  1..825
                        mol_type = genomic DNA
                        organism = Lysinibacillus sphaericus
SEQUENCE: 30
atgacaaatc ttgacttaaa aatggaaagt tggttagcac taaatgatat ttctctacat  60
caaaatttag agcctgttgc tattaaactc gcaacatcag atcaaacagt tgtcagtcaa  120
ggaatctttg tagggaatca gttgtcggag gctagaattg ctgacaatca ggttcagcag  180
gcacttcaaa gctttggacg ctatagtact gctgtaaaag aagctgctaa agtagctcca  240
acaactggtt taacaactat ccttgacatt gctagaatcg tttctaattt caatccggca  300
ttaccaaacg ataaaaataa tgtacctgcc tatgaaaaat atgtttcaaa aatattacaa  360
aacccactta tccatttatt aaatagcagt gtaaaatcct tcaaacgtac gacttctgat  420
tggaatgaag caattgacca aattgccaat ttatataatg gcatttcggc agctgacaaa  480
ggaaaaattg tagaaagctt aaaagcatta gcaaaatccg cctcctcttc tagctctgaa  540
aaacaaacgg aaaaactatt tactcaaagt acgattaact gtgaggaaaa tatagatatt  600
tatatttact ctagctctgt cacaatggag gagcacaacg gtaagcacaa tgtaaagcag  660
gttgaatttg aaatacaaga aacacaatta agatttacaa aagaattgtg gagtttatac  720
tctgatgctg tgttagctaa acatctagct ctaatggatg attggctaaa tggcattgat  780
acaaaagcag acaatcgttt atccactctt acatgcttag tttaa                 825

SEQ ID NO: 31           moltype = AA  length = 274
FEATURE                 Location/Qualifiers
REGION                  1..274
                        note = MISC_FEATURE - Amino acid sequence of the TIC7016
                         protein.
source                  1..274
                        mol_type = protein
                        organism = Lysinibacillus sphaericus
SEQUENCE: 31
MTNLDLKMES WLALNDISLH QNLEPVAIKL ATSDQTVVSQ GIFVGNQLSE ARIADNQVQQ  60
ALQSFGRYST AVKEAAKVAP TTGLTTILDI ARIVSNFNPA LPNDKNNVPA YEKYVSKILQ  120
NPLIHLLNSS VKSFKRTTSD WNEAIDQIAN LYNGISAADK GKIVESLKAL AKSASSSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLV                             274

SEQ ID NO: 32           moltype = DNA  length = 825
FEATURE                 Location/Qualifiers
misc_feature            1..825
                        note = Nucleic acid sequence obtained from the
                         Lysinibacillus sphaericusspecies EGBS1094 encoding a
                         TIC7017 pesticidal protein.
source                  1..825
                        mol_type = genomic DNA
                        organism = Lysinibacillus sphaericus
SEQUENCE: 32
atgacaaatc ttgacttaaa aatggaaagt tggttagcac taaatgatat ttctctacat  60
caaaatttag agcctgttgc tattaaactc gcaacatcag atcaaacagt tgtcagtcaa  120
ggaatctttg ttgggaatca gctgtcggag gctagaattg ctgacaacca agttcagcaa  180
gcacttcaaa gctttggacg ctatagtgct gctgtaaaag aagctgctaa aatagctcca  240
acaactggat taacaactat ccttgacatt gctagaattg tttctaattt caatcctgca  300
ttaccaaacg ataaaaataa tgtacctgcc tatgaaaaat atgtttcaaa aatattacaa  360
aacccactta tccatttatt aaatagcagt gtaaaatcct ttaaacgtac gacttccgat  420
tggaatgaag caattgacca aattgccaat ttatataatg gcatttcggc agctgacaaa  480
ggaaaaattg tagaaagctt aaaagcatta gcaaaatccg cctcttcttc tagctctgaa  540
aaacaaacgg aaaaactatt tactcaaagt acgattaact gtgaggaaaa tattgatatt  600
tatatttact ctagctctgt cacaatggag gagcacagcg gtaagcataa tgtaaagcag  660
gttgaatttg aaatacaaga aacacaatta agatttacaa aagaattgtg gagtttatac  720
tcagatgctg tgttagctaa acatctagca ttaatggatg attggctgaa tggcattgat  780
acaaaagcag acaaccgttt atccactctt acatgcttag tttaa                 825

SEQ ID NO: 33           moltype = AA  length = 274
FEATURE                 Location/Qualifiers
REGION                  1..274
                        note = MISC_FEATURE - Amino acid sequence of the TIC7017
                         protein.
source                  1..274
                        mol_type = protein
                        organism = Lysinibacillus sphaericus
SEQUENCE: 33
MTNLDLKMES WLALNDISLH QNLEPVAIKL ATSDQTVVSQ GIFVGNQLSE ARIADNQVQQ  60
ALQSFGRYSA AVKEAAKIAP TTGLTTILDI ARIVSNFNPA LPNDKNNVPA YEKYVSKILQ  120
NPLIHLLNSS VKSFKRTTSD WNEAIDQIAN LYNGISAADK GKIVESLKAL AKSASSSSSE  180
KQTEKLFTQS TINCEENIDI YIYSSSVTME EHSGKHNVKQ VEFEIQETQL RFTKELWSLY  240
SDAVLAKHLA LMDDWLNGID TKADNRLSTL TCLV                             274

SEQ ID NO: 34           moltype = DNA  length = 825
FEATURE                 Location/Qualifiers
misc_feature            1..825
```

-continued

```
                      note = Nucleic acid sequence obtained from the
                       Lysinibacillus sphaericusspecies AG0025E04 encoding a
                       TIC7107 pesticidal protein.
source                1..825
                      mol_type = genomic DNA
                      organism = Lysinibacillus sphaericus
SEQUENCE: 34
atgacaaatc ttgacttaaa aatggaaagc tggttagcac taaatgatat ttctctgcat  60
caaaatttag agcctgttgc tattaaactt gctccatcag atcaaacagt tgtcagtcaa  120
ggaatctttg ttgggagtca gctgtcggag gctagaatcg ctgacaatca agttcagcaa  180
gcacttcaaa actttggacg ctatagttct gcggtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaaacaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag tttag                 825

SEQ ID NO: 35         moltype = DNA  length = 825
FEATURE               Location/Qualifiers
misc_feature          1..825
                      note = Nucleic acid sequence obtained from the
                       Lysinibacillus sphaericusspecies AG0067H01 encoding a
                       TIC7108 pesticidal protein.
source                1..825
                      mol_type = genomic DNA
                      organism = Lysinibacillus sphaericus
SEQUENCE: 35
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaattg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag tttag                 825

SEQ ID NO: 36         moltype = AA  length = 274
FEATURE               Location/Qualifiers
REGION                1..274
                      note = MISC_FEATURE - Amino acid sequence of the TIC7108
                       protein.
source                1..274
                      mol_type = protein
                      organism = Lysinibacillus sphaericus
SEQUENCE: 36
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSSE  180
KQIEKLFTQS TINCEENIDI YIYSSSVTME EHNGKHNVKQ VEFEIQETQL RFTKELWSLY  240
SDAVLAKHLA LMDDWLNGID TKADNRLSTL TCLV                             274

SEQ ID NO: 37         moltype = DNA  length = 825
FEATURE               Location/Qualifiers
misc_feature          1..825
                      note = Nucleic acid sequence obtained from the
                       Lysinibacillus sphaericusspecies AG0067H03 encoding a
                       TIC7109 pesticidal protein.
source                1..825
                      mol_type = genomic DNA
                      organism = Lysinibacillus sphaericus
SEQUENCE: 37
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
```

```
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag tttag                825

SEQ ID NO: 38           moltype = DNA  length = 825
FEATURE                 Location/Qualifiers
misc_feature            1..825
                        note = Nucleic acid sequence obtained from the
                         Lysinibacillus sphaericusspecies AG0067H07 encoding a
                         TIC7110 pesticidal protein.
source                  1..825
                        mol_type = genomic DNA
                        organism = Lysinibacillus sphaericus
SEQUENCE: 38
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aactcaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag tttag                825

SEQ ID NO: 39           moltype = AA  length = 274
FEATURE                 Location/Qualifiers
REGION                  1..274
                        note = MISC_FEATURE - Amino acid sequence of the TIC7110
                         protein.
source                  1..274
                        mol_type = protein
                        organism = Lysinibacillus sphaericus
SEQUENCE: 39
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLV                            274

SEQ ID NO: 40           moltype = DNA  length = 825
FEATURE                 Location/Qualifiers
misc_feature            1..825
                        note = Nucleic acid sequence obtained from the
                         Lysinibacillus sphaericusspecies AG0069H08 encoding a
                         TIC7111 pesticidal protein.
source                  1..825
                        mol_type = genomic DNA
                        organism = Lysinibacillus sphaericus
SEQUENCE: 40
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag tttag                825

SEQ ID NO: 41           moltype = DNA  length = 828
FEATURE                 Location/Qualifiers
misc_feature            1..828
                        note = Nucleic acid sequence obtained from the
                         Lysinibacillus sphaericusspecies AG0122F12 encoding a
                         TIC7589 pesticidal protein.
```

```
source                  1..828
                        mol_type = genomic DNA
                        organism = Lysinibacillus sphaericus
SEQUENCE: 41
atgacaaatc ttgatttaaa aatggaaagt tggttggctg taaatgatgt ttctcaccac -continued

```
agcgtgacca tgctctacag cggcggcaag aacaccgtac gacaagtgga tttcacgctg  720
aacgagactc acatccggtt cacgaaggaa ctctggtcgc gctacagcga caaggtgctg  780
gacaagcact tggcgctcat cgacgactgg ctgctgggca tcagcacgcc caatagtgac  840
aagacgaccc tcgcgtgctt cgtgtga                                      867
```

```
SEQ ID NO: 45           moltype = DNA  length = 867
FEATURE                 Location/Qualifiers
misc_feature            1..867
                        note = Synthetic coding sequence encoding a TIC6283
                         pesticidal proteindesigned for expression in a plant cell.
source                  1..867
                        mol_type = other DNA
                        organism = synthetic construct
SEQUENCE: 45
atgtcgaacc aggatctcca gatggagtcg tggcttacgg tgaatgatgt gtcgctgcac  60
cagaacatac aaacgccgct cagcttcgac ctcacgtcgt ccctccagga cgtggctccc  120
gtgcaagaca cgattagcgg cgggctcatc atcggcaaca cgcagaacga ggcgatagac  180
gccaacaaca acgtcaagaa cgccctccag acctacggcc ggttcagcaa cgaggtgaag  240
gagtcggccc aagtctcgcc catcgtcggc ctcacgacta tcctggacat cgcccgtatc  300
gtctcgaact acaacccggc gctcccgacc gaccaggaga acgacgagac caagaaggcc  360
cgcgtgatcg cgtacaacca gtacatcacc aaggtgctcc agaacccgct gatgcacctc  420
aagtcgaact acgagaagaa ctacactaag cggacttcca actggaagac cgccatcgag  480
gaaatctcga acctgtacga cggcatcacc gagaaggaca aggagaagat aaagaacagc  540
ctccaggccc tcgcggaggc ggcctcgtcc cgctccaacc aggctaatac cgagaacatc  600
ttcgcccaga acgtcattgt gtgtaacgac gaggagattg agttctgcat ctacagcagc  660
agcgtgacca tgctgtactc aggcgggaag aatacggtgc gccaagtgga cttcacgctg  720
aacgagaccc acatccgctt caccaaggag ctgtggtccc gatactccga caaggtgctc  780
gacaagcacc tcgcgctcat cgacgactgg ctgctgggca tctccacgcc gaacagcgac  840
aagaccacgc tcgcctgctt cgtgtag                                      867
```

```
SEQ ID NO: 46           moltype = DNA  length = 828
FEATURE                 Location/Qualifiers
misc_feature            1..828
                        note = Synthetic coding sequence encoding a TIC7016PL
                         pesticidal proteindesigned for expression in a plant cell,
                         wherein an additionalcodon encoding an alanine residue is
                         inserted immediatelyfollowing the initiating methionine
                         codon.
source                  1..828
                        mol_type = other DNA
                        organism = synthetic construct
SEQUENCE: 46
atggctacaa acctcgacct caagatggag agctggctgg cgctcaacga catcagtctc  60
caccagaacc tcgagccggt cgctatcaaa ctcgctacct ccgaccaaac cgtggtgtcc  120
cagggcatct tcgtcggcaa ccagctcagc gaggcccgga tcgccgacaa ccaggtccaa  180
caggccctgc agagtttcgg gcggtacagc acggcagtca aagaggccgc gaaggtggct  240
ccgaccaccg ggctgactac catcctggac atcgcgcgga tcgtctcgaa cttcaatccg  300
gctctgccga acgacaagaa caacgttccc gcctacgaga agtacgtttc gaagatcctg  360
cagaacccac tgatacacct gctcaattcg tccgtgaagt ctttcaagcg cactacgtcg  420
gactggaacg aagcgatcga ccagatcgcc aacctgtaca acggcatcag tgccgcggac  480
aagggcaaga tcgtcgagag cctcaaggcc ctcgcaaagt cggcctccag ctctagcagc  540
gagaaacaga ccgagaagct cttcacccag agcaccatca actgcgagga gaacatcgac  600
atctacatct actcctcgtc cgtgacaatg gaggagcaca acggcaagca caatgtgaag  660
caagtggagt tcgagatcca ggagacgcag ctccgcttca ccaaggagct ctggagcctc  720
tactctgacg cagtgttggc aaagcacctc gctttgatgg acgactggct taacgggatc  780
gacactaaag cggacaacag actgagcacc ctcacctgcc tggtctga               828
```

```
SEQ ID NO: 47           moltype = AA  length = 275
FEATURE                 Location/Qualifiers
REGION                  1..275
                        note = Amino acid sequence of TIC7016PL, wherein an
                         additional alanineresidue is inserted immediately
                         following the initiatingmethionine.
source                  1..275
                        mol_type = protein
                        organism = synthetic construct
SEQUENCE: 47
MATNLDLKME SWLALNDISL HQNLEPVAIK LATSDQTVVS QGIFVGNQLS EARIADNQVQ  60
QALQSFGRYS TAVKEAAKVA PTTGLTTILD IARIVSNFNP ALPNDKNNVP AYEKYVSKIL  120
QNPLIHLLNS SVKSFKRTTS DWNEAIDQIA NLYNGISAAD KGKIVESLKA LAKSASSSSS  180
EKQTEKLFTQ STINCEENID IYIYSSSVTM EEHNGKHNVK QVEFEIQETQ LRFTKELWSL  240
YSDAVLAKHL ALMDDWLNGI DTKADNRLST LTCLV                             275
```

```
SEQ ID NO: 48           moltype = DNA  length = 828
FEATURE                 Location/Qualifiers
misc_feature            1..828
                        note = Synthetic coding sequence encoding a TIC7017PL
                         pesticidal proteindesigned for expression in a plant cell,
                         wherein an additionalcodon encoding an alanine residue is
```

```
                       inserted immediatelyfollowing the initiating methionine
                       codon.
        source         1..828
                       mol_type = other DNA
                       organism = synthetic construct
SEQUENCE: 48
atggctacga acctggatct caagatggag tcatggctgg cgctcaacga catcagcctg    60
caccagaatc tcgagccggt tgccatcaag ctggccacct ccgaccagac ggtcgtgtcc   120
cagggcatct ttgtgggcaa ccagctgtcc gaggcgcgga tagcggacaa ccaggtccag   180
caagcgctgc aatccttcgg tcgatacagc gccgccgtga aggaggcagc caagatcgca   240
ccaacaaccg gcctcaccac gatactggac attgcccgca ttgtctccaa tttcaacccg   300
gcccttccga cgacaagaa caacgtgccg gcatacgaga agtacgtctc caaaatctta    360
cagaatcctc tcatccacct cctgaatagc agcgtcaaga gtttcaagcg caccacgagt   420
gactggaacg aggcgatcga ccagatcgcg aacttaca atggaatcag cgccgccgac    480
aagggcaaga tcgtggagag tctcaaggcg ctggcgaagt ccgcctccag cagttccagc   540
gagaagcaga cggagaagct gttcacccag agcaccatca actgcgagga gaacatcgac   600
atctacatct acagcagctc ggtcacgatg gaggagcact cagggaagca aacgtcaag    660
caagtgggag tcgagatcca ggagacccag ctccgcttca caaggaact gtggagcctt   720
tactccgacg ccgtcctggc aaagcacctc gcgctcatgg acgactggct gaacggcatc   780
gacaccaagg cggacaaccg gctgagcacc ctaacctgcc tcgtctga              828

SEQ ID NO: 49          moltype = AA    length = 275
FEATURE                Location/Qualifiers
REGION                 1..275
                       note = Amino acid sequence of TIC7017PL, wherein an
                       additional alanineresidue is inserted immediately
                       following the initiatingmethionine.
        source         1..275
                       mol_type = protein
                       organism = synthetic construct
SEQUENCE: 49
MATNLDLKME SWLALNDISL HQNLEPVAIK LATSDQTVVS QGIFVGNQLS EARIADNQVQ    60
QALQSFGRYS AAVKEAAKIA PTTGLTTILD IARIVSNFNP ALPNDKNNVP AYEKYVSKIL   120
QNPLIHLLNS SVKSFKRTTS DWNEAIDQIA NLYNGISAAD KGKIVESLKA LAKSASSSSS   180
EKQTEKLFTQ STINCEENID IYIYSSSVTM EEHSGKHNVK QVEFEIQETQ LRFTKELWSL   240
YSDAVLAKHL ALMDDWLNGI DTKADNRLST LTCLV                              275

SEQ ID NO: 50          moltype = DNA    length = 828
FEATURE                Location/Qualifiers
misc_feature           1..828
                       note = Synthetic coding sequence encoding a TIC7108PL
                       pesticidal proteindesigned for expression in a plant cell,
                       wherein an additionalcodon encoding an alanine residue is
                       inserted immediatelyfollowing the initiating methionine
                       codon.
        source         1..828
                       mol_type = other DNA
                       organism = synthetic construct
SEQUENCE: 50
atggctacca acctcgacct taagatggag tcgtggttgg cgctgaacga catctccctc    60
catcagaatc tcgagccagt ggccatcaag ctggcgccct ccgaccagac tgtcgtgtcc   120
cagggcatct tcgtgggctc ccaactgagc gaggcgcgga tcgccgacaa ccaggtgcag   180
caagcgctgc agaacttcgg ccgctacagc tccgctgtga aggaggccgc caaggtcgct   240
cctaccaccg gcctcaccac tattctcgac attgccagaa tcgtctccaa cttcaacccg   300
gcgctcccga cgacaagaa caacgtcccg gcctacgaga agtacgtctc gaagattctt   360
cagaacccgc tcatccacct cctgaacagc agcctcaagt cattcaagcg ccgcaccagc   420
gactggaacg aggtcatcga ccagattgcg aaccctaca acggcatcag cgcagtggat   480
aagggcaaga tcgtcgagtc cctcaaggcc ctggcgaaca gtgcctcttc cagctcttcc   540
gagaagcaga tcgagaagct ctttacccaa agcacgatta actgcgagga gaacatcgac   600
atctacatct actcatcatc cgtgacgatg gaggagcaca atggccaagca caacgtgaag   660
caagtgggag tcgagatcca ggagacccag ctccggttca ccaaggagct atggtccctc   720
tactcggacg cggtcctcgc caaacacctg gcgctcatgg acgactggct gaatggaata   780
gacactaagg cggacaaccg gctctccacg ctcacgtgcc tcgtctga               828

SEQ ID NO: 51          moltype = AA    length = 275
FEATURE                Location/Qualifiers
REGION                 1..275
                       note = Amino acid sequence of TIC7108PL, wherein an
                       additional alanineresidue is inserted immediately
                       following the initiatingmethionine.
        source         1..275
                       mol_type = protein
                       organism = synthetic construct
SEQUENCE: 51
MATNLDLKME SWLALNDISL HQNLEPVAIK LAPSDQTVVS QGIFVGSQLS EARIADNQVQ    60
QALQNFGRYS SAVKEAAKVA PTTGLTTILD IARIVSNFNP ALPNDKNNVP AYEKYVSKIL   120
QNPLIHLLNS SLKSFKRRTS DWNEVIDQIA NLYNGISAVD KGKIVESLKA LANSASSSSS   180
EKQIEKLFTQ STINCEENID IYIYSSSVTM EEHNGKHNVK QVEFEIQETQ LRFTKELWSL   240
YSDAVLAKHL ALMDDWLNGI DTKADNRLST LTCLV                              275
```

```
SEQ ID NO: 52           moltype = DNA  length = 828
FEATURE                 Location/Qualifiers
misc_feature            1..828
                        note = Synthetic coding sequence encoding a TIC7110PL
                         pesticidal proteindesigned for expression in a plant cell,
                         wherein an additionalcodon encoding an alanine residue is
                         inserted immediatelyfollowing the initiating methionine
                         codon.
source                  1..828
                        mol_type = other DNA
                        organism = synthetic construct
SEQUENCE: 52
atggctacca acctcgacct caagatggag tcctggctcg cgctgaatga catctcgctg    60
caccagaatc tggagcccgt cgccatcaag ctcgcgccca gcgaccagac agttgtttcc  120
cagggcatct tcgtgggcag ccagctcagc gaagcgcgta tcgccgacaa ccaggtgcag  180
caagccctgc agaacttcgg gcggtactcc agcgcggtga aggaggcggc gaaggtcgct  240
ccgactacag ggctcacaac cattctcgac atcgcgcgca tcgtctcgaa cttcaacccg  300
gctctcccga acgacaagaa caacgtcccg gcttacgaga agtacgtcag caagatcctc  360
cagaacccgc tgatccactt actcaattct agcctcaaat cctttaaacg acggacctcc  420
gattggaaca aggtgatcga ccagattgcg aaccttacaa cggcatctc tgccgttgac  480
aagggcaaga tcgtcgagtc actcaaagcg ctggcgagta gcgccagctc ctcatcttct  540
gagaagcaga ctgagaagct ctttacccag tccacgatca actgcgagga gaacatcgac  600
atctacatct actccagcag cgtcacgatg gaggagcaca tggcaagcaa acgtgaag   660
caagtggagt tcgagatcca ggagacccag ctccggttca ctaaggagct ttggtcgctc  720
tactcggacg ccgtgctggc gaagcacctg gcgctgatgg acgactggct gaacgggata  780
gacacgaagg ccgacaaccg cctgagtacc ttgacctgct ggtctga                828

SEQ ID NO: 53           moltype = AA  length = 275
FEATURE                 Location/Qualifiers
REGION                  1..275
                        note = Amino acid sequence of TIC7110PL, wherein an
                         additional alanineresidue is inserted immediately
                         following the initiatingmethionine.
source                  1..275
                        mol_type = protein
                        organism = synthetic construct
SEQUENCE: 53
MATNLDLKME SWLALNDISL HQNLEPVAIK LAPSDQTVVS QGIFVGSQLS EARIADNQVQ    60
QALQNFGRYS SAVKEAAKVA PTTGLTTILD IARIVSNFNP ALPNDKNNVP AYEKYVSKIL  120
QNPLIHLLNS SLKSFKRRTS DWNEVIDQIA NLYNGISAVD KGKIVESLKA LANSASSSSS  180
EKQTEKLFTQ STINCEENID IYIYSSSVTM EEHNGKHNVK QVEFEIQETQ LRFTKELWSL  240
YSDAVLAKHL ALMDDWLNGI DTKADNRLST LTCLV                              275

SEQ ID NO: 54           moltype = DNA  length = 1689
FEATURE                 Location/Qualifiers
misc_feature            1..1689
                        note = Synthetic sequence encoding a TIC7110/TIC6280 fusion
                         toxinprotein, TIC7110-TIC6280F1, wherein the two toxin
                         proteinencoding sequences are contiguous and in frame.
source                  1..1689
                        mol_type = other DNA
                        organism = synthetic construct
SEQUENCE: 54
atgacaaatc ttgacttaaa aatggaaagc tggttagcac taaatgatat ttctctgcat    60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg gaagcataa tgtaaagcaa  660
gttgaatttg aaatacaaga aactcaatta agatttacaa agaattgtg gagtttatac  720
tcagatgctg tgttagcaaa acatctagct ttaatggatg attggctcaa tggcattgat  780
acaaaagctg acaatcgttt atccactctt acatgcttag ttatgtcaaa tcaagattta  840
cagatggaaa gctggttaac attaaatgat gtttccttc atcaaaatat tcaaacacca  900
ctttctttcg accttacttc ctctttacaa gatgctgcac ctgtccaaga tactataagt  960
ggaggtttaa ttattggtaa cacacaaaac gaagctatcg atgccaataa taatgtaaaa 1020
aatgcactgc aaacatacgg tcgttttagt aatgaggtca agaatctgc tcaagtaagt 1080
ccgattgttg gattaacaac tatacttgat attgcaagaa tagtttccaa ttacaacccg 1140
gctttgccca ctgatcaaga aaatgatgaa actaaaaag caagattat tgcatacaac 1200
caatatatta cgaaggtgtt gcaaatcct ttaatgcact aaaaagcaa ctatgaaaaa 1260
aaatacacaa aacgaacttc taactggaag acagctattg atgaaatcag taatttatat 1320
gatggcatca cagaaaaaga taaagagaaa attaaaaata gttacagc tttagcagaa 1380
gctgcttctt caagatcaaa tcaagccaat acagaaaata tatttgctca aatgttatt 1440
gtgtgcaatg atgaagaaat tgaatttgt atttattcaa gttcagttac aatgcttat 1500
```

```
agtggtggta aaaataccgt aagacaggtt gatttcactc taaacgaaac ccacattaga   1560
tttacaaaag agttatggag tagatactct gataaagttt tagataaaca cttagcgttg   1620
atagatgatt ggctacttgg aattagtact cctaatagtg ataaaactac tctcgcttgc   1680
tttgtttaa                                                           1689

SEQ ID NO: 55           moltype = AA   length = 562
FEATURE                 Location/Qualifiers
REGION                  1..562
                        note = Amino acid sequence of a TIC7110/TIC6280 fusion
                         toxin protein,TIC7110-TIC6280F1, wherein the two toxin
                         protein amino acidsequences are contiguous.
source                  1..562
                        mol_type = protein
                        organism = synthetic construct
SEQUENCE: 55
MTNLDLKMES WLALNDISLH QNLEPVAIKL APSDQTVVSQ GIFVGSQLSE ARIADNQVQQ    60
ALQNFGRYSS AVKEAAKVAP TTGLTTILDI ARIVSNFNPA LPNDKNNVPA YEKYVSKILQ   120
NPLIHLLNSS LKSFKRRTSD WNEVIDQIAN LYNGISAVDK GKIVESLKAL ANSASSSSE    180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLVMSNQDL QMESWLTLND VSLHQNIQTP   300
LSFDLTSSLQ DAAPVQDTIS GGLIIGNTQN EAIDANNNVK NALQTYGRFS NEVKESAQVS   360
PIVGLTTILD IARIVSNYNP ALPTDQENDE TKKARVIAYN QYITKVLQNP LMHLKSNYEK   420
KYTKRTSNWK TAIDEISNLY DGITEKDKEK IKNSLQALAE AASSRSNQAN TENIFAQNVI   480
VCNDEEIEFC IYSSSVTMLY SGGKNTVRQV DFTLNETHIR FTKELWSRYS DKVLDKHLAL   540
IDDWLLGIST PNSDKTTLAC FV                                            562

SEQ ID NO: 56           moltype = DNA   length = 1707
FEATURE                 Location/Qualifiers
misc_feature            1..1707
                        note = Synthetic sequence encoding a TIC7110/TIC6280 fusion
                         toxinprotein, TIC7110-TIC6280F2, wherein a cleavable
                         linker sequence(Linker 1) is operably linked and in frame
                         between the two toxinprotein encoding sequences.
source                  1..1707
                        mol_type = other DNA
                        organism = synthetic construct
SEQUENCE: 56
atgacaaatc ttgacttaaa aatggaaagc tggttagcac taaatgatat ttctctgcat    60
caaaatttag agcctgttgc tattaaactt gcaccatcag atcaaacagt tgtcagtcaa   120
ggaatctttg ttgggagtca gctgtcggag gctagaatcg ctgacaatca agttcagcaa   180
gcacttcaaa actttggacg ctatagttct gcagtaaaag aagctgctaa agtagctcca   240
acaactggat taacaactat tcttgatatt gctagaattg tttctaattt taatccagca   300
ttaccaaacg ataaaaataa tgttcctgct tatgaaaaat atgtgtcaaa aattttacaa   360
aacccactta tccatttatt aaatagcagt ctaaaatcct ttaaacgtag gacttccgat   420
tggaatgaag taattgacca aatcgccaat ttatataatg gcatttcggc agttgataaa   480
ggaaaaatcg tagaaagctt aaaagcatta gcaaattccg cctcttcttc tagctcagaa   540
aaacaaactg aaaaactatt tactcaaagc acgattaact gtgaggaaaa tattgatatt   600
tatatttact ctagctctgt tacaatggag gagcacaatg gaagcataa tgtaaagcaa    660
gttgaatttg aaatacaaga aactcaatta agatttacaa aagaattgtg gagtttatac   720
tcagatgctg tgttagcaaa acatctagct ttaatggatg attggctcaa tggcattgat   780
acaaaagcta caatcgtttt atccactctt acatgcttag ttggtagtgg cggtgcttca   840
atgtcaaatc aagatttaca gatggaaagc tggttaacat taaatgatgt tccccttcat   900
caaaatattc aaacaccact ttctttcgac cttacttcct ctttacaaga tgctgcacct   960
gtccaagata ctataagtgg aggtttaatt attggtaaca cacaaaacga agctatcgat  1020
gccaataata atgtaaaaaa tgcactgcaa acatacggtc gttttagtaa tgaggtcaaa  1080
gaatctgctc aagtaagtcc gattgttgga ttaacaacta tacttgatat tgcaagaata  1140
gtttccaatt acaacccggc tttgcccact gatcaagaaa atgatgaaac taaaaaagca  1200
agagttattg catacaacca atatattacg aaggtgttgc aaaatccttt aatgcactta  1260
aaaagcaact atgaaaaaaa atacacaaaa cgaacttcta actggaagac agctattgat  1320
gaaatcagta atttatatga tggcatcaca gaaaaagata agagaaaat taaaaatagt  1380
ttacaagctt tagcagaagc tgcttcttca agatcaaatc aagccaatac agaaaatata  1440
tttgctcaaa atgttattgt gtgcaatgat gaagaaattg aatttgtat ttattcaagt  1500
tcagttacaa tgctttatag tggtggtaaa aataccgtaa gacaggttga tttcactcta  1560
aacgaaaccc acattagatt tacaaaagag ttatggagta gatactctga taaagtttta  1620
gataaacact tagcgttgat agatgattgg ctacttggaa ttagtactcc taatagtgat  1680
aaaactactc tcgcttgctt tgtttaa                                       1707

SEQ ID NO: 57           moltype = AA   length = 568
FEATURE                 Location/Qualifiers
REGION                  1..568
                        note = Amino acid sequence of a TIC7110/TIC6280 fusion
                         toxin protein,TIC7110-TIC6280F2,wherein a cleavable lin

```
ALQNFGRYSS AVKEAAKVAP TTGLTTILDI ARIVSNFNPA LPNDKNNVPA YEKYVSKILQ   120
NPLIHLLNSS LKSFKRRTSD WNEVIDQIAN LYNGISAVDK GKIVESLKAL ANSASSSSSE   180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLVGSGGAS MSNQDLQMES WLTLNDVSLH   300
QNIQTPLSFD LTSSLQDAAP VQDTISGGLI IGNTQNEAID ANNNVKNALQ TYGRFSNEVK   360
ESAQVSPIVG LTTILDIARI VSNYNPALPT DQENDETKKA RVIAYNQYIT KVLQNPLMHL   420
KSNYEKKYTK RTSNWKTAID EISNLYDGIT EKDKEKIKNS LQALAEAASS RSNQANTENI   480
FAQNVIVCND EEIEFCIYSS SVTMLYSGGK NTVRQVDFTL NETHIRFTKE LWSRYSDKVL   540
DKHLALIDDW LLGISTPNSD KTTLACFV                                     568

SEQ ID NO: 58           moltype = DNA  length = 1728
FEATURE                 Location/Qualifiers
misc_feature            1..1728
                        note = Synthetic sequence encoding a TIC7110/TIC6280 fusion
                         toxinprotein, TIC7110-TIC6280F3, wherein a flexible linker
                         sequence(Linker 2) is operably linked and in frame between
                         the two toxinprotein encoding sequences.
source                  1..1728
                        mol_type = other DNA
                        organism = synthetic construct
SEQUENCE: 58
atgacaaatc ttgacttaaa aatggaaagc tggttagcac taaatgatat ttctctgcat    60
caaaatttag agcctgttgc tattaaactt gcaccatcag atcaaacagt tgtcagtcaa   120
ggaatctttg ttgggagtca gctgtcggag gctagaatcg ctgacaatca agttcagcaa   180
gcacttcaaa actttggacg ctatagttct gcagtaaaag aagctgctaa agtagctcca   240
acaactggat taacaactat tcttgatatt gctagaattg tttctaattt taatccagca   300
ttaccaaacg ataaaaataa tgttcctgct tatgaaaaat atgtgtcaaa attttttacaa   360
aacccactta tccatttatt aaatagcagt ctaaaatcct ttaaacgtag gacttccgat   420
tggaatgaag taattgacca aatcgccaat ttatataatg gcatttcggc agttgataaa   480
ggaaaaatcg tagaaagctt aaaagcatta gcaaattccg cctcttcttc tagctcagaa   540
aaacaaactg aaaaactatt tactcaaagc acgattaact gtgaggaaaa tattgatatt   600
tatatttact ctagctctgt tacaatggag gagcacaatg gaagcataa tgtaaagcaa   660
gttgaatttg aaatacaaga aactcaatta agatttacaa agaattgtg gagtttatac   720
tcagatgctg tgttagcaaa acatctagct ttaatggatg attggctcaa tggcattgat   780
acaaaagctg acaatcgttt atccactctt acatgcttag ttggaagcgg aacacatcaa   840
tctggtaaga catcgggatc tatgtcaaat caagatttac agatggaaag ctggttaaca   900
ttaaatgatg tttcccttca tcaaaatatt caaacaccac tttctttcga ccttacttcc   960
tctttacaag atgctgcacc tgtccaagat actataagtg gaggtttaat tattggtaac  1020
acacaaaacg aagctatcga tgccaataat aatgtaaaaa atgcactgca aacatacgat  1080
cgttttagta atgaggtcaa agaatctgct caagtaagtc cgattgttgg attaacaact  1140
atacttgata ttgcaagaat agtttccaat tacaacccgg ctttgcccac tgatcaagaa  1200
aatgatgaaa ctaaaaaagc aagagttatt gcatacaacc aatatattac gaaggtgttg  1260
caaaatcctt taatgcactt aaaaagcaac tatgaaaaaa aatacacaaa acgaacttct  1320
aactggaaga cagctattga tgaaatcagt aatttatatg atggcatcac agaaaaagat  1380
aaaagagaaa ttaaaaatag tttacaagct ttagcagaag ctgcttcttc aagatcaaat  1440
caagccaata cagaaaatat atttgctcaa aatgttattg tgtgcaatga tgaagaaatt  1500
gaatttgta tttattcaag ttcagttaca atgcttttag ttggtggtaa aaataccgta  1560
agacaggttg atttcactct aaacgaaacc cacattagat ttacaaaaga gttatggagt  1620
agatactctg ataaagtttt agataaacac ttagcgttga tagatgattg gctacttgga  1680
attagtactc ctaatagtga taaaactact ctcgcttgct tgtttaa               1728

SEQ ID NO: 59           moltype = AA  length = 575
FEATURE                 Location/Qualifiers
REGION                  1..575
                        note = Amino acid sequence of a TIC7110/TIC6280 fusion
                         toxin protein,TIC7110-TIC6280F3,wherein a flexible linker
                         peptide sequence(Linker 2) is inserted between the two
                         toxin protein amino acidsequences.
source                  1..575
                        mol_type = protein
                        organism = synthetic construct
SEQUENCE: 59
MTNLDLKMES WLALNDISLH QNLEPVAIKL APSDQTVVSQ GIFVGSQLSE ARIADNQVQQ    60
ALQNFGRYSS AVKEAAKVAP TTGLTTILDI ARIVSNFNPA LPNDKNNVPA YEKYVSKILQ   120
NPLIHLLNSS LKSFKRRTSD WNEVIDQIAN LYNGISAVDK GKIVESLKAL ANSASSSSSE   180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLVGSGTHQ SGKTSGSMSN QDLQMESWLT   300
LNDVSLHQNI QTPLSFDLTS SLQDAAPVQD TISGGLIIGN TQNEAIDANN NVKNALQTYG   360
RFSNEVKESA QVSPIVGLTT ILDIARIVSN YNPALPTDQE NDETKKARVI AYNQYITKVL   420
QNPLMHLKSN YEKKYTKRTS NWKTAIDEIS NLYDGITEKD KEKIKNSLQA LAEAASSRSN   480
QANTENIFAQ NVIVCNDEEI EFCIYSSSVT MLYSGGKNTV RQVDFTLNET HIRFTKELWS   540
RYSDKVLDKH LALIDDWLLG ISTPNSDKTT LACFV                              575

SEQ ID NO: 60           moltype = DNA  length = 1689
FEATURE                 Location/Qualifiers
misc_feature            1..1689
                        note = Synthetic sequence encoding a TIC7111/TIC6282 fusion
                         toxinprotein, TIC7111-TIC6282F1, wherein the two toxin
                         proteinencoding sequences are contiguous and in frame.
```

```
source                      1..1689
                            mol_type = other DNA
                            organism = synthetic construct
SEQUENCE: 60
atgacaaatc ttgacttaaa aatggaaagc tggttagcac taaatgatat ttctctgcat    60
caaaatttag agcctgttgc tattaaactt gcaccatcag atcaaacagt tgtcagtcaa   120
ggaatctttg ttgggagtca gctgtcggag gctagaatcg ctgacaatca agttcagcaa   180
gcacttcaaa actttggacg ctatagttct gcagtaaaag aagctgctaa agtagctcca   240
acaactggat taacaactat tcttgacatt gctagaattg tctctaattt taatccagca   300
ttaccaaacg ataaaaataa tgttcctgct tatgaaaaat atgtgtcaaa aattttacaa   360
aacccactta tccatttatt aaatagcagt ctaaaatcct ttaaacgtag gacttccgat   420
tggaatgaag taattgacca aatcgccaat ttatataatg gcatttcggc agttgataaa   480
ggaaaaatcg tagaaagctt aaaagcatta gcaaattccg cctcttcttc tagctcagaa   540
aaacaaactg aaaaactatt tactcaaagc acgattaact gtgaggaaaa tattgatatt   600
tatatttact ctagctctgt tacaatggag gagcacaatg gaagcataa tgtaaagcaa    660
gttgaatttg aaatacaaga aacacaatta agatttacaa agaattgtg gagtttatac    720
tcagatgctg tgttagcaaa acatctagct ttaatggatg attggctcaa tggcattgat    780
acaaaagctg acaatcgttt atccactctt acatgcttag ttatgtcaaa tcaagattta    840
cagatggaaa gctggttaac agtaaatgat gtttcccttc atcaaaatat tcaaacacca    900
ctttctttcg accttacatc ctctttacaa gatgctgcac ctgtccaaga tactataagt    960
ggaggtttaa ttattggtaa cacacaaac gaagctatcg atgccaataa taatgtaaaa   1020
aatgcactgc aaacatacgg tcgttttagt aatgaggtca agaatctgc tcaagtaagt   1080
ccgattgttg gattaacaac tatacttgat attgcaagaa tagttccaa ttacaaccg    1140
gctttgccca ctgatcaaga aaatgatgaa actaaaaaag caagagttat tgcatacaac   1200
caatatatta cgaaggtgtt gcaaaatcct ttaatgcact aaaaagcaa ctatgaaaaa    1260
aaatacacaa aacgaacttc taactggaag acagctattg aggaaatcag taatttatt    1320
gatggcatca cagaaaaaga taaagagaaa attaaaaata gtttacaagc tttagcagaa   1380
gctgcctctt caagatcaaa tcaagccaat acagaaaata tatttgctca aaatgttatt   1440
gtgtgcaatg atgaagaaat tgaattttgt atttattcaa gttcagttac aatgcttat     1500
agtggtggta aaaataccgt aagacaggtt gatttcactc taaacgaaac ccacattaga   1560
tttacaaaag agttatggag tagatactct gataaagttt tagataaca cttagcgttg   1620
atagatgatt ggctacttgg aattagtact cctaatagtg ataaaactac tctcgcttgc   1680
tttgtttaa                                                            1689

SEQ ID NO: 61            moltype = AA    length = 562
FEATURE                  Location/Qualifiers
REGION                   1..562
                         note = Amino acid sequence of a TIC7111/TIC6282 fusion
                         toxin protein.
source                   1..562
                         mol_type = protein
                         organism = synthetic construct
SEQUENCE: 61
MTNLDLKMES WLALNDISLH QNLEPVAIKL APSDQTVVSQ GIFVGSQLSE ARIADNQVQQ    60
ALQNFGRYSS AVKEAAKVAP TTGLTTILDI ARIVSNFNPA LPNDKNNVPA YEKYVSKILQ   120
NPLIHLLNSS LKSFKRRTSD WNEVIDQIAN LYNGISAVDK GKIVESLKAL ANSASSSSSE   180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLVMSNQDL QMESWLTVND VSLHQNIQTP   300
LSFDLTSSLQ DAAPVQDTIS GGLIIGNTQN EAIDANNNVK NALQTYGRFS NEVKESAQVS   360
PIVGLTTILD IARIVSNYNP ALPTDQENDE TKKARVIAYN QYITKVLQNP LMHLKSNYEK   420
KYTKRTSNWK TAIEEISNLY DGITEKDKEK IKNSLQALAE AASSRSNQAN TENIFAQNVI   480
VCNDEEIEFC IYSSSVTMLY SGGKNTVRQV DFTLNETHIR FTKELWSRYS DKVLDKHLAL   540
IDDWLLGIST PNSDKTTLAC FV                                            562

SEQ ID NO: 62            moltype = DNA    length = 1707
FEATURE                  Location/Qualifiers
misc_feature             1..1707
                         note = Synthetic sequence encoding a TIC7111/TIC6282 fusion
                         toxinprotein, TIC7111-TIC6282F2, wherein a cleavable
                         linker sequence(Linker 1) is operably linked and in frame
                         between the two toxinprotein encoding sequences.
source                   1..1707
                         mol_type = other DNA
                         organism = synthetic construct
SEQUENCE: 62
atgacaaatc ttgacttaaa aatggaaagc tggttagcac taaatgatat ttctctgcat    60
caaaatttag agcctgttgc tattaaactt gcaccatcag atcaaacagt tgtcagtcaa   120
ggaatctttg ttgggagtca gctgtcggag gctagaatcg ctgacaatca agttcagcaa   180
gcacttcaaa actttggacg ctatagttct gcagtaaaag aagctgctaa agtagctcca   240
acaactggat taacaactat tcttgacatt gctagaattg tctctaattt taatccagca   300
ttaccaaacg ataaaaataa tgttcctgct tatgaaaaat atgtgtcaaa aattttacaa   360
aacccactta tccatttatt aaatagcagt ctaaaatcct ttaaacgtag gacttccgat   420
tggaatgaag taattgacca aatcgccaat ttatataatg gcatttcggc agttgataaa   480
ggaaaaatcg tagaaagctt aaaagcatta gcaaattccg cctcttcttc tagctcagaa   540
aaacaaactg aaaaactatt tactcaaagc acgattaact gtgaggaaaa tattgatatt   600
tatatttact ctagctctgt tacaatggag gagcacaatg gaagcataa tgtaaagcaa    660
gttgaatttg aaatacaaga aacacaatta agatttacaa agaattgtg gagtttatac    720
tcagatgctg tgttagcaaa acatctagct ttaatggatg attggctcaa tggcattgat    780
acaaaagctg acaatcgttt atccactctt acatgcttag ttggtagtgg cggtgcttca    840
```

-continued

```
atgtcaaatc aagatttaca gatggaaagc tggttaacag taaatgatgt ttcccttcat  900
caaaatattc aaacaccact ttctttcgac cttacatcct ctttacaaga tgctgcacct  960
gtccaagata ctataagtgg aggtttaatt attggtaaca cacaaaacga agctatcgat  1020
gccaataata atgtaaaaaa tgcactgcaa acatacggtc gttttagtaa tgaggtcaaa  1080
gaatctgctc aagtaagtcc gattgttgga ttaacaacta tacttgatat tgcaagaata  1140
gtttccaatt acaacccggc tttgcccact gatcaagaaa atgatgaaac taaaaaagca  1200
agagttattg catacaacca atatattacg aaggtgttgc aaaatccttt aatgcactta  1260
aaaagcaact atgaaaaaaa atacacaaaa cgaacttcta actggaagac agctattgag  1320
gaaatcagta atttatatga tggcatcaca gaaaaagata aagagaaaat taaaaatagt  1380
ttacaagctt tagcagaagc tgcctcttca agatcaaatc aagccaatac agaaaatata  1440
tttgctcaaa atgttattgt gtgcaatgat gaagaaattg aattttgtat ttattcaagt  1500
tcagttacaa tgctttatag tggtggtaaa aataccgtaa gacaggttga tttcactcta  1560
aacgaaaccc acattagatt tacaaaagag ttatggagta gatactctga taaagtttta  1620
gataaacact tagcgttgat agatgattgg ctacttggaa ttagtactcc taatagtgat  1680
aaaactactc tcgcttgctt tgtttaa                                    1707
```

```
SEQ ID NO: 63          moltype = AA  length = 568
FEATURE                Location/Qualifiers
REGION                 1..568
                       note = Amino acid sequence of a TIC7111/TIC6282 fusion
                        toxin protein,TIC7111-TIC6282F2,wherein a cleavable linker
                        peptide sequence(Linker 1) is inserted between the two
                        toxin protein amino acidsequences.
source                 1..568
                       mol_type = protein
                       organism = synthetic construct
SEQUENCE: 63
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLVGSGGAS MSNQDLQMES WLTVNDVSLH  300
QNIQTPLSFD LTSSLQDAAP VQDTISGGLI IGNTQNEAID ANNNVKNALQ TYGRFSNEVK  360
ESAQVSPIVG LTTILDIARI VSNYNPALPT DQENDETKKA RVIAYNQYIT KVLQNPLMHL  420
KSNYEKKYTK RTSNWKTAIE EISNLYDGIT EKDKEKIKNS LQALAEAASS RSNQANTENI  480
FAQNVIVCND EEIEFCIYSS SVTMLYSGGK NTVRQVDFTL NETHIRFTKE LWSRYSDKVL  540
DKHLALIDDW LLGISTPNSD KTTLACFV                                   568
```

```
SEQ ID NO: 64          moltype = DNA  length = 1728
FEATURE                Location/Qualifiers
misc_feature           1..1728
                       note = Synthetic sequence encoding a TIC7111/TIC6282 fusion
                        toxinprotein, TIC7111-TIC6282F3, wherein a flexible linker
                        sequence(Linker 2) is operably linked and in frame between
                        the two toxinprotein encoding sequences.
source                 1..1728
                       mol_type = other DNA
                       organism = synthetic construct
SEQUENCE: 64
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttggaagcgg aacacatcaa  840
tctggtaaga catcgggatc tatgtcaaat caagatttac agatggaaag ctggttaaca  900
gtaaatgatg tttcccttca tcaaaatatt caaacaccac tttctttcga ccttacatcc  960
tctttacaag atgctgcacc tgtccaagat actataagtg gaggtttaat tattggtaac  1020
acacaaaacg aagctatcga tgccaataat aatgtaaaaa atgcactgca aacatacggt  1080
cgttttagta atgaggtcaa agaatctgct caagtaagtc cgattgttgg attaacaact  1140
atacttgata ttgcaagaat agtttccaat tacaacccgg ctttgcccac tgatcaagaa  1200
aatgatgaaa ctaaaaaagc aagagttatt gcatacaacc aatatattac gaaggtgttg  1260
caaaatcctt taatgcactt aaaaagcaac tatgaaaaaa aatacacaaa acgaacttct  1320
aactggaaga cagctattga ggaaatcagt aatttatatg atggcatcac agaaaaagat  1380
aaagagaaaa ttaaaaatag tttacaagct ttagcagaag ctgcctcttc aagatcaaat  1440
caagccaata cagaaaatat atttgctcaa aatgttattg tgtgcaatga tgaagaaatt  1500
gaattttgta tttattcaag ttcagttaca atgctttata gtggtggtaa aaataccgta  1560
agacaggttg atttcactct aaacgaaacc cacattagat ttacaaaaga gttatggagt  1620
agatactctg ataaagtttt agataaacac ttagcgttga tagatgattg gctacttgga  1680
attagtactc ctaatagtga taaaactact ctcgcttgct ttgtttaa             1728
```

```
SEQ ID NO: 65           moltype = AA  length = 575
FEATURE                 Location/Qualifiers
REGION                  1..575
                        note = Amino acid sequence of a TIC7111/TIC6282 fusion
                         toxin protein,TIC7111-TIC6282F3,wherein a flexible linker
                         peptide sequence(Linker 2) is inserted between the two
                         toxin protein amino acidsequences.
source                  1..575
                        mol_type = protein
                        organism = synthetic construct
SEQUENCE: 65
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLVGSGTHQ SGKTSGSMSN QDLQMESWLT  300
VNDVSLHQNI QTPLSFDLTS SLQDAAPVQD TISGGLIIGN TQNEAIDANN NVKNALQTYG  360
RFSNEVKESA QVSPIVGLTT ILDIARIVSN YNPALPTDQE NDETKKARVI AYNQYITKVL  420
QNPLMHLKSN YEKKYTKRTS NWKTAIEEIS NLYDGITEKD KEKIKNSLQA LAEAASSRSN  480
QANTENIFAQ NVIVCNDEEI EFCIYSSSVT MLYSGGKNTV RQVDFTLNET HIRFTKELWS  540
RYSDKVLDKH LALIDDWLLG ISTPNSDKTT LACFV                          575

SEQ ID NO: 66           moltype = DNA  length = 1689
FEATURE                 Location/Qualifiers
misc_feature            1..1689
                        note = Synthetic sequence encoding a TIC7109/TIC6281 fusion
                         toxinprotein, TIC7109-TIC6281F1, wherein the two toxin
                         proteinencoding sequences are contiguous and in frame.
source                  1..1689
                        mol_type = other DNA
                        organism = synthetic construct
SEQUENCE: 66
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttatgtcaaa tcaagattta  840
cagatggaaa gctggttaac attaaatgat gtttcccttc atcaaaatat tcaaacacca  900
ctttctttcg accttacttc ctctttacaa gatgctgcac ctgtccaaga tactataagt  960
ggaggtttaa ttattggtaa cacacaaaac gaagctatcg atgccagtaa taatgtaaaa  1020
aatgcactgc aaacatacgg tcgttttagt aatgaggtca aagaatctgc tcaagtaagt  1080
ccgattgttg gattaacaac tatacttgat attgcaagaa tagtttccaa ttacaacccg  1140
gctttgccca ctgatcaaga aaatgatgaa actaaaaaag caagagttat tgcatacaac  1200
caatatatta cgaaggtgtt gcaaaatcct ttaatgcact taaaaagcaa ctatgaaaaa  1260
aaatacacaa aacgaacttc taactggaag acagctattg atgaaatcag taatttatat  1320
gatggcatca cagaaaaaga taaagagaaa attaaaaata gtttacaagc tttagcagaa  1380
gctgcttctt caagatcaaa tcaagccaat acagaaaata tatttgctca aaatgttatt  1440
gtgtgcaata atgaagaaat tgaattttgt atttattcaa gttcagttac aatgctttat  1500
agtggtggta aaaataccgt aagacaggtt gatttcactc taaacgaaac ccacattaga  1560
tttacaaaag agttatggag tagatactct gataaagttt tagataaaca cttagcgttg  1620
atagatgatt ggctacttgg aattagtact cctaatagtg ataaaactac tctcgcttgc  1680
tttgtttaa                                                        1689

SEQ ID NO: 67           moltype = AA  length = 562
FEATURE                 Location/Qualifiers
REGION                  1..562
                        note = Amino acid sequence of a TIC7109/TIC6281 fusion
                         toxin protein,TIC7109-TIC6281F1, wherein the two toxin
                         protein amino acidsequences are contiguous.
source                  1..562
                        mol_type = protein
                        organism = synthetic construct
SEQUENCE: 67
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLVMSNQDL QMESWLTLND VSLHQNIQTP  300
LSFDLTSSLQ DAAPVQDTIS GGLIIGNTQN EAIDASNNVK NALQTYGRFS NEVKESAQVS  360
PIVGLTTILD IARIVSNYNP ALPTDQENDE TKKARVIAYN QYITKVLQNP LMHLKSNYEK  420
```

```
KYTKRTSNWK TAIDEISNLY DGITEKDKEK IKNSLQALAE AASSRSNQAN TENIFAQNVI    480
VCNNEEIEFC IYSSSVTMLY SGGKNTVRQV DFTLNETHIR FTKELWSRYS DKVLDKHLAL    540
IDDWLLGIST PNSDKTTLAC FV                                            562

SEQ ID NO: 68           moltype = DNA   length = 1707
FEATURE                 Location/Qualifiers
misc_feature            1..1707
                        note = Synthetic sequence encoding a TIC7109/TIC6281 fusion
                        toxinprotein, TIC7109-TIC6281F2, wherein a cleavable
                        linker sequence(Linker 1) is operably linked and in frame
                        between the two toxinprotein encoding sequences.
source                  1..1707
                        mol_type = other DNA
                        organism = synthetic construct
SEQUENCE: 68
atgacaaatc ttgacttaaa aatggaaagc tggttagcac taaatgatat ttctctgcat    60
caaaatttag agcctgttgc tattaaactt gcaccatcag atcaaacagt tgtcagtcaa    120
ggaatctttg ttgggagtca gctgtcggag gctagaatcg ctgacaatca agttcagcaa    180
gcacttcaaa actttggacg ctatagttct gcagtaaaag aagctgctaa agtagctcca    240
acaactggat taacaactat tcttgatatt gctagaattg tttctaattt taatccagca    300
ttaccaaacg ataaaaataa tgttcctgct tatgaaaaat atgtgtcaaa aattttacaa    360
aacccactta tccatttatt aaatagcagt ctaaaatcct ttaaacgtag gacttccgat    420
tggaatgaag taattgacca aatcgccaat ttatataatg gcatttcggc agttgataaa    480
ggaaaaatcg tagaaagctt aaaagcatta gcaaattccg cctcttcttc tagctcagaa    540
aaacaaactg aaaaactatt tactcaaagc acgattaact gtgaggaaaa tattgatatt    600
tatatttact ctagctctgt tacaatggag gagcacataa ggaagcataa tgtaaagcaa    660
gttgaatttg aaatacaaga aacacaatta agatttacaa aagaattgtg gagtttatac    720
tcagatgctg tgttagcaaa acatctagct ttaatggatg attggctcaa tggcattgat    780
acaaaagctg acaatcgttt atccactctt acatgcttag ttggtagtgg cggtgcttca    840
atgtcaaatc aagatttaca gatggaaagc tggttaacat taaatgatgt ttcccttcat    900
caaaatattc aaacaccact ttctttcgac cttacttcct ctttacaaga tgctgcacct    960
gtccaagata ctataagtgg aggtttaatt attggtaaca cacaaaacga agctatcgat    1020
gccagtaata atgtaaaaaa tgcactgcaa acatacggtc gttttagtaa tgaggtcaaa    1080
gaatctgctc aagtaagtcc gattgttgga ttaacaacta tacttgatat tgcaagaata    1140
gtttccaatt acaacccggc tttgcccact gatcaagaaa atgatgaaac taaaaaagca    1200
agagttattg catacaacca atatattacg aaggtgttgc aaaatccttt aatgcactta    1260
aaaagcaact atgaaaaaaa atacacaaaa cgaacttcta actggaagac agctattgat    1320
gaaatcagta atttatatga tggcatcaca gaaaaagata aagagaaaat taaaaatagt    1380
ttacaagctt tagcagaagc tgcttcttca agatcaaatc agccaatac agaaaatata    1440
tttgctcaaa atgttattgt gtgcaataat gaagaaattg aattttgtat ttattcaagt    1500
tcagttacaa tgctttatag tggtggtaaa ataccgtaa gacaggttga tttcactcta    1560
aacgaaaccc acattagatt tacaaaagag ttatggagta gatactctga taagttttta    1620
gataaacact tagcgttgat agatgattgg ctacttggaa ttagtactcc aatagtgat    1680
aaaactactc tcgcttgctt tgtttaa                                       1707

SEQ ID NO: 69           moltype = AA   length = 568
FEATURE                 Location/Qualifiers
REGION                  1..568
                        note = Amino acid sequence of a TIC7109/TIC6281 fusion
                        toxin protein,TIC7109-TIC6281F2,wherein a cleavable linker
                        peptide sequence(Linker 1) is inserted between the two
                        toxin protein amino acidsequences.
source                  1..568
                        mol_type = protein
                        organism = synthetic construct
SEQUENCE: 69
MTNLDLKMES WLALNDISLH QNLEPVAIKL APSDQTVVSQ GIFVGSQLSE ARIADNQVQQ    60
ALQNFGRYSS AVKEAAKVAP TTGLTTILDI ARIVSNFNPA LPNDKNNVPA YEKYVSKILQ    120
NPLIHLLNSS LKSFKRRTSD WNEVIDQIAN LYNGISAVDK GKIVESLKAL ANSASSSSE    180
KQTEKLFTQS TINCEENIDI YIYSSSVTME EHNGKHNVKQ VEFEIQETQL RFTKELWSLY    240
SDAVLAKHLA LMDDWLNGID TKADNRLSTL TCLVGSGGAS MSNQDLQMES WLTLNDVSLH    300
QNIQTPLSFD LTSSLQDAAP VQDTISGGLI IGNTQNEAID ASNNVKNALQ TYGRFSNEVK    360
ESAQVSPIVG LTTILDIARI VSNYNPALPT DQENDETKKA RVIAYNQYIT KVLQNPLMHL    420
KSNYEKKYTK RTSNWKTAID EISNLYDGIT EKDKEKIKNS LQALAEAASS RSNQANTENI    480
FAQNVIVCNN EEIEFCIYSS SVTMLYSGGK NTVRQVDFTL NETHIRFTKE LWSRYSDKVL    540
DKHLALIDDW LLGISTPNSD KTTLACFV                                      568

SEQ ID NO: 70           moltype = DNA   length = 1728
FEATURE                 Location/Qualifiers
misc_feature            1..1728
                        note = Synthetic sequence encoding a TIC7109/TIC6281 fusion
                        toxinprotein, TIC7109-TIC6281F3, wherein a flexible linker
                        sequence(Linker 2) is operably linked and in frame between
                        the two toxinprotein encoding sequences.
source                  1..1728
                        mol_type = other DNA
                        organism = synthetic construct
SEQUENCE: 70
atgacaaatc ttgacttaaa aatggaaagc tggttagcac taaatgatat ttctctgcat    60
```

```
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg ggaagcataa tgtaaagcaa  660
gttgaatttg aaatacaaga aacacaatta agatttacaa aagaattgtg gagtttatac  720
tcagatgctg tgttagcaaa acatctagct ttaatggatg attggctcaa tggcattgat  780
acaaaagctg acaatcgttt atccactctt acatgcttag ttggaagcgg aacacatcaa  840
tctggtaaga catcgggatc tatgtcaaat caagatttac agatggaaag ctggttaaca  900
ttaaatgatg tttcccttca tcaaaatatt caaacaccac tttctttcga ccttacttcc  960
tctttacaag atgctgcacc tgtccaagat actataagtg gaggtttaat tattggtaac  1020
acacaaaacg aagctatcga tgccagtaat aatgtaaaaa atgcactgca aacatacggt  1080
cgttttagta atgaggtcaa agaatctgct caagtaagtc cgattgttgg attaacaact  1140
atacttgata ttgcaagaat agtttccaat tacaacccgg ctttgcccac tgatcaagaa  1200
aatgatgaaa ctaaaaaagc aagagttatt gcatacaacc aatatattac gaaggtgttg  1260
caaaatcctt taatgcactt aaaaagcaac tatgaaaaaa aatacacaaa acgaacttct  1320
aactggaaga cagctattga tgaaatcagt aatttatatg atggcatcac agaaaaagat  1380
aaagagaaaa ttaaaaatag tttacaagct ttagcagaag ctgcttcttc aagatcaaat  1440
caagccaata cagaaaatat atttgctcaa aatgttattg tgtgcaataa tgaagaaatt  1500
gaattttgta tttattcaag ttcagttaca atgctttata gtggtggtaa aaataccgta  1560
agacaggttg atttcactct aaacgaaacc cacattagat ttacaaaaga gttatggagt  1620
agatactctg ataaagtttt agataaacac ttagcgttga tagatgattg gctacttgga  1680
attagtactc ctaatagtga taaaactact ctcgcttgct ttgtttaa              1728
```

```
SEQ ID NO: 71          moltype = AA  length = 575
FEATURE                Location/Qualifiers
REGION                 1..575
                       note = Amino acid sequence of a TIC7109/TIC6281 fusion
                        toxin protein,TIC7109-TIC6281F3,wherein a flexible linker
                        peptide sequence(Linker 2) is inserted between the two
                        toxin protein amino acidsequences.
source                 1..575
                       mol_type = protein
                       organism = synthetic construct
SEQUENCE: 71
MTNLDLKMES WLALNDISLH QNLEPVAIKL APSDQTVVSQ GIFVGSQLSE ARIADNQVQQ  60
ALQNFGRYSS AVKEAAKVAP TTGLTTILDI ARIVSNFNPA LPNDKNNVPA YEKYVSKILQ  120
NPLIHLLNSS LKSFKRRTSD WNEVIDQIAN LYNGISAVDK GKIVESLKAL ANSASSSSSE  180
KQTEKLFTQS TINCEENIDI YIYSSSVTME EHNGKHNVKQ VEFEIQETQL RFTKELWSLY  240
SDAVLAKHLA LMDDWLNGID TKADNRLSTL TCLVGSGTHQ SGKTSGSMSN QDLQMESWLT  300
LNDVSLHQNI QTPLSFDLTS SLQDAAPVQD TISGGLIIGN TQNEAIDASN NVKNALQTYG  360
RFSNEVKESA QVSPIVGLTT ILDIARIVSN YNPALPTDQE NDETKKARVI AYNQYITKVL  420
QNPLMHLKSN YEKKYTKRTS NWKTAIDEIS NLYDGITEKD KEKIKNSLQA LAEAASSRSN  480
QANTENIFAQ NVIVCNNEEI EFCIYSSSVT MLYSGGKNTV RQVDFTLNET HIRFTKELWS  540
RYSDKVLDKH LALIDDWLLG ISTPNSDKTT LACFV                             575

SEQ ID NO: 72          moltype = DNA  length = 18
FEATURE                Location/Qualifiers
misc_feature           1..18
                       note = Synthetic DNA sequence encoding a cleavable linker,
                        Linker 1 thatis operably linked and in frame between two
                        toxin codingsequences.
source                 1..18
                       mol_type = other DNA
                       organism = synthetic construct
SEQUENCE: 72
ggtagtggcg gtgcttca                                                18

SEQ ID NO: 73          moltype = AA  length = 6
FEATURE                Location/Qualifiers
REGION                 1..6
                       note = Amino acid sequence of the cleavable linker, Linker
                        1.
source                 1..6
                       mol_type = protein
                       organism = synthetic construct
SEQUENCE: 73
GSGGAS                                                             6

SEQ ID NO: 74          moltype = DNA  length = 39
FEATURE                Location/Qualifiers
misc_feature           1..39
                       note = Synthetic DNA sequence encoding a flexible linker,
                        Linker 2 thatis operably linked and in frame between two
```

```
                            toxin codingsequences.
source                      1..39
                            mol_type = other DNA
                            organism = synthetic construct
SEQUENCE: 74
ggaagcggaa cacatcaatc tggtaagaca tcgggatct                        39

SEQ ID NO: 75               moltype = AA  length = 13
FEATURE                     Location/Qualifiers
REGION                      1..13
                            note = Amino acid sequence of the flexible linker, Linker 2.
source                      1..13
                            mol_type = protein
                            organism = synthetic construct
SEQUENCE: 75
GSGTHQSGKT SGS                                                    13

SEQ ID NO: 76               moltype = DNA  length = 1749
FEATURE                     Location/Qualifiers
misc_feature                1..1749
                            note = Synthetic sequence of an operon,
                            TIC7110-TIC6280operon,comprising the coding sequence of
                            TIC7110 followed by the codingsequence of TIC6280, wherein
                            an operon linker (Operon_Linker) isinserted between the
                            two coding sequences.
source                      1..1749
                            mol_type = other DNA
                            organism = synthetic construct
SEQUENCE: 76
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgatatt gctagaattg tttctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
tggaatgaag taattgacca aatcgccaat ttatataatg gcatttcggc agttgataaa  480
ggaaaaatcg tagaaagctt aaaagcatta gcaaattccg cctcttcttc tagctcagaa  540
aaacaaactg aaaaactatt tactcaaagc acgattaact gtgaggaaaa tattgatatt  600
tatatttact ctagctctgt tacaatggag gagcacaatg gaagcataaa tgtaaagcaa  660
gttgaatttg aaatacaaga aactcaatta agatttacaa aagaattgtg gagtttatac  720
tcagatgctg tgttagcaaa acatctagct ttaatggatg attggctcaa tggcattgat  780
acaaaagctg acaatcgttt ttccactctt acatgcttag tttaacaaaa tcaaatagat  840
taattgcaat gaagtttttt atatgttttt taaggaggaa ataatatgtc aaatcaagat  900
ttacagatgg aaagctggtt aacattaaat gatgtttccc ttcatcaaaa tattcaaaca  960
ccactttctt tcgaccttac ttcctcttta caagatgctg cacctgtcca agatactata  1020
agtggaggtt taattattgg taacacacaa aacgaagcta tcgatgccaa taataagtta  1080
aaaaatgcac tgcaaacata cggtcgtttt agtaatgagg tcaaagaatc tgctcaagta  1140
agtccgattg ttggattaac aactatactt gatattgcaa gaatagtttc caattacaac  1200
ccggctttgc ccactgatca agaaaatgat gaaactaaaa agcaagagt tattgcatac  1260
aaccaatata ttacgaaggt gttgcaaaat ccttaatgc acttaaaaag caactatgaa  1320
aaaaaataca caaacgaac ttctaactgg aagacagcta ttgatgaaat cagtaattta  1380
tatgatggca tcacagaaaa agataaagag aaaattaaaa atagtttaca agctttagca  1440
gaagctgctt cttcaagatc aaatcaagcc aatacagaaa atatatttgc tcaaaatgtt  1500
attgtgtgca atgatgaaga aattgaattt tgtatttatt caagttcagt tacaatgctt  1560
tatagtggtg gtaaaaatac cgtaagacag gttgatttca ctctaaacga aacccacatt  1620
agatttacaa aagagttatg gagtagatac tctgataaag ttttagataa acacttagcg  1680
ttgatagatg attggctact tggaattagt actcctaata gtgataaaac tactctcgct  1740
tgcttttgtt                                                       1749

SEQ ID NO: 77               moltype = DNA  length = 1749
FEATURE                     Location/Qualifiers
misc_feature                1..1749
                            note = Synthetic sequence of an operon,
                            TIC7111-TIC6282operon,comprising the coding sequence of
                            TIC7111 followed by the codingsequence of TIC6282, wherein
                            an operon linker (Operon_Linker) isinserted between the
                            two coding sequences.
source                      1..1749
                            mol_type = other DNA
                            organism = synthetic construct
SEQUENCE: 77
atgacaaatc ttgacttaaa aatggaaagc tggttagcac taaatgatat ttctctgcat  60
caaaatttag agcctgttgc tattaaactt gcaccatcag atcaaacagt tgtcagtcaa  120
ggaatctttg ttgggagtca gctgtcggag gctagaatcg ctgacaatca agttcagcaa  180
gcacttcaaa actttggacg ctatagttct gcagtaaaag aagctgctaa agtagctcca  240
acaactggat taacaactat tcttgacatt gctagaattg tctctaattt taatccagca  300
ttaccaaacg ataaaaataa tgttcctgct tatgaaaaat atgtgtcaaa aattttacaa  360
aacccactta tccatttatt aaatagcagt ctaaaatcct ttaaacgtag gacttccgat  420
```

```
tggaatgaag taattgacca aatcgccaat ttatataatg gcatttcggc agttgataaa    480
ggaaaaatcg tagaaagctt aaaagcatta gcaaattccg cctcttcttc tagctcagaa    540
aaacaaactg aaaaactatt tactcaaagc acgattaact gtgaggaaaa tattgatatt    600
tatatttact ctagctctgt tacaatggag gagcacaatg ggaagcataa tgtaaagcaa    660
gttgaatttg aaatacaaga aacacaatta agatttacaa aagaattgtg gagtttatac    720
tcagatgctg tgttagcaaa acatctagct ttaatggatg attggctcaa tggcattgat    780
acaaaagctg acaatcgttt atccactctt acatgcttag tttaacaaaa tcaaatagat    840
taattgcaat gaagttttt atatgttttt taaggaggaa ataatatgtc aaatcaagat     900
ttacagatgg aaagctggtt aacagtaaat gatgtttccc ttcatcaaaa tattcaaaca    960
ccactttctt tcgaccttac atcctcttta caagatgctg cacctgtcca agatactata   1020
agtggaggtt taattattgg taacacacaa aacgaagcta tcgatgccaa taataatgta   1080
aaaaatgcac tgcaaacata cggtcgtttt agtaatgagg tcaaagaatc tgctcaagta   1140
agtccgattg ttggattaac aactatactt gatattgcaa gaatagtttc caattacaac   1200
ccggctttgc ccactgatca agaaaatgat gaaactaaaa aagcaagagt tattgcatac   1260
aaccaatata ttacgaaggt gttgcaaaat cctttaatgc acttaaaaag caactatgaa   1320
aaaaaataca caaaacgaac ttctaactgg aagacagcta ttgaggaaat cagtaattta   1380
tatgatggca tcacagaaaa agataaagag aaaattaaaa atagtttaca agctttagca   1440
gaagctgcct cttcaagatc aaatcaagcc aatacagaaa atatatttgc tcaaaatgtt   1500
attgtgtgca atgatgaaga aattgaattt tgtatttatt caagttcagt tacaatgctt   1560
tatagtggtg gtaaaaatac cgtaagacag gttgatttca ctctaaacga aacccacatt   1620
agatttacaa aagagttatg gagtagatac tctgataaag tttagataa acacttagcg    1680
ttgatagatg attggctact tggaattagt actcctaata gtgataaaac tactctcgct   1740
tgctttgtt                                                            1749

SEQ ID NO: 78           moltype = DNA   length = 1749
FEATURE                 Location/Qualifiers
misc_feature            1..1749
                        note = Synthetic sequence of an operon,
                        TIC7109-TIC6281operon,comprising the coding sequence of
                        TIC7109 followed by the codingsequence of TIC6281, wherein
                        an operon linker (Operon_Linker) isinserted between the
                        two coding sequences.
source                  1..1749
                        mol_type = other DNA
                        organism = synthetic construct
SEQUENCE: 78
atgacaaatc ttgacttaaa aatggaaagc tggttagcac taaatgatat ttctctgcat      60
caaaatttag agcctgttgc tattaaactt gcaccatcag atcaaacagt tgtcagtcaa    120
ggaatctttg ttgggagtca gctgtcggag gctagaatcg ctgacaatca agttcagcaa    180
gcacttcaaa actttggacg ctatagttct gcagtaaaag aagctgctaa agtagctcca    240
acaactggat taacaactat tcttgatatt gctagaattg tttctaattt taatccagca    300
ttaccaaacg ataaaaataa tgttcctgct tatgaaaaat atgtgtcaaa aattttacaa    360
aacccactta tccatttatt aaatagcagt ctaaaatcct ttaaacgtag gacttccgat    420
tggaatgaag taattgacca aatcgccaat ttatataatg gcatttcggc agttgataaa    480
ggaaaaatcg tagaaagctt aaaagcatta gcaaattccg cctcttcttc tagctcagaa    540
aaacaaactg aaaaactatt tactcaaagc acgattaact gtgaggaaaa tattgatatt    600
tatatttact ctagctctgt tacaatggag gagcacaatg ggaagcataa tgtaaagcaa    660
gttgaatttg aaatacaaga aacacaatta agatttacaa aagaattgtg gagtttatac    720
tcagatgctg tgttagcaaa acatctagct ttaatggatg attggctcaa tggcattgat    780
acaaaagctg acaatcgttt atccactctt acatgcttag tttaacaaaa tcaaatagat    840
taattgcaat gaagttttt atatgttttt taaggaggaa ataatatgtc aaatcaagat     900
ttacagatgg aaagctggtt aacattaaat gatgtttccc ttcatcaaaa tattcaaaca    960
ccactttctt tcgaccttac ttcctcttta caagatgctg cacctgtcca agatactata   1020
agtggaggtt taattattgg taacacacaa aacgaagcta tcgatgccag taataatgta   1080
aaaaatgcac tgcaaacata cggtcgtttt agtaatgagg tcaaagaatc tgctcaagta   1140
agtccgattg ttggattaac aactatactt gatattgcaa gaatagtttc caattacaac   1200
ccggctttgc ccactgatca agaaaatgat gaaactaaaa aagcaagagt tattgcatac   1260
aaccaatata ttacgaaggt gttgcaaaat cctttaatgc acttaaaaag caactatgaa   1320
aaaaaataca caaaacgaac ttctaactgg aagacagcta ttgatgaaat cagtaattta   1380
tatgatggca tcacagaaaa agataaagag aaaattaaaa atagtttaca agctttagca   1440
gaagctgctt cttcaagatc aaatcaagcc aatacagaaa atatatttgc tcaaaatgtt   1500
attgtgtgca ataatgaaga aattgaattt tgtatttatt caagttcagt tacaatgctt   1560
tatagtggtg gtaaaaatac cgtaagacag gttgatttca ctctaaacga aacccacatt   1620
agatttacaa aagagttatg gagtagatac tctgataaag tttagataa acacttagcg    1680
ttgatagatg attggctact tggaattagt actcctaata gtgataaaac tactctcgct   1740
tgctttgtt                                                            1749

SEQ ID NO: 79           moltype = DNA   length = 40
FEATURE                 Location/Qualifiers
misc_feature            1..40
                        note = Synthetic sequence of a linker, Operon_Linker which
                         comprises atthe 5' end a stop codon to terminate
                         translation of a first toxingene and is inserted between
                         two toxin protein coding sequencesto permit expression of
                         both toxin proteins in the bacterial host
source                  1..40
                        mol_type = other DNA
                        organism = synthetic construct
SEQUENCE: 79
```

```
taacaaaatc aaatagatta attgcaatga agtttttat                         40

SEQ ID NO: 80           moltype = DNA   length = 885
FEATURE                 Location/Qualifiers
misc_feature            1..885
                        note = Nucleic acid sequence obtained from a metagenome
                          designatedMTG000070, encoding a TIC8808 pesticidal protein
                          with a Histidinetag operably linked to the 3' end,
                          TIC8808-His.
source                  1..885
                        mol_type = other DNA
                        organism = synthetic construct
SEQUENCE: 80
atgtcaaatc aagatttaca gatggaaagc tggttaacag taaatgatgt ttcacttcat  60
caaaatattc aaacaccact ttctttcgac catactacat ctctacaaga tacaacacct  120
gtccaagaca ctataagtgg aggtttaatt attggtcaca acaaaatgaa agctattgat  180
gccaataata atgtaaaaaa tgcattacaa acgtatgacc gttttagtaa tgaggtcaaa  240
gaatctgccc aaataagtcc aattgttgga ttaacaacta tacttgatat cgcaagaata  300
gtttccaatt acaatcctgc tttgcccact gaccaagaaa ataatgaaac taaaaaagca  360
aaagttgctg catacaacca atatattacg aaggtgctgc aaaatccttt aatgcactta  420
aaaagcaact atgaaaaaaa atacacgaaa ataacttcta actggaagac agctattgat  480
gaaattagta atttatatga tgggatcaca gaaaaagata agagaaaaat taaaactagt  540
ttacacgctt tagcagaagc tgcctcttca agatcaaata aagccaatac agaaaatata  600
tttgctcaaa atgtcatagt gtgcaatgat gaagaaattg aatttgcat ttattcaagt  660
tcagttcaa tgctttatag tgatggtaaa aatcccgtga gacaggttga ttttacacta  720
aacgaaaccc acattagatt tacaaaagaa ttattctga tattgtttta  780
gctaaacact tagcgttgtt cgatgattgg ctacttggta ttagtacacc taatagtgat  840
aaaactactc ttgcttgctt tgctcaccat catcaccatc actag                  885

SEQ ID NO: 81           moltype = AA   length = 295
FEATURE                 Location/Qualifiers
REGION                  1..295
                        note = The amino acid sequence of the TIC8808-His protein.
source                  1..295
                        mol_type = protein
                        organism = synthetic construct
SEQUENCE: 81
MSNQDLQMES WLTVNDVSLH QNIQTPLSFD HTTSLQDTTP VQDTISGGLI IGHKQNEAID  60
ANNNVKNALQ TYDRFSNEVK ESAQISPIVG LTTILDIARI VSNYNPALPT DQENNETKKA  120
KVAAYNQYIT KVLQNPLMHL KSNYEKKYTK ITSNWKTAID EISNLYDGIT EKDKEKIKTS  180
LHALAEAASS RSNKANTENI FAQNVIVCND EEIEFCIYSS SVTMLYSDGK NTVRQVDFTL  240
NETHIRFTKE LWSRYSDIVL AKHLALFDDW LLGISTPNSD KTTLACFAHH HHHH        295

SEQ ID NO: 82           moltype = DNA   length = 930
FEATURE                 Location/Qualifiers
misc_feature            1..930
                        note = Nucleic acid sequence obtained from a metagenome
                          designatedMTG000415, encoding a TIC9480 pesticidal protein
                          with a Histidinetag operably linked to the 3' end,
                          TIC9480-His.
source                  1..930
                        mol_type = other DNA
                        organism = synthetic construct
SEQUENCE: 82
atgtcaaatc aagatttaca gatggaaagc tggttaacag taaatgatgt ttcacttcat  60
caaaatattc aaacaccact ttctttcgac catactacat ctctacaaga tacaacacct  120
gtccaagaca ctataagtgg aggtttaatt attggtcaca acaaaatgaa agctattgat  180
gccaataata atgtaaaaaa tgcattacaa acgtatgacc gttttagtaa tgaggtcaaa  240
gaatctgccc aaataagtcc aattgttgga ttaacaacta tacttgatat cgcaagaata  300
gtttccaatt acaatcctgc tttgcccact gaccaagaaa ataatgaaac taaaaaagca  360
aaagttgctg catacaacca atatattacg aaggtgctgc aaaatccttt aatgcactta  420
aaaagcaact atgaaaaaaa atacacgaaa ataacttcta actggaagac agctattgat  480
gaaattagta atttatatga tgggatcaca gaaaaagata agagaaaaat taaaactagt  540
ttacacgctt tagcagaagc tgcctcttca agatcaaata aagccaatac agaaaatata  600
tttgctcaaa atgtcatagt gtgcaatgat gaagaaattg aatttgcat ttattcaagt  660
tcagttacaa tgctttatag tgatggtaaa aatcccgtga gacaggttga ttttacacta  720
aacgaaaccc acattagatt tacaaaagaa ttatggagta gatattctga tattgtttta  780
gctaagcgtt gttcgatgat tggctacttg gtattagtac acctaatagt gataaaacta  840
ctcttgcttg ctttgcttaa aatatctatc aaaaggaaac tagataactt tttgtttcct  900
tttgatcttc accatcatca ccatcactag                                   930

SEQ ID NO: 83           moltype = AA   length = 310
FEATURE                 Location/Qualifiers
REGION                  1..310
                        note = The amino acid sequence of the TIC9480-His protein.
source                  1..310
                        mol_type = protein
                        organism = synthetic construct
SEQUENCE: 83
```

```
MSNQDLQMES WLTVNDVSLH QNIQTPLSFD HTTSLQDTTP VQDTISGGLI IGHKQNEAID    60
ANNNVKNALQ TYDRFSNEVK ESAQISPIVG LTTILDIARI VSNYNPALPT DQENNETKKA   120
KVAAYNQYIT KVLQNPLMHL KSNYEKKYTK ITSNWKTAID EISNLYDGIT EKDKEKIKTS   180
LHALAEAASS RSNKANTENI FAQNVIVCND EEIEFCIYSS SVTMLYSDGK NTVRQVDFTL   240
NETHIRFTKE LWSRYSDIVL AKRCSMIGYL VLVHLIVIKL LLLALLKISI KRKLDNFLFP   300
FDLHHHHHH                                                          310

SEQ ID NO: 84             moltype = DNA  length = 930
FEATURE                   Location/Qualifiers
misc_feature              1..930
                          note = Nucleic acid sequence obtained from a metagenome
                           designatedMTG000199, encoding a TIC9257 pesticidal protein
                           with a Histidinetag operably linked to the 3' end,
                           TIC9257-His.
source                    1..930
                          mol_type = other DNA
                          organism = synthetic construct
SEQUENCE: 84
atgtcaaatc aagatttaca gatggaaagc tggttaacag taaatgatgt ttcacttcat    60
caaaatattc aaacaccact ttctttcgac catactacat ctctacaaga taacaccct   120
gtccaagaca ctataagtgg aggtttaatt attggtcaca acaaaatga agctattgat   180
gccaataata atgtaaaaaa tgcattacaa acgtatgacc gttttagtaa tgaggtcaaa   240
gaatctgccc aaataagtcc aattgttgga ttaacaacta tacttgatat cgcaagaata   300
gttccaatt acaatcctgc tttgcccact gaccaagaaa ataatgaaac taaaaaagca   360
aaagttgctg catacaacca atatattcg aaggtgctgc aaaatccttt aatgcactta   420
aaaagcaact atgaaaaaaa atacacgaaa ataacttcta actggaagca agctattgat   480
gaaattagta atttatatga tgggatcaca gaaaaagata agagaaaat taaaactagt   540
ttacacgctt tagcagaagc tgcctcttca agatcaaata aagccaatac agaaaatata   600
tttgctcaaa atgtcatagt gtgcaatgat gaagaaattg aatttgcat ttattcaagt   660
tcagttacaa tgcttatag tgatggtaaa aataccgtga gacaggttga ttttacacta   720
aacgaaaccc acattagatt tacaaaagaa ttatggagta gatattctga tattgttta   780
gctaagcgtt gttcgatgat tggctacttg gtattagtac acctaatagt gataaaacta   840
ctcttgcttc ctttgcttaa aatatctatc aaaaggaaac tagaaaactt tttgtttcct   900
tttgatcttc accatcatca ccatcactag                                   930

SEQ ID NO: 85             moltype = AA  length = 310
FEATURE                   Location/Qualifiers
REGION                    1..310
                          note = The amino acid sequence of the TIC9257-His protein.
source                    1..310
                          mol_type = protein
                          organism = synthetic construct
SEQUENCE: 85
MSNQDLQMES WLTVNDVSLH QNIQTPLSFD HTTSLQDTTP VQDTISGGLI IGHKQNEAID    60
ANNNVKNALQ TYDRFSNEVK ESAQISPIVG LTTILDIARI VSNYNPALPT DQENNETKKA   120
KVAAYNQYIT KVLQNPLMHL KSNYEKKYTK ITSNWKTAID EISNLYDGIT EKDKEKIKTS   180
LHALAEAASS RSNKANTENI FAQNVIVCND EEIEFCIYSS SVTMLYSDGK NTVRQVDFTL   240
NETHIRFTKE LWSRYSDIVL AKRCSMIGYL VLVHLIVIKL LLLALLKISI KRKLENFLFP   300
FDLHHHHHH                                                          310

SEQ ID NO: 86             moltype = DNA  length = 849
FEATURE                   Location/Qualifiers
misc_feature              1..849
                          note = Nucleic acid sequence obtained from a metagenome
                           designatedMTG000120, encoding a TIC9258 pesticidal protein
                           with a Histidinetag operably linked to the 3' end,
                           TIC9258-His.
source                    1..849
                          mol_type = other DNA
                          organism = synthetic construct
SEQUENCE: 86
atgacaaatc ttgacttaaa aatggaaagc tggttagcac taaatgatat ttctctacat    60
caaaatttag agcctgttgc tattaaactt gcaacatcag atcaaacagt tgtcagtcaa   120
ggtatctttg ttgggaatca gctgtcagag gctagaatg ctgcaatca agttcagcag   180
gcacttcaaa gctttggacg ctatagtact gctgtaaaag aagctgctaa agtagctcca   240
acaactggat taacaactat ccttgacatt tctagaattt tttctaattt caacccagca   300
ttaccaaacg ataaaaataa tgtacctgcc tatgaaaaat atgtttcaaa atattacaa   360
aacccactta tccatttatt aaatagcagt gtaaaatcag tcaaacgtac gacttccgat   420
tggaatgaag caattgacca aattgccaat ttatataatg gcatttcggc agctgacaaa   480
ggaaaaattg tagaaagctt aaaagcatta gcaaaatccg cctcttcttc tagctctgaa   540
aaacaaacgg aaaaactatt tactcaaagt acgattaact gtgaggaaaa tatagatatt   600
tatatttact ctagctctgt cacaatggag gagcacaacg gtaagcacaa tgtaaagcag   660
gttgaatttg aaatacaaga aacacaatta agatttacaa aagaattgtg gagtgtatac   720
tctgatgctg tgttagctaa acatcatagct ctaatggatg attggctaaa tggtattgat   780
acaaaagcag acaatcgttt atccactctt acttgctag ttcaccacca tcacgctcac   840
catcactga                                                          849

SEQ ID NO: 87             moltype = AA  length = 282
FEATURE                   Location/Qualifiers
```

```
REGION                       1..282
                             note = The amino acid sequence of the TIC9258-His protein.
source                       1..282
                             mol_type = protein
                             organism = synthetic construct
SEQUENCE: 87
MTNLDLKMES WLALNDISLH QNLEPVAIKL ATSDQTVVSQ GIFVGNQLSE ARIADNQVQQ    60
ALQSFGRYST AVKEAAKVAP TTGLTTILDI SRIVSNFNPA LPNDKNNVPA YEKYVSKILQ   120
NPLIHLLNSS VKSFKRTTSD WNEAIDQIAN LYNGISAADK GKIVESLKAL AKSASSSSSE   180
KQTEKLFTQS TINCEENIDI YIYSSSVTME EHNGKHNVKQ VEFEIQETQL RFTKELWSVY   240
SDAVLAKHLA LMDDWLNGID TKADNRLSTL TCLVHHHHAH HH                      282

SEQ ID NO: 88                moltype = DNA  length = 849
FEATURE                      Location/Qualifiers
misc_feature                 1..849
                             note = Nucleic acid sequence obtained from a designated
                             MTG000184,encoding a TIC9259 pesticidal protein with a
                             Histidine tagoperably linked to the 3' end, TIC9259-His.
source                       1..849
                             mol_type = other DNA
                             organism = synthetic construct
SEQUENCE: 88
atgacaaatc ttgacttaaa aatggaaagt tggttagcac taaatgatat ttctctacat    60
caaaatttag agcctgttgc tattaaactc gcaacatcag atcaaacagt tgtcagtcaa   120
ggaatctttg tagggaatca gttgtcggag gctagaattg ctgacaatca ggttcagcag   180
gcacttcaaa gctttggacg ctatagtact gctgtaaaag aagctgctaa agtagctcca   240
acaactggtt taacaactat ccttgacatt gctagcatcg tttctaattt caatccggca   300
ttaccaaacg ataaaaataa tgtacctgcc tatgaaaaat atgtttcaaa atattacaa   360
aacccactta tccatttatt aaatagcagt gtaaaatcct tcaaacgtac gacttctgat   420
tggaatgaag caattgacca aattgccaat ttatataacg gcatttcggc agctgacaaa   480
ggaaaaattg tagaaagctt aaaagcatta gcaaaatccg cctcctcttc tagctctgaa   540
aaacaaacgg aaaaactatt tactcaaagt acgattaact gtgaggaaaa tatagatatt   600
tatatttact ctagctctgt cacaatggag gagcacaacg gtaagcacaa tgtaaagcag   660
gttgaatttg aaatacaaga aacacaatta agatttacaa aagaatttgtg gagtttatac   720
tctgatgctg tgttagctaa acatctagct ctaatggatg attggctaaa tggcattgat   780
acaaaagcag acaatcgttt atccactctt acatgcttag ttcaccacca tcacgctcac   840
catcactga                                                           849

SEQ ID NO: 89                moltype = AA  length = 282
FEATURE                      Location/Qualifiers
REGION                       1..282
                             note = The amino acid sequence of the TIC9259-His protein.
source                       1..282
                             mol_type = protein
                             organism = synthetic construct
SEQUENCE: 89
MTNLDLKMES WLALNDISLH QNLEPVAIKL ATSDQTVVSQ GIFVGNQLSE ARIADNQVQQ    60
ALQSFGRYST AVKEAAKVAP TTGLTTILDI ASIVSNFNPA LPNDKNNVPA YEKYVSKILQ   120
NPLIHLLNSS VKSFKRTTSD WNEAIDQIAN LYNGISAADK GKIVESLKAL AKSASSSSSE   180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLVHHHHAH HH                      282

SEQ ID NO: 90                moltype = DNA  length = 867
FEATURE                      Location/Qualifiers
misc_feature                 1..867
                             note = Nucleic acid sequence obtained from a plate-scrape
                             metagenomedesignated MTG000184, encoding a TIC8808
                             pesticidal protein.
source                       1..867
                             mol_type = other DNA
                             organism = unidentified
SEQUENCE: 90
atgtcaaatc aagatttaca gatggaaagc tggttaacag taaatgatgt ttcacttcat    60
caaaatattc aaacaccact ttctttcgac catactacat ctctacaaga tacaacacct   120
gtccaagaca ctataagtgg aggtttaatt attggtcaca acaaaatga agctattgat   180
gccaataata atgtaaaaaa tgcattacaa acgtatgacc gttttagtaa tgaggtcaaa   240
gaatctgccc aaataagtcc aattgttgga ttaacaacta tacttgatat cgcaagaata   300
gtttccaatt acaatcctgc tttgcccact gaccaagaaa ataatgaaac taaaaaagca   360
aagttgctg catacaacca atatattacg aaggtgctgc aaaatccttt aatgcactta   420
aaaagcaact atgaaaaaaa atacacgaaa ataacttcta actggaagac agctattgat   480
gaaattagta atttatatga tgggatcaca gaaaaagata agagaaaat taaaactagt   540
ttacacgctt tagcagaagc tgcctcttca agatcaaata aagccaatac agaaaatata   600
tttgctcaaa atgtcatagt gtgcaatgat gaagaaattg aatttgcat ttattcaagt   660
tcagttacaa tgctttatag tgatggtaaa aataccgtaga cacggttga tttacacta   720
aacgaaaccc acattagatt tacaaaagaa ttatggagta gatattctga tattgtttta   780
gctaaacact tagcgttgtt cgatgattgg ctacttggta ttagtacacc taatagtgat   840
aaaactactc ttgcttgctt tgcttga                                       867

SEQ ID NO: 91                moltype = AA  length = 288
```

```
FEATURE                 Location/Qualifiers
REGION                  1..288
                        note = The amino acid sequence of the TIC8808 protein.
source                  1..288
                        mol_type = protein
                        organism = unidentified
SEQUENCE: 91
MSNQDLQMES WLTVNDVSLH QNIQTPLSFD HTTSLQDTTP VQDTISGGLI IGHKQNEAID    60
ANNNVKNALQ TYDRFSNEVK ESAQISPIVG LTTILDIARI VSNYNPALPT DQENNETKKA   120
KVAAYNQYIT KVLQNPLMHL KSNYEKKYTK ITSNWKTAID EISNLYDGIT EKDKEKIKTS   180
LHALAEAASS RSNKANTENI FAQNVIVCND EEIEFCIYSS SVTMLYSDGK NTVRQVDFTL   240
NETHIRFTKE LWSRYSDIVL AKHLALFDDW LLGISTPNSD KTTLACFA                288

SEQ ID NO: 92           moltype = DNA   length = 912
FEATURE                 Location/Qualifiers
misc_feature            1..912
                        note = Nucleic acid sequence obtained from a plate-scrape
                         metagenomedesignated MTG000415, encoding a TIC9480
                         pesticidal protein.
source                  1..912
                        mol_type = other DNA
                        organism = unidentified
SEQUENCE: 92
atgtcaaatc aagatttaca gatggaaagc tggttaacag taaatgatgt ttcacttcat    60
caaaatattc aaacaccact ttctttcgac catactacat ctctacaaga tacaacacct   120
gtccaagaca ctataagtgg aggtttaatt attggtcaca aacaaaatga agctattgat   180
gccaataata atgtaaaaaa tgcattacaa acgtatgacc gttttagtaa tgaggtcaaa   240
gaatctgccc aaataagtcc aattgttgga ttaacaacta tacttgatat cgcaagaata   300
gtttccaatt acaatcctgc tttgcccact gaccaagaaa ataatgaaac taaaaaagca   360
aaagttgctg catacaacca atatattacg aaggtgctg aaaatccttt aatgcactta    420
aaaagcaact atgaaaaaaa atacacgaaa ataacttcta actggaagac agctattgat   480
gaaattagta atttatatga tgggatcaca gaaaaagata agagaaaat taaaactagt    540
ttacacgctt tagcagaagc tgcctcttca agatcaaata aagccaatac agaaaatata   600
tttgctcaaa atgtcatagt gtgcaatgat gaagaaattg aattttgcat ttattcaagt   660
tcagttacaa tgctttatag tgatggtaaa aataccgtga gacaggttga ttttacacta   720
aacgaaaccc acattagatt tacaaaagaa ttatggagta gatattctga tattgtttta   780
gctaagcgtt gttcgatgat tggctacttg gtattagtac acctaatagt gataaaacta   840
ctcttgcttg cttgcttaa aatatctatc aaaaggaaac tagataactt tttgtttcct   900
tttgatcttt ga                                                       912

SEQ ID NO: 93           moltype = AA   length = 303
FEATURE                 Location/Qualifiers
REGION                  1..303
                        note = The amino acid sequence of the TIC9480 protein.
source                  1..303
                        mol_type = protein
                        organism = unidentified
SEQUENCE: 93
MSNQDLQMES WLTVNDVSLH QNIQTPLSFD HTTSLQDTTP VQDTISGGLI IGHKQNEAID    60
ANNNVKNALQ TYDRFSNEVK ESAQISPIVG LTTILDIARI VSNYNPALPT DQENNETKKA   120
KVAAYNQYIT KVLQNPLMHL KSNYEKKYTK ITSNWKTAID EISNLYDGIT EKDKEKIKTS   180
LHALAEAASS RSNKANTENI FAQNVIVCND EEIEFCIYSS SVTMLYSDGK NTVRQVDFTL   240
NETHIRFTKE LWSRYSDIVL AKRCSMIGYL VLVHLIVIKL LLLALLKISI KRKLDNFLFP   300
FDL                                                                 303

SEQ ID NO: 94           moltype = DNA   length = 912
FEATURE                 Location/Qualifiers
misc_feature            1..912
                        note = Nucleic acid sequence obtained from a plate-scrape
                         metagenomedesignated MTG000199, encoding a TIC9257
                         pesticidal protein.
source                  1..912
                        mol_type = other DNA
                        organism = unidentified
SEQUENCE: 94
atgtcaaatc aagatttaca gatggaaagc tggttaacag taaatgatgt ttcacttcat    60
caaaatattc aaacaccact ttctttcgac catactacat ctctacaaga tacaacacct   120
gtccaagaca ctataagtgg aggtttaatt attggtcaca aacaaaatga agctattgat   180
gccaataata atgtaaaaaa tgcattacaa acgtatgacc gttttagtaa tgaggtcaaa   240
gaatctgccc aaataagtcc aattgttgga ttaacaacta tacttgatat cgcaagaata   300
gtttccaatt acaatcctgc tttgcccact gaccaagaaa ataatgaaac taaaaaagca   360
aaagttgctg catacaacca atatattacg aaggtgctgc aaaatccttt aatgcactta   420
aaaagcaact atgaaaaaaa atacacgaaa ataacttcta actggaagac agctattgat   480
gaaattagta atttatatga tgggatcaca gaaaaagata agagaaaat taaaactagt    540
ttacacgctt tagcagaagc tgcctcttca agatcaaata aagccaatac agaaaatata   600
tttgctcaaa atgtcatagt gtgcaatgat gaagaaattg aattttgcat ttattcaagt   660
tcagttacaa tgctttatag tgatggtaaa aataccgtga gacaggttga ttttacacta   720
aacgaaaccc acattagatt tacaaaagaa ttatggagta gatattctga tattgtttta   780
gctaagcgtt gttcgatgat tggctacttg gtattagtac acctaatagt gataaaacta   840
```

```
ctcttgcttg ctttgcttaa aatatctatc aaaaggaaac tagaaaactt tttgtttcct    900
tttgatcttt ga                                                         912

SEQ ID NO: 95            moltype = AA   length = 303
FEATURE                  Location/Qualifiers
REGION                   1..303
                         note = The amino acid sequence of the TIC9257 protein.
source                   1..303
                         mol_type = protein
                         organism = unidentified
SEQUENCE: 95
MSNQDLQMES WLTVNDVSLH QNIQTPLSFD HTTSLQDTTP VQDTISGGLI IGHKQNEAID    60
ANNNVKNALQ TYDRFSNEVK ESAQISPIVG LTTILDIARI VSNYNPALPT DQENNETKKA    120
KVAAYNQYIT KVLQNPLMHL KSNYEKKYTK ITSNWKTAID EISNLYDGIT EKDKEKIKTS    180
LHALAEAASS RSNKANTENI FAQNVIVCND EEIEFCIYSS SVTMLYSDGK NTVRQVDFTL    240
NETHIRFTKE LWSRYSDIVL AKRCSMIGYL VLVHLIVIKL LLLALLKISI KRKLENFLFP    300
FDL                                                                   303

SEQ ID NO: 96            moltype = DNA   length = 825
FEATURE                  Location/Qualifiers
misc_feature             1..825
                         note = Nucleic acid sequence obtained from a plate-scrape
                           metagenomedesignated MTG000120, encoding a TIC9258
                           pesticidal protein.
source                   1..825
                         mol_type = other DNA
                         organism = unidentified
SEQUENCE: 96
atgacaaatc ttgacttaaa aatggaaagc tggttagcac taaatgatat ttctctacat    60
caaaatttag agcctgttgc tattaaactt gcaacatcag atcaaacagt tgtcagtcaa    120
ggtatctttg ttgggaatca gctgtcagag gctagaattg ctgacaatca agttcagcag    180
gcacttcaaa gctttggacg ctatagtact gctgtaaaag aagctgctaa agtagctcca    240
acaactggat taacaactat ccttgacatt tctagaattg tttctaattt caacccagca    300
ttaccaaacg ataaaaataa tgtacctgcc tatgaaaaat atgtttcaaa aatattacaa    360
aacccactta tccatttatt aaatagcagt gtaaaatcct tcaaacgtac gacttccgat    420
tggaatgaag caattgacca aattgccaat ttatataatg gcatttcggc agctgacaaa    480
ggaaaaattg tagaaagctt aaaagcatta gcaaatccg cctcttcttc tagctctgaa    540
aaacaaacgg aaaaactatt tactcaaagt acgattaact gtgaggaaaa tatagatatt    600
tatatttact ctagctctgt cacaatggag gagcacaacg gtaagcacaa tgtaaagcag    660
gttgaatttg aaatacaaga aacacaatta agatttacaa aagaattgtg gagtgtatac    720
tctgatgctg tgttagctaa acatctagct ctaatggatg attggctaaa tggtattgat    780
acaaaagcag acaatcgttt atccactctt acttgcttag tttaa                    825

SEQ ID NO: 97            moltype = AA   length = 274
FEATURE                  Location/Qualifiers
REGION                   1..274
                         note = The amino acid sequence of the TIC9258 protein.
source                   1..274
                         mol_type = protein
                         organism = unidentified
SEQUENCE: 97
MTNLDLKMES WLALNDISLH QNLEPVAIKL ATSDQTVVSQ GIFVGNQLSE ARIADNQVQQ    60
ALQSFGRYST AVKEAAKVAP TTGLTTILDI SRIVSNFNPA LPNDKNNVPA YEKYVSKILQ    120
NPLIHLLNSS VKSFKRTTSD WNEAIDQIAN LYNGISAADK GKIVESLKAL AKSASSSSSE    180
KQTEKLFTQS TINCEENIDI YIYSSSVTME EHNGKHNVKQ VEFEIQETQL RFTKELWSVY    240
SDAVLAKHLA LMDDWLNGID TKADNRLSTL TCLV                                 274

SEQ ID NO: 98            moltype = DNA   length = 825
FEATURE                  Location/Qualifiers
misc_feature             1..825
                         note = Nucleic acid sequence obtained from a plate-scrape
                           metagenomedesignated MTG000184, encoding a TIC9259
                           pesticidal protein.
source                   1..825
                         mol_type = other DNA
                         organism = unidentified
SEQUENCE: 98
atgacaaatc ttgacttaaa aatggaaagt tggttagcac taaatgatat ttctctacat    60
caaaatttag agcctgttgc tattaaactc gcaacatcag atcaaacagt tgtcagtcaa    120
ggaatctttg tagggaatca gttgtcggag gctagaattg ctgacaatca ggttcagcag    180
gcacttcaaa gctttggacg ctatagtact gctgtaaaag aagctgctaa agtagctcca    240
acaactggtt taacaactat ccttgacatt gctagcatcg tttctaattt caatccggca    300
ttaccaaacg ataaaaataa tgtacctgcc tatgaaaaat atgtttcaaa aatattacaa    360
aacccactta tccatttatt aaatagcagt gtaaaatcct tcaaacgtac gacttccgat    420
tggaatgaag caattgacca aattgccaat ttatataatg gcatttcggc agctgacaaa    480
ggaaaaattg tagaaagctt aaaagcatta gcaaatccg cctcttcttc tagctctgaa    540
aaacaaacgg aaaaactatt tactcaaagt acgattaact gtgaggaaaa tatagatatt    600
tatatttact ctagctctgt cacaatggag gagcacaacg gtaagcacaa tgtaaagcag    660
gttgaatttg aaatacaaga aacacaatta agatttacaa aagaattgtg gagtttatac    720
```

```
tctgatgctg tgttagctaa acatctagct ctaatggatg attggctaaa tggcattgat  780
acaaaagcag acaatcgttt atccactctt acatgcttag tttaa                  825

SEQ ID NO: 99          moltype = AA  length = 274
FEATURE                Location/Qualifiers
REGION                 1..274
                       note = The amino acid sequence of the TIC9259 protein.
source                 1..274
                       mol_type = protein
                       organism = unidentified
SEQUENCE: 99
MTNLDLKMES WLALNDISLH QNLEPVAIKL ATSDQTVVSQ GIFVGNQLSE ARIADNQVQQ    60
ALQSFGRYST AVKEAAKVAP TTGLTTILDI ASIVSNFNPA LPNDKNNVPA YEKYVSKILQ   120
NPLIHLLNSS VKSFKRTTSD WNEAIDQIAN LYNGISAADK GKIVESLKAL AKSASSSSSE   180
KQTEKLFTQS TINCEENIDI YIYSSSVTME EHNGKHNVKQ VEFEIQETQL RFTKELWSLY   240
SDAVLAKHLA LMDDWLNGID TKADNRLSTL TCLV                              274
```

INSECT INHIBITORY PROTEINS

REFERENCE TO RELATED APPLICATION

This application is a divisional of U.S. application Ser. No. 16/895,921, filed Jun. 8, 2020, which application is a divisional of U.S. application Ser. No. 15/846,796, filed Dec. 19, 2017, now U.S. Pat. No. 10,717,989), which claims the benefit of U.S. Provisional Application No. 62/436,736, filed Dec. 20, 2016, each of which are herein incorporated by reference in their entireties.

INCORPORATION OF SEQUENCE LISTING

The file named "MONS431USD2.xml" containing a computer readable form of the Sequence Listing was created on Oct. 4, 2022. This file is 205,200 bytes (measured in MS-Windows®), is contemporaneously filed by electronic submission (using the United States Patent Office EFS-Web filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed proteins are insecticidally active against agriculturally-relevant pests of crop plants and seeds, particularly Coleopteran, Lepidopteran, Hemipteran and Thysanopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, Coleoptera, Hemipteran, and Thysanopteran, are considered a major cause of damage to field crops, thereby decreasing crop yields over infested areas.

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of unrelated bacterial species, such as *Brevibacillus laterosporus* and *Lysinibacillus sphaericus* ("Ls" formerly known as *Bacillus sphaericus*).

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors disclose a novel protein toxin family from *Lysinibacillus sphaericus* along with similar toxin proteins, variant proteins, and exemplary recombinant proteins that exhibit insecticidal activity against target Lepidopteran, Coleopteran, Hemipteran and Thysanopteran pest species, particularly against Western Corn Rootworm (*Diabrotica virgifera virgifera*).

SUMMARY OF THE INVENTION

Disclosed herein is a novel group of pesticidal proteins with insect inhibitory activity (toxin proteins), referred to herein as TIC6280-related toxin proteins (TIC6280, TIC6281, TIC6282, and TIC6283) and TIC7016-related toxin proteins (TIC7016, TIC7017, TIC7108, TIC7110, and TIC7589), which are shown to exhibit inhibitory activity against one or more pests of crop plants. The TIC6280-related toxin proteins and the TIC7016-related toxin proteins toxin classes can be used alone, as chimeras, to make fusion proteins, or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or fragment thereof, wherein: (a) said pesticidal protein comprises an amino acid sequence selected from the group consisting of: SEQ ID NOs:2, 4, 6, 8, 10, 12, 15, 18, 21, 23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (b) said pesticidal protein comprises an amino acid sequence having at least 62%, or 65%, or 70%, or 75%, or 80%, or 85%, or 90%, or 95%, or about 100% amino acid sequence identity to an amino acid sequence selected from the group consisting of: SEQ ID NOs:2, 4, 6, 8, 10, 12, 15, 18, 21, 23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (c) said polynucleotide segment hybridizes to a polynucleotide having a nucleotide sequence selected from the group consisting of: SEQ ID NOs:1, 3, 5, 7, 9, 11, 13, 14, 16, 17, 19, 20, 22, 24, 26, 28, 30, 32, 34, 35, 37, 38, 40, 41, 43, 44, 45, 46, 48, 50, 52, 54, 56, 58, 60, 62, 64, 66, 68, 70, 80, 82, 84, 86, 88, 90, 92, 94, 96, and 98; or (d) said recombinant nucleic acid molecule is in operable linkage to a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated host cells include *Agrobacterium*, *Rhizobium*, *Bacillus*, *Brevibacillus*, *Escherichia*, *Pseudomonas*, *Klebsiella*, and *Erwinia*; and wherein said *Bacillus* species is a *Bacillus cereus* or a *Bacillus thuringiensis*, said *Brevibacillus* is a *Brevibacillus laterosperous*, and said *Escherichia* is an *Escherichia coli*. Contemplated plant host cells include a dicotyledonous cell and a monocotyledonous cell. Further contemplated plant host cells include an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against an insect species of the order of Coleoptera, including Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*.

In another embodiment, the pesticidal protein exhibits activity against an insect species of the order of Lepidoptera, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Oriental leaf worm, Pink bollworm, Black cutworm, Southwestern Corn Borer, Diamondback moth, and European corn borer.

In yet another embodiment, the pesticidal protein exhibits activity against an insect species of the order of Hemiptera, including Southern Green Stinkbug, Neotropical Brown Stinkbug, Western Tarnished Plant Bug, or Tarnished Plant Bug.

In another embodiment, the pesticidal protein exhibits activity against an insect species of the order of Thysanoptera, including Tobacco Thrips (*Frankliniella fusca*), Flower Thrips (*Frankliniella tritici*), Western Flower Thrips (*Frankliniella occidentalis*), and Soybean Thrips (*Sericothrips variabilis*).

Also contemplated in this application are plants comprising a recombinant nucleic acid molecule comprising a heterologous promoter operably linked to a polynucleotide segment encoding a pesticidal protein or fragment thereof, wherein: (a) said pesticidal protein comprises an amino acid sequence selected from the group consisting of: SEQ ID NOs:23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (b) said pesticidal protein comprises an amino acid sequence having at least 62%, or 65%, or 70%, or 75%, or 80%, or 85%, or 90%, or 95%, or about 100% amino acid sequence identity to an amino acid sequence selected from the group consisting of: SEQ ID NOs:23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (c) said polynucleotide segment hybridizes under stringent hybridization conditions to the compliment of a nucleotide sequence selected from the group consisting of: SEQ ID NOs:43, 44, 45, 46, 48, 50, 52; or (d) said plant exhibits a detectable amount of said pesticidal protein, wherein the pesticidal protein is selected from the group consisting of: SEQ ID NOs:23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99. In one embodiment, the plant is either a monocot or a dicot. In another embodiment, the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. The at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, or Hemiptera. The at least one other pesticidal agent in the insect inhibitory composition is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, VIP3A, VIP3B, VIP3Ab, AXMI-001, AXMI-002, AXMI-030, AXMI-035, AXMI-036, AXMI-045, AXMI-52, AXMI-58, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-07, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-R1 and variants thereof, IP3 and variants thereof, DIG-3, DIG-5, DIG-10 and a DIG-11protein.

Commodity products comprising a detectable amount of the recombinant nucleic acid molecules disclosed in this application are contemplated. Such commodity products include commodity corn bagged by a grain handler, corn flakes, corn cakes, corn flour, corn meal, corn syrup, corn oil, corn silage, corn starch, corn cereal, and the like, and corresponding cotton commodity products such as whole or processed cotton seed, cotton oil, lint, seeds and plant parts processed for feed or food, fiber, paper, biomasses, and fuel products such as fuel derived from cotton oil or pellets derived from cotton gin waste, and corresponding soybean commodity products such as whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and corresponding rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

Also contemplated in this application are methods of producing seed comprising the recombinant nucleic acid molecules disclosed in this application. The method will comprise planting at least one of the seed comprising the recombinant nucleic acid molecules disclosed in this application; growing plant from the seed; and harvesting seed from the plants, wherein the harvested seed comprises the recombinant nucleic acid molecules in this application.

In another embodiment, a plant resistant to insect infestation, wherein the cells of said plant optionally comprise: (a) a recombinant nucleic acid molecule encoding an insecticidally effective amount of a pesticidal protein, wherein the protein is selected from the group consisting of: SEQ ID NOs:23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (b) an insecticidally effective amount of a protein comprising an amino acid sequence having at least 62%, or 65%, or 70%, or 75%, or 80%, or 85%, or 90%, or 95%, or about 100% amino acid sequence identity to an amino acid sequence selected from the group consisting of: SEQ ID NOs:23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99.

Also disclosed in this application are methods for controlling a Coleopteran or Lepidopteran or Hemipteran or Thysanopteran species pest, and controlling a Coleopteran or Lepidopteran or Hemipteran or Thysanopteran species pest infestation of a plant, particularly a crop plant. The method will comprise (a) contacting the pest with an insecticidally effective amount of one or more pesticidal proteins, wherein the proteins are selected from the group consisting of: SEQ ID NOs:2, 4, 6, 8, 10, 12, 15, 18, 21, 23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99; or (b) contacting the pest with an insecticidally effective amount of one or more pesticidal proteins comprising an amino acid sequence having at least 62%, or 65%, or 70%, or 75%, or 80%, or 85%, or 90%, or 95%, or about 100% amino acid sequence identity to an amino acid sequence selected from the group consisting of: SEQ ID NOs:2, 4, 6, 8, 10, 12, 15, 18, 21, 23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99.

BRIEF DESCRIPTION OF THE FIGURES

FIG. 1 illustrates the mean number of surviving next generation *Lygus lineolaris* nymphs and adults exposed to cotton events transformed with expression cassettes used for the expression of TIC7016PL in comparison to a non-transformed control.

BRIEF DESCRIPTION OF THE SEQUENCES

SEQ ID NO:1 is a nucleic acid sequence obtained from the *Lysinibacillus sphaericus* species AG0067H07 encoding a TIC6280 pesticidal protein with a Histidine tag operably linked to the 3' end, herein referred to as TIC6280-His.

SEQ ID NO:2 is the amino acid sequence of the TIC6280-His protein.

SEQ ID NO:3 is a nucleic acid sequence obtained from the *Lysinibacillus sphaericus* species AG0067H03 encoding a TIC6281 pesticidal protein with a Histidine tag operably linked to the 3' end, herein referred to as TIC6281-His.

SEQ ID NO:4 is the amino acid sequence of the TIC6281-His protein.

SEQ ID NO:5 is a nucleic acid sequence obtained from the *Lysinibacillus sphaericus* species AG0069H08 encoding a TIC6282 pesticidal protein with a Histidine tag operably linked to the 3' end, herein referred to as TIC6282-His.

SEQ ID NO:6 is the amino acid sequence of the TIC6282-His protein.

SEQ ID NO:7 is a nucleic acid sequence obtained from the *Lysinibacillus sphaericus* species AG0025E04 encoding a TIC6283 pesticidal protein with a Histidine tag operably linked to the 3' end, herein referred to as TIC6283-His.

SEQ ID NO:8 is the amino acid sequence of the TIC6283-His protein.

SEQ ID NO:9 is a nucleic acid sequence obtained from the *Lysinibacillus sphaericus* species EGBS0420 encoding a TIC7016 pesticidal protein with a Histidine tag operably linked to the 3' end, herein referred to as TIC7016-His.

SEQ ID NO:10 is the amino acid sequence of the TIC7016-His protein.

SEQ ID NO:11 is a nucleic acid sequence obtained from the *Lysinibacillus sphaericus* species EGBS1094 encoding a TIC7017 pesticidal protein with a Histidine tag operably linked to the 3' end, herein referred to as TIC7017-His.

SEQ ID NO:12 is the amino acid sequence of the TIC7017-His protein.

SEQ ID NO:13 is a nucleic acid sequence obtained from the *Lysinibacillus sphaericus* species AG0025E04 encoding a TIC7107 pesticidal protein, which has an amino acid sequence that is 100% identical to the amino acid sequence of TIC7110, with a Histidine tag operably linked to the 3' end, herein referred to as TIC7107-His.

SEQ ID NO:14 is a nucleic acid sequence obtained from the *Lysinibacillus sphaericus* species AG0067H01 encoding a TIC7108 pesticidal protein with a Histidine tag operably linked to the 3' end, herein referred to as TIC7108-His.

SEQ ID NO:15 is the amino acid sequence of the TIC7108-His protein.

SEQ ID NO:16 is a nucleic acid sequence obtained from the *Lysinibacillus sphaericus* species AG0067H03 encoding a TIC7109 pesticidal protein, which has an amino acid sequence that is 100% identical to the amino acid sequence of TIC7110, with a Histidine tag operably linked to the 3' end, herein referred to as TIC7109-His.

SEQ ID NO:17 is a nucleic acid sequence obtained from the *Lysinibacillus sphaericus* species AG0067H07 encoding a TIC7110 pesticidal protein with a Histidine tag operably linked to the 3' end, herein referred to as TIC7110-His.

SEQ ID NO:18 is the amino acid sequence of the TIC7110-His protein.

SEQ ID NO:19 is a nucleic acid sequence obtained from the *Lysinibacillus sphaericus* species AG0069H08 encoding a TIC7111 pesticidal protein, which has an amino acid sequence that is 100% identical to the amino acid sequence of TIC7110, with a Histidine tag operably linked to the 3' end, herein referred to as TIC7111-His.

SEQ ID NO:20 is a nucleic acid sequence obtained from the *Lysinibacillus sphaericus* species AG0122F12 encoding a TIC7589 pesticidal protein with a Histidine tag operably linked to the 3' end, herein referred to as TIC7589-His.

SEQ ID NO:21 is the amino acid sequence of the TIC7589-His protein.

SEQ ID NO:22 is a nucleic acid sequence obtained from the *Lysinibacillus sphaericus* species AG0067H07 encoding a TIC6280 pesticidal protein.

SEQ ID NO:23 is the amino acid sequence of the TIC6280 protein.

SEQ ID NO:24 is a nucleic acid sequence obtained from the *Lysinibacillus sphaericus* species AG0067H03 encoding a TIC6281 pesticidal protein.

SEQ ID NO:25 is the amino acid sequence of the TIC6281 protein.

SEQ ID NO:26 is a nucleic acid sequence obtained from the *Lysinibacillus sphaericus* species AG0069H08 encoding a TIC6282 pesticidal protein.

SEQ ID NO:27 is the amino acid sequence of the TIC6282 protein.

SEQ ID NO:28 is a nucleic acid sequence obtained from the *Lysinibacillus sphaericus* species AG0025E04 encoding a TIC6283 pesticidal protein.

SEQ ID NO:29 is the amino acid sequence of the TIC6283 protein.

SEQ ID NO:30 is a nucleic acid sequence obtained from the *Lysinibacillus sphaericus* species EGBS0420 encoding a TIC7016 pesticidal protein.

SEQ ID NO:31 is the amino acid sequence of the TIC7016 protein.

SEQ ID NO:32 is a nucleic acid sequence obtained from the *Lysinibacillus sphaericus* species EGBS1094 encoding a TIC7017 pesticidal protein.

SEQ ID NO:33 is the amino acid sequence of the TIC7017 protein.

SEQ ID NO:34 is a nucleic acid sequence obtained from the *Lysinibacillus sphaericus* species AG0025E04 encoding a TIC7107 pesticidal protein, which has an amino acid sequence that is 100% identical to the amino acid sequence of TIC7110.

SEQ ID NO:35 is a nucleic acid sequence obtained from the *Lysinibacillus sphaericus* species AG0067H01 encoding a TIC7108 pesticidal protein.

SEQ ID NO:36 is the amino acid sequence of the TIC7108 protein.

SEQ ID NO:37 is a nucleic acid sequence obtained from the *Lysinibacillus sphaericus* species AG0067H03 encoding a TIC7109 pesticidal protein which has an amino acid sequence that is 100% identical to the amino acid sequence of TIC7110.

SEQ ID NO:38 is a nucleic acid sequence obtained from the *Lysinibacillus sphaericus* species AG0067H07 encoding a TIC7110 pesticidal protein.

SEQ ID NO:39 is the amino acid sequence of the TIC7110 protein.

SEQ ID NO:40 is a nucleic acid sequence obtained from the *Lysinibacillus sphaericus* species AG0069H08 encoding a TIC7111 pesticidal protein, which has an amino acid sequence that is 100% identical to the amino acid sequence of TIC7110.

SEQ ID NO:41 is a nucleic acid sequence obtained from the *Lysinibacillus sphaericus* species AG0122F12 encoding a TIC7589 pesticidal protein.

SEQ ID NO:42 is the amino acid sequence of the TIC7589 protein.

SEQ ID NO:43 is a synthetic coding sequence encoding a TIC6280 pesticidal protein designed for expression in a plant cell.

SEQ ID NO:44 is a synthetic coding sequence encoding a TIC6282 pesticidal protein designed for expression in a plant cell.

SEQ ID NO:45 is a synthetic coding sequence encoding a TIC6283 pesticidal protein designed for expression in a plant cell.

SEQ ID NO:46 is a synthetic coding sequence encoding a TIC7016PL pesticidal protein designed for expression in a plant cell, wherein an additional codon encoding an alanine residue is inserted immediately following the initiating methionine codon.

SEQ ID NO:47 is amino acid sequence of TIC7016PL, wherein an additional alanine residue is inserted immediately following the initiating methionine.

SEQ ID NO:48 is a synthetic coding sequence encoding a TIC7017PL pesticidal protein designed for expression in a plant cell, wherein an additional codon encoding an alanine residue is inserted immediately following the initiating methionine codon.

SEQ ID NO:49 is amino acid sequence of TIC7017PL, wherein an additional alanine residue is inserted immediately following the initiating methionine.

SEQ ID NO:50 is a synthetic coding sequence encoding a TIC7108PL pesticidal protein designed for expression in a plant cell, wherein an additional codon encoding an alanine residue is inserted immediately following the initiating methionine codon.

SEQ ID NO:51 is amino acid sequence of TIC7108PL, wherein an additional alanine residue is inserted immediately following the initiating methionine.

SEQ ID NO:52 is a synthetic coding sequence encoding a TIC7110PL pesticidal protein designed for expression in a plant cell, wherein an additional codon encoding an alanine residue is inserted immediately following the initiating methionine codon.

SEQ ID NO:53 is amino acid sequence of TIC7110PL, wherein an additional alanine residue is inserted immediately following the initiating methionine.

SEQ ID NO:54 is a synthetic sequence encoding a TIC7110/TIC6280 fusion toxin protein, TIC7110-TIC6280F1, wherein the two toxin protein encoding sequences are contiguous and in frame.

SEQ ID NO:55 is an amino acid sequence of a TIC7110/TIC6280 fusion toxin protein, TIC7110-TIC6280F1, wherein the two toxin protein amino acid sequences are contiguous.

SEQ ID NO:56 is a synthetic sequence encoding a TIC7110/TIC6280 fusion toxin protein, TIC7110-TIC6280F2, wherein a cleavable linker sequence (Linker 1) is operably linked and in frame between the two toxin protein encoding sequences.

SEQ ID NO:57 is an amino acid sequence of a TIC7110/TIC6280 fusion toxin protein, TIC7110-TIC6280F2, wherein a cleavable linker peptide sequence (Linker 1) is inserted between the two toxin protein amino acid sequences.

SEQ ID NO:58 is a synthetic sequence encoding a TIC7110/TIC6280 fusion toxin protein, TIC7110-TIC6280F3, wherein a flexible linker sequence (Linker 2) is operably linked and in frame between the two toxin protein encoding sequences.

SEQ ID NO:59 is an amino acid sequence of a TIC7110/TIC6280 fusion toxin protein, TIC7110-TIC6280F3, wherein a flexible linker peptide sequence (Linker 2) is inserted between the two toxin protein amino acid sequences.

SEQ ID NO:60 is a synthetic sequence encoding a TIC7111/TIC6282 fusion toxin protein, TIC7111-TIC6282F1, wherein the two toxin protein encoding sequences are contiguous and in frame.

SEQ ID NO:61 is an amino acid sequence of a TIC7111/TIC6282 fusion toxin protein, TIC7111-TIC6282F1, wherein the two toxin protein amino acid sequences are contiguous.

SEQ ID NO:62 is a synthetic sequence encoding a TIC7111/TIC6282 fusion toxin protein, TIC7111-TIC6282F2, wherein a cleavable linker sequence (Linker 1) is operably linked and in frame between the two toxin protein encoding sequences.

SEQ ID NO:63 is an amino acid sequence of a TIC7111/TIC6282 fusion toxin protein, TIC7111-TIC6282F2, wherein a cleavable linker peptide sequence (Linker 1) is inserted between the two toxin protein amino acid sequences.

SEQ ID NO:64 is a synthetic sequence encoding a TIC7111/TIC6282 fusion toxin protein, TIC7111-TIC6282F3, wherein a flexible linker sequence (Linker 2) is operably linked and in frame between the two toxin protein encoding sequences.

SEQ ID NO:65 is an amino acid sequence of a TIC7111/TIC6282 fusion toxin protein, TIC7111-TIC6282F3, wherein a flexible linker peptide sequence (Linker 2) is inserted between the two toxin protein amino acid sequences.

SEQ ID NO:66 is a synthetic sequence encoding a TIC7109/TIC6281 fusion toxin protein, TIC7109-TIC6281F1, wherein the two toxin protein encoding sequences are contiguous and in frame.

SEQ ID NO:67 is an amino acid sequence of a TIC7109/TIC6281 fusion toxin protein, TIC7109-TIC6281F1, wherein the two toxin protein amino acid sequences are contiguous.

SEQ ID NO:68 is a synthetic sequence encoding a TIC7109/TIC6281 fusion toxin protein, TIC7109-TIC6281F2, wherein a cleavable linker sequence (Linker 1) is operably linked and in frame between the two toxin protein encoding sequences.

SEQ ID NO:69 is an amino acid sequence of a TIC7109/TIC6281 fusion toxin protein, TIC7109-TIC6281F2, wherein a cleavable linker peptide sequence (Linker 1) is inserted between the two toxin protein amino acid sequences.

SEQ ID NO:70 is a synthetic sequence encoding a TIC7109/TIC6281 fusion toxin protein, TIC7109-TIC6281F3, wherein a flexible linker sequence (Linker 2) is operably linked and in frame between the two toxin protein encoding sequences.

SEQ ID NO:71 is an amino acid sequence of a TIC7109/TIC6281 fusion toxin protein, TIC7109-TIC6281F3, wherein a flexible linker peptide sequence (Linker 2) is inserted between the two toxin protein amino acid sequences.

SEQ ID NO:72 is a synthetic DNA sequence encoding a cleavable linker, Linker 1 that is operably linked and in frame between two toxin coding sequences.

SEQ ID NO:73 is the amino acid sequence of the cleavable linker, Linker 1.

SEQ ID NO:74 is a synthetic DNA sequence encoding a flexible linker, Linker 2 that is operably linked and in frame between two toxin coding sequences.

SEQ ID NO:75 is the amino acid sequence of the flexible linker, Linker 2.

SEQ ID NO:76 is a synthetic sequence of an operon, TIC7110-TIC6280operon, comprising the coding sequence of TIC7110 followed by the coding sequence of TIC6280, wherein an operon linker (Operon_Linker) is inserted between the two coding sequences.

SEQ ID NO:77 is a synthetic sequence of an operon, TIC7111-TIC6282operon, comprising the coding sequence of TIC7111 followed by the coding sequence of TIC6282, wherein an operon linker (Operon_Linker) is inserted between the two coding sequences.

SEQ ID NO:78 is a synthetic sequence of an operon, TIC7109-TIC6281operon, comprising the coding sequence of TIC7109 followed by the coding sequence of TIC6281, wherein an operon linker (Operon_Linker) is inserted between the two coding sequences.

SEQ ID NO:79 is a synthetic sequence of a linker, Operon_Linker which comprises at the 5' end a stop codon to terminate translation of a first toxin gene and is inserted between two toxin protein coding sequences to permit expression of both toxin proteins in the bacterial host.

SEQ ID NO:80 is a nucleic acid sequence obtained from a plate-scrape metagenome designated MTG000070 encoding a TIC8808 pesticidal protein with a Histidine tag operably linked to the 3' end, herein referred to as TIC8808-His.

SEQ ID NO:81 is the amino acid sequence of the TIC8808-His protein.

SEQ ID NO:82 is a nucleic acid sequence obtained from a plate-scrape metagenome designated MTG000415, encoding a TIC9480 pesticidal protein with a Histidine tag operably linked to the 3' end, herein referred to as TIC9480-His.

SEQ ID NO:83 is the amino acid sequence of the TIC9480-His protein.

SEQ ID NO:84 is a nucleic acid sequence obtained from a plate-scrape metagenome designated MTG000199, encoding a TIC9257 pesticidal protein with a Histidine tag operably linked to the 3' end, herein referred to as TIC9257-His.

SEQ ID NO:85 is the amino acid sequence of the TIC9257-His protein.

SEQ ID NO:86 is a nucleic acid sequence obtained from a plate-scrape metagenome designated MTG000120, encoding a TIC9258 pesticidal protein with a Histidine tag operably linked to the 3' end, herein referred to as TIC9258-His.

SEQ ID NO:87 is the amino acid sequence of the TIC9258-His protein.

SEQ ID NO:88 is a nucleic acid sequence obtained from a plate-scrape metagenome designated MTG000184, encoding a TIC9259 pesticidal protein with a Histidine tag operably linked to the 3' end, herein referred to as TIC9259-His.

SEQ ID NO:89 is the amino acid sequence of the TIC9259-His protein.

SEQ ID NO:90 is a nucleic acid sequence obtained from a plate-scrape metagenome designated MTG000184, encoding a TIC8808 pesticidal protein.

SEQ ID NO:91 is the amino acid sequence of the TIC8808 protein.

SEQ ID NO:92 is a nucleic acid sequence obtained from a plate-scrape metagenome designated MTG000415, encoding a TIC9480 pesticidal protein.

SEQ ID NO:93 is the amino acid sequence of the TIC9480 protein.

SEQ ID NO:94 is a nucleic acid sequence obtained from a plate-scrape metagenome designated MTG000199, encoding a TIC9257 pesticidal protein.

SEQ ID NO:95 is the amino acid sequence of the TIC9257 protein.

SEQ ID NO:96 is a nucleic acid sequence obtained from a plate-scrape metagenome designated MTG000120, encoding a TIC9258 pesticidal protein.

SEQ ID NO:97 is the amino acid sequence of the TIC9258 protein.

SEQ ID NO:98 is a nucleic acid sequence obtained from a plate-scrape metagenome designated MTG000184, encoding a TIC9259 pesticidal protein.

SEQ ID NO:99 is the amino acid sequence of the TIC9259 protein.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal protein classes exemplified by the TIC6280 protein and TIC6280-related toxin protein members, and the TIC7016 protein and TIC7016-related toxin protein members are disclosed herein, and addresses each of these needs, particularly against a broad spectrum of Coleopteran, Lepidopteran, Hemipteran, and Thysanopteran insect pests, and more particularly against Western Corn Rootworm pest species.

Reference in this application to TIC6280, "TIC6280 protein", "TIC6280 protein toxin", "TIC6280 toxin protein", "TIC6280 pesticidal protein", "TIC6280-related toxins", or "TIC6280-related toxin proteins", and the like, refer to any novel pesticidal protein or insect inhibitory protein, that comprises, that consists of, that is substantially homologous to, that is similar to, or that is derived from any pesticidal protein or insect inhibitory protein sequences of TIC6280 (SEQ ID NO:23), TIC6281 (SEQ ID NO:25), TIC6282 (SEQ ID NO:27), TIC6283 (SEQ ID NO:29), TIC8808 (SEQ ID NO:91), TIC9480 (SEQ ID NO:93), and TIC9257 (SEQ ID NO:95) and pesticidal or insect inhibitory segments thereof, or combinations thereof, that confer activity against Coleopteran pests, Lepidopteran pests, Hemipteran pests, and/or Thysanopteran pests, including any protein exhibiting pesticidal or insect inhibitory activity if alignment of such protein with TIC6280 results in amino acid sequence identity of any fraction percentage from about 62 to about 100 percent.

Reference in this application to TIC7016, "TIC7016 protein", "TIC7016 protein toxin", "TIC7016 toxin protein", "TIC7016 pesticidal protein", "TIC7016-related toxins", or "TIC7016-related toxin protein", and the like, refer to any novel pesticidal protein or insect inhibitory protein, that comprises, that consists of, that is substantially homologous to, that is similar to, or that is derived from any pesticidal protein or insect inhibitory protein sequences of TIC7016 (SEQ ID NO:31), TIC7017 (SEQ ID NO:33), TIC7108 (SEQ ID NO:36), TIC7110 (SEQ ID NO:39), TIC7589 (SEQ ID NO:42), TIC9258 (SEQ ID NO:97), and TIC9259 (SEQ ID NO:99), and pesticidal or insect inhibitory segments thereof, or combinations thereof, that confer activity against Coleopteran pests, Lepidopteran pests, Hemipteran, and/or Thysanopteran pests, including any protein exhibiting pesticidal or insect inhibitory activity if alignment of such protein with TIC7016 results in amino acid sequence identity of any fraction percentage from about 62 to about 100 percent.

The term "segment" or "fragment" is used in this application to describe consecutive amino acid or nucleic acid sequences that are shorter than the complete amino acid or nucleic acid sequence describing a TIC6280 protein or TIC6280-related toxin protein, or a TIC7016 protein or TIC7016-related toxin protein. A segment or fragment exhibiting insect inhibitory activity is also disclosed in this application if alignment of such segment or fragment, with the corresponding section of the TIC6280 protein set forth in SEQ ID NO:23 or TIC7016 protein set forth in SEQ ID NO:31, results in amino acid sequence identity of any fraction percentage from about 62 to about 100 percent between the segment or fragment and the corresponding section of the TIC6280 protein or TIC7016 protein, respectively.

In still further specific embodiments, a fragment of a TIC6280 protein or TIC6280-related toxin protein, or a TIC7016 protein or TIC7016-related toxin protein may be defined as exhibiting pesticidal activity possessed by the starting protein molecule from which it is derived. A fragment of a nucleic acid sequence encoding a TIC6280 protein or TIC6280-related toxin protein, or a TIC7016 protein or TIC7016-related toxin protein may be defined as encoding a protein exhibiting the pesticidal activity possessed by the protein molecule encoded by the starting nucleic acid sequence from which it is derived. A fragment or variant described herein may further comprise a domain identified herein which is responsible for the pesticidal activity of a protein.

In specific embodiments, fragments of a TIC6280 protein or TIC6280-related toxin protein, or a TIC7016 protein or TIC7016-related toxin protein are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, at least about 1000, at least about 1100, at least about 1150, or at least about 1175 contiguous amino acids, or longer, of a TIC6280 protein or TIC6280-related toxin protein, or a TIC7016 protein or TIC7016-related toxin protein having pesticidal activity as disclosed herein. In certain embodiments, the invention provides fragments of any one of TIC6280 (SEQ ID NO:23), TIC6281 (SEQ ID NO:25), TIC6282 (SEQ ID NO:27), TIC6283 (SEQ ID NO:29), TIC8808 (SEQ ID NO:91), TIC9480 (SEQ ID NO:93), and TIC9257 (SEQ ID NO:95), or of TIC7016 (SEQ ID NO:31), TIC7017 (SEQ ID NO:33), TIC7108 (SEQ ID NO:36), TIC7110 (SEQ ID NO:39), TIC7589 (SEQ ID NO:42), TIC9258 (SEQ ID NO:97), and TIC9259 (SEQ ID NO:99) and having the activity of the full length sequence. Methods for producing such fragments from a starting molecule are known in the art.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of a TIC6280 protein or TIC6280-related toxin protein, or a TIC7016 protein or TIC7016-related toxin protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera, or Coleoptera, or Hemiptera, or Thysanoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopteran, Coleopteran, Hemipteran, or Thysanopteran pest species.

It is intended that reference to a pest, particularly a pest of a crop plant, means insect pests of crop plants, particularly those that are controlled by a TIC6280 protein or TIC6280-related toxin protein, or a TIC7016 protein or TIC7016-related toxin protein. Reference to a pest can also include Homopteran insect pests of plants, as well as nematodes and fungi when toxic agents targeting these pests are co-localized or present together with a TIC6280-related toxin protein or TIC7016-related toxin protein, or a protein that is 62 to about 100 percent identical to TIC6280 or TIC7016 toxin proteins, respectively.

The TIC6280 and TIC7016-related toxin proteins exhibit insecticidal activity towards insect pests from the Coleopteran and Lepidopteran insect species, including adults, pupae, larvae, and neonates, as well as Hemipteran insect species, including adults and nymphs, and Thysanopteran insect species, including adults, pupae, prepupae, and larvae.

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera exempta*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (Cnaphalocrocis *medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leafminer (*Tuta absoluta*).

The insects of the order Coleoptera include, but are not limited to, *Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp, particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm, BZR), *Diabrotica undecimpunctata howardii* (Southern Corn Rootworm, SCR) and a Brazilian Corn Rootworm complex (BCR) consisting of *Diabrotica viridula* and *Diabrotica speciosa*).

The insects of Hemiptera include but are not limited to, *Chinavia hilaris*, *Chinavia marginata*, *Chinavia pensylvanica*, *Chlorochroa granulose*, *Chlorochroa kanei*, *Chlorochroa ligata*, *Chlorochroa lineate*, *Chlorochroa opuntiae*, *Chlorochroa persimilis*, *Chlorochroa rossiana*, *Chlorochroa sayi*, *Chlorochroa uhleri*, *Chlorochroa belfragii*, *Chlorochroa faceta*, *Chlorochroa osborni*, *Chlorochroa saucia*, *Chlorochroa senilis*, *Nezara viridula*, *Edessa meditabunda*, *Edessa bifida*, *Edessa florida*, *Euschistus heros*, *Euschistus acuminatus*, *Euschistus biformis*, *Euschistus conspersus*, *Euschistus crenator*, *Euschistus egglestoni*, *Euschistus ictericus*, *Euschistus inflatus*, *Euschistus latimarginatus*, *Euschistus obscures*, *Euschistus politus*, *Euschistus quadrator*, *Euschistus sevus*, *Euschistus strenuous*, *Euschistus tristigmus*, *Euschistus variolarius Halyomorpha halys*, *Thyanta accerra*, *Thyanta calceata*, *Thyanta custator*, *Thyanta pallidovirens*, *Thyanta perditor*, *Thyanta maculate*, *Thyanta pseudocasta Dichelops melacanthus*, *Dichelops avilapiresi*, *Dichelops bicolor*, *Dichelops dimidatus*, *Dichelops furcatus*, *Dichelops furcifrons*, *Dichelops lobatus*, *Dichelops miriamae*, *Dichelops nigrum*, *Dichelops peruanus*, *Dichelops phoenix*, *Dichelops saltensis*, *Piezodorus guildinni*, *Piezodorus lituratus Megacopta cribraria*, *Lygus hesperus*, *Lygus lineolaris*, and *Pseudatomoscelis seriatus*.

The insects of Thysanoptera include but are not limited to, Tobacco Thrips (*Frankliniella fusca*), Flower Thrips (*Frankliniella tritici*), Western Flower Thrips (*Frankliniella occidentalis*), and Soybean Thrips (*Sericothrips variabilis*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in Table 1, open reading frames (ORF) encoding TIC6280-related and TIC7016-related toxin proteins were discovered in DNA obtained from several different *Lysinibacillus sphaericus* strains or plate-scrape metagenomes (MTG).

TABLE 1

Open Reading Frames Encoding TIC6280 and TIC7016-related Toxin Proteins Obtained from *Lysinibacillus sphaericus* Strains.

| Protein Encoded by Nucleic Acid Sequence | Nucleic Acid Sequence SEQ ID NO | Amino Acid Sequence SEQ ID NO | *Lysinibacillus sphaericus* strain |
|---|---|---|---|
| TIC6280 | (SEQ ID NO: 22) | (SEQ ID NO: 23) | AG0067H07 |
| TIC6281 | (SEQ ID NO: 24) | (SEQ ID NO: 25) | AG0067H03 |
| TIC6282 | (SEQ ID NO: 26) | (SEQ ID NO: 27) | AG0069H08 |
| TIC6283 | (SEQ ID NO: 28) | (SEQ ID NO: 29) | AG0025E04 |
| TIC8808 | (SEQ ID NO: 90) | (SEQ ID NO: 91) | MTG000070 |
| TIC9480 | (SEQ ID NO: 92) | (SEQ ID NO: 93) | MTG000415 |
| TIC9257 | (SEQ ID NO: 94) | (SEQ ID NO: 95) | MTG000199 |
| TIC7016 | (SEQ ID NO: 30) | (SEQ ID NO: 31) | EGBS0420 |
| TIC7017 | (SEQ ID NO: 32) | (SEQ ID NO: 33) | EGBS1094 |
| TIC7107 | (SEQ ID NO: 34) | (SEQ ID NO: 39) | AG0025E04 |
| TIC7108 | (SEQ ID NO: 35) | (SEQ ID NO: 36) | AG0067H01 |
| TIC7109 | (SEQ ID NO: 37) | (SEQ ID NO: 39) | AG0067H03 |
| TIC7110 | (SEQ ID NO: 38) | (SEQ ID NO: 39) | AG0067H07 |
| TIC7111 | (SEQ ID NO: 40) | (SEQ ID NO: 39) | AG0069H08 |
| TIC7589 | (SEQ ID NO: 41) | (SEQ ID NO: 42) | AG0122F12 |
| TIC9258 | (SEQ ID NO: 96) | (SEQ ID NO: 97) | MTG000120 |
| TIC9259 | (SEQ ID NO: 98) | (SEQ ID NO: 99) | MTG000184 |

The respective coding sequences were cloned and expressed in microbial host cells to produce protein used in bioassays. As noted in the Table, the nucleic acid sequences encoding TIC7107, TIC7109, TIC7110, and TIC7111 encode the same amino acid sequence, herein referenced as TIC7110, and differ from each other by 1 to 6 nucleotides.

For expression in plant cells, the TIC6280-related toxin proteins and the TIC7016-related toxin proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting the TIC6280 protein or TIC6280-related toxin protein, or the TIC7016 protein or TIC7016-related toxin protein to the chloroplast, a sequence encoding a chloroplast transit peptide is placed 5' in operable linkage and in frame to a synthetic coding sequence encoding the TIC6280 protein or TIC6280-related toxin protein, or the TIC7016 protein or TIC7016-related toxin protein that has been designed for optimal expression in plant cells.

It is contemplated that additional toxin protein sequences related to the TIC6280 toxin proteins and the TIC7016 toxin proteins can be created by using the naturally occurring amino acid sequences of the TIC6280 toxin proteins and the TIC7016 toxin proteins to create novel proteins and with novel properties. The TIC6280 and TIC7016 toxin proteins can be aligned with other proteins similar to TIC6280 or TIC7016 to combine differences at the amino acid sequence level into novel amino acid sequence variants and making appropriate changes to the recombinant nucleic acid sequence encoding the variants.

This disclosure further contemplates that improved variants of the TIC6280 and TIC7016 protein toxin classes can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of the TIC6280 and TIC7016 toxin protein classes, or protein variants thereof can be truncated forms wherein one or more amino acids are deleted from the N-terminal end, C-terminal end, the middle of the protein, or combinations thereof with insect inhibitory activity. These fragments can be naturally occurring or synthetic variants of TIC6280 toxin proteins or TIC7016 toxin proteins, or derived protein variants, but should retain the insect inhibitory activity of TIC6280 or TIC7016. Truncated N-terminal or C-terminal deletion variants include, but are not limited to, TIC6280 proteins, TIC7016 proteins, or protein variants thereof that lack amino acid residues from either the N-terminus and/or the C-terminus. A fragment or variant described herein may further comprise a domain identified herein which is responsible for the pesticidal activity of a protein.

Proteins that resemble the TIC6280 and TIC7016 protein toxin classes can be identified by comparison to each other using various computer based algorithms known in the art. For example, amino acid sequence identities of proteins related to the TIC6280 and TIC7016 protein toxin classes can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran, or Coleopteran, or Hemipteran, or Thysanopteran insect species is related to the TIC6280 or TIC7016 protein toxin class if the protein is used in a query, e.g., in a Clustal W alignment, and at least one of the proteins of the present invention as set forth as TIC6280 or TIC7016 are identified as hits in such alignment in which the query protein exhibits at least 62% to about 100% amino acid identity along the length of the query protein, that is about 62%, 63%, 64%, 65%, 66%, 67%, 68%, 69%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100%, or any fraction percentage in this range.

Exemplary proteins of the TIC6280 toxin protein class—TIC6280 (SEQ ID NO:23), TIC6281 (SEQ ID NO:25), TIC6282 (SEQ ID NO:27), TIC6283 (SEQ ID NO:29), TIC8808 (SEQ ID NO:91), TIC9480 (SEQ ID NO:93), and TIC9257 (SEQ ID NO:95)—were aligned with each other using a Clustal W algorithm. A pair-wise matrix of percent amino acid sequence identities for each pair was created, as reported in Table 2.

TABLE 2

Pair-wise matrix display of exemplary TIC6280-related toxin proteins.

| Toxin | TIC6280 | TIC6281 | TIC6282 | TIC6283 | TIC8808 | TIC9480 | TIC9527 |
|---|---|---|---|---|---|---|---|
| TIC6280 | — | 99.3 (286) | 99.3 (286) | 99.3 (286) | 92.7 (267) | 87.5 (252) | 87.5 (252) |
| TIC6281 | 99.3 (286) | — | 98.6 (284) | 97.9 (282) | 92 (265) | 86.8 (250) | 86.8 (250) |
| TIC6282 | 99.3 (286) | 98.6 (284) | — | 99.3 (286) | 92.7 (267) | 87.5 (252) | 87.5 (252) |
| TIC6283 | 98.6 (284) | 97.9 (282) | 99.3 (286) | — | 92.4 (266) | 87.2 (251) | 87.2 (251) |
| TIC8808 | 92.7 (267) | 92 (265) | 92.7 (267) | 92.4 (266) | — | 93.8 (270) | 93.8 (270) |
| TIC9480 | 83.2 (252) | 82.5 (250) | 83.2 (252) | 82.8 (251) | 89.1 (270) | — | 99.7 (302) |
| TIC9257 | 83.2 (252) | 82.5 (250) | 83.2 (252) | 82.8 (251) | 89.1 (270) | 99.7 (302) | — |

Table Description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

Exemplary proteins of the TIC7016 toxin protein class—TIC7016 (SEQ ID NO:31), TIC7017 (SEQ ID NO:33), TIC7108 (SEQ ID NO:36), TIC7110 (SEQ ID NO:39), TIC7589 (SEQ ID NO:42), TIC9258 (SEQ ID NO:97), and TIC9259 (SEQ ID NO:99)— were aligned with each other using a Clustal W algorithm. A pair-wise matrix of percent amino acid sequence identities for each pair was created, as reported in Table 3. The number of identical amino acids between two sequences is indicated in parenthesis.

TABLE 3

Pair-wise matrix display of exemplary TIC7016-related toxin proteins.

| Toxin | TIC7016 | TIC9259 | TIC9258 | TIC7017 | TIC7108 | TIC7110 | TIC7589 |
|---|---|---|---|---|---|---|---|
| TIC7016 | — | 99.6 (273) | 99.3 (272) | 98.9 (271) | 96.4 (264) | 96.7 (265) | 62.8 (172) |
| TIC9259 | 99.6 (273) | — | 98.9 (271) | 98.5 (270) | 96 (263) | 96.4 (264) | 62.4 (171) |
| TIC9258 | 99.3 (272) | 98.9 (271) | — | 98.2 (269) | 95.6 (262) | 96 (263) | 63.5 (174) |
| TIC7017 | 98.9 (271) | 98.5 (270) | 98.2 (269) | — | 95.6 (262) | 96 (263) | 63.1 (173) |
| TIC7108 | 96.4 (264) | 96 (263) | 95.6 (262) | 95.6 (262) | — | 99.6 (273) | 62 (170) |
| TIC7110 | 96.7 (265) | 96.4 (264) | 96 (263) | 96 (263) | 99.6 (273) | — | 62.4 (171) |
| TIC7589 | 62.5 (172) | 62.2 (171) | 63.3 (174) | 62.9 (173) | 61.8 (170) | 62.2 (171) | — |

Table Description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

The *Lysinibacillus sphaericus* coding sequences encoding TIC7107 (SEQ ID NO:34), TIC7109 (SEQ ID NO:37), and TIC7111 (SEQ ID NO:40) encode an amino acid sequence that is 100% identical to the amino acid sequence of TIC7110 (SEQ ID NO:39). Each of the coding sequences differs from 1 to 6 nucleotides, depending upon which two sequences are compared. The TIC7107 (SEQ ID NO:34), TIC7109 (SEQ ID NO:37), TIC7110 (SEQ ID NO:38), and TIC7111 (SEQ ID NO:40) coding sequences were aligned with each other using a Clustal W algorithm. A pair-wise matrix of percent nucleic acid sequence identities for each pair was created, as reported in Table 4. The number of identical nucleic acids between two sequences is indicated in parenthesis.

TABLE 4

| Pair-wise matrix display of the TIC7107, TIC7109, TIC7110, and TIC7111 *Lysinibacillus sphaericus* coding sequences. | | | | |
|---|---|---|---|---|
| Toxin | TIC7107 | TIC7111 | TIC7109 | TIC7110 |
| TIC7107 | — | 99.6% (822) | 99.4% (820) | 99.3% (819) |
| TIC7111 | 99.6% (822) | — | 99.8% (823) | 99.6% (822) |
| TIC7109 | 99.4% (820) | 99.8% (823) | — | 99.9% (824) |
| TIC7110 | 99.3% (819) | 99.6% (822) | 99.9% (824) | — |

Table Description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

In addition to percent identity, the proteins of the TIC6280 protein toxin class can also be related by primary structure (conserved amino acid motifs), by length (about 288 amino acids) and by other characteristics. Characteristics of the TIC6280 toxin protein class are reported in Table 5.

TABLE 5

Characteristics of the TIC6280 toxin protein class.

| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
|---|---|---|---|---|---|---|---|---|
| TIC6280 | 32370.15 | 288 | 4.7933 | −7.0 | 31 | 36 | 128 | 160 |
| TIC6281 | 32342.13 | 288 | 4.8894 | −6.0 | 31 | 35 | 128 | 160 |
| TIC6282 | 32370.15 | 288 | 4.7987 | −7.0 | 31 | 36 | 128 | 160 |
| TIC6283 | 32384.13 | 288 | 4.7073 | −8.0 | 30 | 36 | 128 | 160 |
| TIC8808 | 32463.27 | 288 | 5.1723 | −5.5 | 34 | 36 | 126 | 162 |
| TIC9480 | 34397.08 | 303 | 6.6320 | 0.5 | 39 | 35 | 140 | 163 |
| TIC9527 | 34411.11 | 303 | 6.6323 | 0.5 | 39 | 35 | 140 | 163 |

The proteins of the TIC7016 toxin protein class can also be related by primary structure (conserved amino acid motifs), by length (about 274 amino acids) and by other characteristics. Characteristics of the TIC7016 toxin protein class are reported in Table 6.

TABLE 6

Characteristics of the TIC7016 toxin protein class.

| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
|---|---|---|---|---|---|---|---|---|
| TIC7016 | 30426.30 | 274 | 5.3772 | −3.5 | 31 | 32 | 128 | 146 |
| TIC7017 | 30383.28 | 274 | 5.3772 | −3.5 | 31 | 32 | 129 | 145 |
| TIC7108 | 30531.49 | 274 | 5.3772 | −3.5 | 31 | 32 | 130 | 144 |
| TIC7110 | 30519.43 | 274 | 5.3772 | −3.5 | 31 | 32 | 129 | 145 |
| TIC7589 | 30798.65 | 275 | 5.9612 | −2.0 | 34 | 33 | 124 | 151 |
| TIC9258 | 30428.28 | 274 | 5.3772 | −3.5 | 31 | 32 | 127 | 147 |
| TIC9259 | 30357.19 | 274 | 5.1504 | −4.5 | 30 | 32 | 128 | 146 |

As described further in the Examples of this application, synthetic nucleic acid molecule sequences encoding TIC6280, TIC6282, TIC6283, TIC7016PL, TIC7017PL, TIC7108PL, and TIC7110PL were designed for use in plants. Exemplary recombinant nucleic acid molecule sequences that were designed for use in plants encoding the TIC6280, TIC6282, TIC6283, TIC7016PL, TIC7017PL, TIC7108PL, and TIC7110PL proteins is set forth as SEQ ID NOs:43, 44, 45, 46, 48, 50, and 52, respectively. The TIC7016PL, TIC7017PL, TIC7018PL, TIC7110PL proteins have an additional alanine amino acid immediately following the initiating methionine. The additional alanine residue insertions are believed to improve expression of the protein in planta. Other members of the TIC6280 and the TIC7016 protein toxin class can be designed for use in plants.

In addition, as described in the Examples of this application, TIC6280, TIC6282, TIC6283, TIC7016, TIC7017, TIC7108, and TIC7110 exhibit insecticidal activity towards Coleopteran and Lepidopteran insect species, including adults, pupae, larvae and neonates, as well as Hemipteran insect species, including nymphs and adults.

Expression cassettes and vectors containing these recombinant nucleic acid molecule sequences can be constructed and introduced into corn, soybean, cotton or other plant cells in accordance with transformation methods and techniques known in the art. Transformed cells can be regenerated into transformed plants that are observed to be expressing insect inhibitory TIC6280, TIC6282, TIC6283, TIC7016PL, TIC7017PL, TIC7108PL, or TIC7110PL protein. To test pesticidal activity, bioassays are performed in the presence of Lepidopteran pest larvae using plant leaf disks obtained from the transformed plants as described in the example below. To test pesticidal activity against Coleopteran pests, transformed plants of the $R_0$ and $F_1$ generation are used in a root worm assay as described in the example below. To test pesticidal activity against Hemipteran pests, pods, corn ears or leaves of transformed plants are used in assay, either from tissue removed from the plant or remaining on the plant as described in the examples below.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing. Similarly, a "recombinant protein molecule" is a protein molecule comprising a combination of amino acids that would not naturally occur together without human intervention. For example, a recombinant protein molecule may be a protein molecule that is comprised of at least two amino acid molecules heterologous with respect to each other, a protein molecule that comprises an amino acid sequence that deviates from amino acid sequences that exist in nature, or a protein molecule that is expressed in a host cell as a result of genetic transformation of the host cell or by gene editing of the host cell genome.

Recombinant nucleic acid molecule compositions that encode proteins from the TIC6280 and TIC7016 toxin protein classes are contemplated. For example, proteins from the TIC6280 and TIC7016 toxin protein classes can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the encoding sequences for proteins from the TIC6280 and TIC7016 toxin protein classes for expression of the protein in plants or a Bt-functional promoter operably linked encoding sequences for proteins from the TIC6280 and TIC7016 toxin protein classes for expression of the protein in a Bt bacterium or other *Bacillus* species. Other elements can be operably linked to the protein encoding sequences from the TIC6280 and TIC7016 toxin protein classes including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NOs:1, 3, 5, 7, 9, 11, 13, 14, 16, 17, 19, 20, 22, 24, 26, 28, 30, 32, 34, 35, 37, 38, 40, 41, 43, 44, 45, 46, 48, 50, 52, 54, 56, 58, 60, 62, 64, 66, 68, 70, 80, 82, 84, 86, 88, 90, 92, 94, 96, and 98 that encodes the polypeptide or protein having the amino acid sequence as set forth in SEQ ID NOs:2, 4, 6, 8, 10, 12, 15, 18, 21, 23, 25, 27, 29, 31, 33, 36, 39, 42, 47, 49, 51, 53, 55, 57, 59, 61, 63, 65, 67, 69, 71, 81, 83, 85, 87, 89, 91, 93, 95, 97, and 99. A heterologous promoter can also be operably linked to synthetic DNA coding sequences encoding a plastid targeted or untargeted protein from the TIC6280 or TIC7016 toxin protein classes. The codons of a recombinant nucleic acid molecule encoding for protein disclosed herein can be substituted by synonymous codons (known in the art as a silent substitution). Naturally occurring silent mutations are demonstrated in the coding sequences encoding TIC7107 (SEQ ID NO:34), TIC7109 (SEQ ID NO:37), TIC7110 (SEQ ID NO:38), and TIC7111 (SEQ ID NO:40), wherein each coding sequence encodes the same protein amino acid sequence, TIC7110 (SEQ ID NO:39).

A recombinant DNA construct comprising an encoding sequence for a protein from the TIC6280 or TIC7016 toxin protein classes can further comprise a region of DNA that encodes for one or more insect inhibitory agents which can be configured to concomitantly express or co-express with a DNA sequence encoding a protein from the TIC6280 or TIC7016 toxin protein classes, a protein different from a protein from the TIC6280 or TIC7016 toxin protein classes, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the TIC6280 and TIC7016 toxin protein classes are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules.

Recombinant nucleic acid molecules or recombinant DNA constructs comprising an encoding sequence from the TIC6280 or TIC7016 toxin protein classes can be delivered to host cells by vectors, e.g., a plasmid, baculovirus, synthetic chromosome, virion, cosmid, phagemid, phage, or viral vector. Such vectors can be used to achieve stable or transient expression of a protein encoding sequence from the TIC6280 and TIC7016 toxin protein classes in a host cell, or subsequent expression of the encoded polypeptide. An exogenous recombinant polynucleotide or recombinant DNA construct that comprises a protein encoding sequence from the TIC6280 and TIC7016 toxin protein class that is introduced into a host cell is referred herein as a "transgene."

Transgenic bacteria, transgenic plant cells, transgenic plants, and transgenic plant parts that contain a recombinant polynucleotide that expresses any one or more of the proteins from the TIC6280 or TIC7016 toxin protein classes are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera-, Lepidoptera-, Hemiptera- or Thysanoptera-inhibitory amounts of a protein from the TIC6280 or TIC7016 toxin protein class are provided. Such plants can be made by introducing a recombinant polynucleotide that encodes any of the proteins provided in this application into a plant cell, and selecting a plant derived from said plant cell that expresses an insect, Coleoptera-, Lepidoptera-, Hemiptera-, or Thysanoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a protein from the TIC6280 or TIC7016 protein toxin classes, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a protein from the TIC6280 or TIC7016 protein toxin classes.

Plants expressing a protein from the TIC6280 or TIC7016 protein toxin classes can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As further described in the Examples, sequences encoding a protein from the TIC6280 or TIC7016 protein toxin classes and sequences having a substantial percentage identity to a protein from the TIC6280 or TIC7016 protein toxin classes can be identified using methods known to those of ordinary skill in the art such as polymerase chain reaction (PCR), thermal amplification and hybridization. For example, a protein from the TIC6280 or TIC7016 protein toxin classes can be used to produce antibodies that bind specifically to related proteins, and can be used to screen for and to find other protein members that are closely related.

Furthermore, nucleotide sequences encoding a protein from the TIC6280 or TIC7016 protein toxin classes can be used as probes and primers for screening to identify other members of the class using thermal-cycle or isothermal amplification and hybridization methods. For example, oligonucleotides derived from sequences as set forth in SEQ ID NOs: 43, 44, 45, 46, 48, 50, or 52 can be used to determine the presence or absence of a TIC6280, TIC6282, TIC6283, TIC7016, TIC7017, TIC7108, or TIC7110 transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NOs:43, 44, 45, 46, 48, 50, and 52 can be used to detect a TIC6280, TIC6282, TIC6283, TIC7016, TIC7017, TIC7108, or TIC7110 transgene in commodity products derived from pooled sources where only a fraction of the commodity product is derived from a transgenic plant containing any of SEQ ID NOs:43, 44, 45, 46, 48, 50, and 52. It is further recognized that such oligonucleotides can be used to introduce nucleotide sequence variation in SEQ ID NOs:43, 44, 45, 46, 48, 50, and 52. Such "mutagenesis" oligonucleotides are useful for identification of amino acid sequence variants of a protein from the TIC6280 or TIC7016 protein toxin classes exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes under stringent hybridization conditions to the second nucleotide sequence. In such case, the second nucleotide sequence can be the nucleotide sequence selected from the group consisting of: SEQ ID NOs:1, 3, 5, 7, 9, 11, 13, 14, 16, 17, 19, 20, 22, 24, 26, 28, 30, 32, 34, 35, 37, 38, 40, 41, 43, 44, 45, 46, 48, 50, 52, 54, 56, 58, 60, 62, 64, 66, 68, 70, 80, 82, 84, 86, 88, 90, 92, 94, 96, and 98 under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding proteins related to TIC6280 or TIC7016, and those sequences, to the extent that they function to express pesticidal proteins either in Bacillus strains or in plant cells, are embodiments of the present invention, recognizing of course that many such redundant coding sequences will not hybridize under these conditions to the native Bacillus sequences encoding TIC6280 or TIC7016. This application contemplates the use of these and other identification methods known to those of ordinary skill in the art, to identify TIC6280 and TIC7016 protein-encoding sequences and sequences having a substantial percentage identity to TIC6280 and TIC7016 protein-encoding sequences.

This disclosure also contemplates the use of molecular methods known in the art to engineer and clone commercially useful proteins comprising chimeras of proteins from pesticidal proteins; e.g., the chimeras may be assembled from segments of a protein from the TIC6280 or TIC7016 protein toxin classes to derive additional useful embodiments including assembly of segments of a protein from the TIC6280 or TIC7016 protein toxin classes with segments of diverse proteins different from proteins from the TIC6280 or TIC7016 protein toxin classes. A protein from the TIC6280 or TIC7016 protein toxin classes may be subjected to alignment to other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity and/or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

This disclosure also contemplates the use of molecular methods known in the art to engineer and clone commercially useful proteins comprising fusions of proteins from pesticidal proteins; e.g., the fusions may be assembled by combining a TIC7016-related toxin protein with a TIC6280-related toxin protein. The fusion protein may increase the spectrum of activity and/or provide for multiple modes of action against an insect pest species. The fusion proteins may be direct fusions wherein the first and second toxin protein coding sequences are operably linked and in frame as one contiguous sequence. Translation of the sequence encoding such a fusion protein produces an amino acid sequence of the fusion toxin protein without any additional amino acids in between the first and second toxin protein. Such exemplary fusion protein coding sequences are provided as SEQ ID NOs:54, 60, and 66 and encode the chimera toxin proteins presented as SEQ ID NOs:55, 61, and 67, respectively. The fusion proteins may also comprise a linker sequence that is operably linked and in frame between the two toxin proteins. A linker may be cleavable, for example by endogenous enzymes present in the insect gut to release the two insect toxins in the fusion protein from one another when ingested by the insect pest species. Such a linker is provided as SEQ ID NO:72 and encodes the amino acid sequence presented as SEQ ID NO:73. Exemplary fusion toxin protein coding sequences that comprise a cleavable linker are provided as SEQ ID NOs:56, 62, and 68 and encode the proteins presented as SEQ ID NOs:57, 63, and 69. A linker within a fusion protein may be a peptide fragment that is flexible and allows for the expression and proper folding of the first and second toxin protein; and provides sufficient spacing for each toxin protein in the fusion protein to bind to their respective receptors. Such a linker is provided as SEQ ID NO:74 and encodes the amino acid sequence presented as SEQ ID NO:75. Exemplary fusion toxin protein coding sequences comprising a flexible linker are provided as SEQ ID NOs:58, 64, and 70 and encode the fusion toxin proteins presented as SEQ ID NOs:59, 65, and 71.

The disclosure also contemplates two or more toxin proteins being encoded by an artificial operon which would permit the co-expression of two or more toxin proteins in a bacterial host cell. A representative sequence which can be used to link the two toxin coding sequences is presented as SEQ ID NO:79, wherein the first 3 nucleotides at the 5' end of the linker encode a stop codon to terminate transcription of the first toxin protein in the operon. Exemplary operon sequences comprising two toxin protein coding sequences are provided as SEQ ID NOs:76, 77, and 78.

Methods of controlling insects, in particular Lepidoptera, or Coleoptera, or Hemiptera, or Thysanoptera infestations of crop plants, with a protein from the TIC6280 or TIC7016 protein toxin classes are also disclosed in this application. Such methods can comprise growing a plant comprising an insect-, Coleoptera-, or Lepidoptera-, or Hemiptera-, or Thysanoptera-inhibitory amount of a protein from the TIC6280 or TIC7016 protein toxin classes. In certain embodiments, such methods can further comprise any one or more of: (i) applying any composition comprising or encoding a protein from the TIC6280 or TIC7016 protein toxin classes to a plant or a seed that gives rise to a plant; and (ii) transforming a plant or a plant cell that gives rise to a plant with a polynucleotide a protein from the TIC6280 or TIC7016 protein toxin classes. In general, it is contemplated that a protein from the TIC6280 or TIC7016 protein toxin classes can be provided in a composition, provided in a microorganism, or provided in a transgenic plant to confer insect inhibitory activity against Lepidopteran, Coleopteran or Hemipteran insects.

In certain embodiments, a recombinant nucleic acid molecule of a protein from the TIC6280 or TIC7016 protein toxin classes is the insecticidally active ingredient of an insect inhibitory composition prepared by culturing recombinant Bacillus or any other recombinant bacterial cell transformed to express a protein from the TIC6280 or TIC7016 protein toxin classes under conditions suitable to express a protein from the TIC6280 or TIC7016 protein toxin classes. Such a composition can be prepared by desiccation, lyophilization, homogenization, extraction, filtration, centrifugation, sedimentation, or concentration of a culture of such recombinant cells expressing/producing said recombinant polypeptide. Such a process can result in a Bacillus or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising a protein from the TIC6280 or TIC7016 protein toxin classes can further comprise at least one additional polypeptide that exhibits insect inhibitory activity against the same Lepidopteran, Coleopteran or Hemipteran insect species, but which is different from the protein from the TIC6280 or TIC7016 protein toxin classes. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Patent Publication No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869 and TIC1100, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-02104162 A1), and ω-Hexatoxin-Hv1a (U.S. Patent Application Publication US 2014-0366227 A1).

Such additional polypeptides for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. Additional polypeptides for the control of Coleopteran, Lepidopteran, Hemipteran and Thysanopteran insect pests can be found on the *Bacillus thuringiensis* toxin nomenclature website maintained by Neil Crickmore (on the world wide web at btnomenclature.info)

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran, or Lepidopteran, or Hemipteran, or Thysanopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC6280 toxin protein or TIC6280-related toxin proteins, or TIC7016 toxin protein, or TIC7016-related toxin proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of Novel *Lysinibacillus sphaericus* and Metagenome Genes

This Example describes the discovery of the pesticidal proteins TIC6280, TIC6281, TIC6282, TIC6283, TIC8808, TIC9480, TIC9257, TIC7106, TIC7017, TIC7107, TIC7108, TIC7109, TIC7110, TIC7111, TIC7589, TIC9258, and TIC9259.

Sequences encoding novel *Lysinibacillus sphaericus* (Ls) pesticidal proteins were identified, cloned, sequence confirmed and tested in insect bioassay. The pesticidal protein TIC6280, presented herein as SEQ ID NO:22 (Ls coding sequence) and SEQ ID NO:23 (protein) was isolated from *Lysinibacillus sphaericus* species AG0067H07. High throughput sequencing and bioinformatics were used to screen Ls genomes and metagenomes derived from plate-scrapes for genes (open reading frames) encoding proteins exhibiting similarity to TIC6280. Six related toxin proteins were identified in this screen and are presented in Table 7, along with the corresponding Ls strain or metagenome designation (MTG) and percent identity to the TIC6280 protein.

TABLE 7

TIC6280 and related toxin proteins.

| Toxin | Coding SEQ ID NO: | Protein SEQ ID NO: | Ls Species | % Identity to TIC6280 |
| --- | --- | --- | --- | --- |
| TIC6280 | 22 | 23 | AG0067H07 | — |
| TIC6281 | 24 | 25 | AG0067H03 | 99.3 |
| TIC6282 | 26 | 27 | AG0069H08 | 99.3 |
| TIC6283 | 28 | 29 | AG0025E04 | 99.3 |
| TIC8808 | 90 | 91 | MTG000070 | 92.7 |
| TIC9480 | 92 | 93 | MTG000415 | 83.2 |
| TIC9257 | 94 | 95 | MTG000199 | 83.2 |

The pesticidal protein TIC7016, presented herein as SEQ ID NO:30 (Ls coding sequence) and SEQ ID NO:31 (protein) was isolated from *Lysinibacillus sphaericus* species EGBS0420. High throughput sequencing and bioinformatics were used to screen Ls genomes and metagenomes derived from plate-scrapes for genes (open reading frames) encoding proteins exhibiting similarity to TIC7016. Nine related toxin proteins were identified in this screen and are present in Table 8, along with the corresponding Ls strain or metagenome designation (MTG) and percent identity to the TIC7016 protein. The coding sequences encoding TIC7107, TIC7109, TIC7110, and TIC7111 encode an identical amino acid sequence, herein referenced as TIC7110 (SEQ ID NO:39). Each of the TIC7110 protein encoding sequences differs from each other by one to six nucleotides and represents variant coding sequences encoding the same protein amino acid sequence, referenced herein as TIC7110.

TABLE 8

TIC7016 and related toxin proteins.

| Toxin | Coding SEQ ID NO: | Protein SEQ ID NO: | Ls Species | % Identity to TIC7016 |
| --- | --- | --- | --- | --- |
| TIC7016 | 30 | 31 | EGBS0420 | — |
| TIC7017 | 32 | 33 | EGBS1094 | 98.9 |
| TIC7107 | 34 | 39 | AG0025E04 | 96.7 |
| TIC7108 | 35 | 36 | AG0067H01 | 96.4 |
| TIC7109 | 37 | 39 | AG0067H03 | 96.7 |
| TIC7110 | 38 | 39 | AG0067H07 | 96.7 |
| TIC7111 | 40 | 39 | AG0069H08 | 96.7 |
| TIC7589 | 41 | 42 | AG0122F12 | 62.8 |
| TIC9258 | 96 | 97 | MTG000120 | 99.3 |
| TIC9259 | 98 | 99 | MTG000184 | 99.6 |

Nucleotide segments encoding the proteins from the TIC6280 or TIC7016 protein toxin classes were made by PCR amplification using genomic DNA from the corresponding strains or chemically synthesized and cloned into plasmid expression vectors for expression in a bacterial host.

Example 2

Bioassay of Proteins Members from the TIC6280 and TIC7016 Protein Toxin Classes Against Insect Pests This Example describes the bioassay of activity against Coleopteran, Lepidopteran, and Hemipteran insect pests using bacterial preparations of proteins from the TIC6280 and TIC7016 protein toxin classes.

Proteins from the TIC6280 and TIC7016 protein toxin classes were expressed in *E. coli* as Histidine-tagged proteins and assayed for toxicity to various species of Lepidoptera, Coleoptera, and Hemiptera. The coding sequences encoding the proteins from the TIC6280 and TIC7016 protein toxin classes were cloned using methods known in the art to comprise a short sequence at the 3' end encoding a Histidine tag used for the purification of each toxin protein. The sequences encoding each His-tagged toxin and the resulting His-tagged protein are presented in Table 9 below.

Preparations of each toxin from *E. coli* were assayed against the Coleopteran species Western Corn Rootworm (WCR, *Diabrotica virgifera virgifera*), Northern Corn Rootworm (NCR, *Diabrotica barberi*), Southern Corn Rootworm (SCR, *Diabrotica undecimpunctata howardii*), and Colorado potato beetle (CPB, *Leptinotarsa decemlineata*); the Hemipteran species Tarnished plant bug (TPB, *Lygus lineolaris*), Western tarnished plant bug (WTP, *Lygus hesperus*), Southern Green Stink Bug (SGSB, *Nezara viridula*), and Neotropical Brown Stink Bug (NBSB, *Euschistus heros*); and the Lepidopteran species Soybean looper (SBL, *Chrysodeixis includens*), European corn borer (ECB, *Ostrinia nubilalis*), Tobacco budworm (TBW, *Heliothis virescens*), Corn earworm (CEW, *Helicoverpa zea*), Fall armyworm (FAW, *Spodoptera frugiperda*), Southern Army Worm (SAW, *Spodoptera eridania*), Southwestern Corn Borer (SWC, *Diatraea grandiosella*), Diamondback Moth (DBM, *Plutella xylostella*), Black Cutworm (BCW, *Agrotis ipsilon*) and Velvetbean Catapillar (VBC, (*Anticarsia gemmatalis*).

TABLE 9

His-tagged coding and protein sequences of the TIC6280 and TIC7016 protein toxin classes and insects assayed.

| Toxin | Coding Sequence SEQ ID NO: | Protein Sequence SEQ ID NO: | Insects Assayed |
|---|---|---|---|
| TIC6280-His | 1 | 2 | WCR; CPB; TBP; WTP; SGSB; NBSB; SBL; ECB; CEW; FAW; ECB; SWC |
| TIC6281-His | 3 | 4 | CPB; TPB; WTP; SGSB; NBSB; SBL; CEW; FAW; SAW; SWC |
| TIC6282-His | 5 | 6 | WCR; CPB; TBP; WTP; SGSB; NBSB; SBL; ECB; CEW; FAW; ECB; SAW; SWC |
| TIC6283-His | 7 | 8 | WCR; CPB; TBP; WTP; SGSB; NBSB; SBL; ECB; CEW; FAW; ECB; SWC |
| TIC8808-His | 80 | 81 | BCW; WTP; SGSB; SAW; SBL; SWC |

TABLE 9-continued

His-tagged coding and protein sequences of the TIC6280 and TIC7016 protein toxin classes and insects assayed.

| Toxin | Coding Sequence SEQ ID NO: | Protein Sequence SEQ ID NO: | Insects Assayed |
|---|---|---|---|
| TIC7016-His | 9 | 10 | WCR; CPB; TPB; WTP; SGSB; NBSB; SBL; ECB; TBW; CEW; FAW; DBM |
| TIC7017-His | 11 | 12 | WCR; NCR; SCR; CPB; TPB; WTP; SGSB; NBSB; SBL; ECB; TBW; CEW; FAW; SWC; NBSB; DBM |
| TIC7107-His | 13 | 18 | CPB; TPB; WTP; SBL; ECB; TBW; CEW; FAW; SWC; VBC |
| TIC7108-His | 14 | 15 | WCR; CPB; SGSB; SWC; DBM |
| TIC7109-His | 16 | 18 | WCR; CPB; TPB; WTP; SGSB; DBM; VBC |
| TIC7110-His | 17 | 18 | WCR; CPB; TPB; WTP; SGSB; NBSB; SBL; ECB; CEW; FAW; TBW; DBM; VBC |
| TIC7111-His | 19 | 18 | WCR; CPB; TPB; WTP; SGSB; NBSB; SBL; ECB; CEW; FAW; TBW; DBM; VBC |
| TIC7589-His | 20 | 21 | CPB; VBC |
| TIC9258-His | 86 | 87 | WTP; BCW; SAW; SBL; SWC |
| TIC9259-His | 88 | 89 | WCR; BCW; SWC |

The pesticidal activity of the proteins from the TIC6280 or TIC7016 protein toxin classes is presented in Tables 10 and 11 wherein "+" indicates activity.

TABLE 10

Pesticidal activity of proteins from the TIC6280 and TIC7016 protein toxin classes against Coleopteran and Hemipteran insect pest species.

| Toxin | WCR | NCR | SCR | CPB | TPB | WTP | SGSB | NBSB |
|---|---|---|---|---|---|---|---|---|
| TIC6280 | + | | | + | | | | |
| TIC6281 | | | | | | | + | |
| TIC6282 | + | | | + | + | | + | |
| TIC6283 | + | | | + | + | | + | |
| TIC8808 | | | | | | | | |
| TIC7016 | + | | | + | + | + | + | + |
| TIC7017 | + | + | + | + | + | + | + | + |
| TIC7107 | | | | + | + | + | | |
| TIC7108 | + | | | + | | | + | |
| TIC7109 | + | | | + | + | + | + | |
| TIC7110 | + | | | + | + | + | + | + |
| TIC7111 | + | | | + | + | + | + | + |
| TIC7589 | | | | + | | | | |
| TIC9258 | | | | | | | | |
| TIC9259 | + | | | | | | | |

TABLE 11

Pesticidal activity of proteins from the TIC6280 and TIC7016 protein toxin classes against Lepidopteran insect pest species.

| Toxin | SBL | ECB | TBW | CEW | FAW | SAW | SWC | DBM | BCW | VBC |
|---|---|---|---|---|---|---|---|---|---|---|
| TIC6280 | | | | | | | | | | |
| TIC6281 | | | | | | | | | | |
| TIC6282 | | | | | | | | | | |
| TIC6283 | | | | | | | | | | |
| TIC8808 | | | | | | | | | | |
| TIC7016 | + | + | | | | | | + | | + |
| TIC7017 | + | | | | | | | + | | + |
| TIC7107 | + | | | + | | | + | | | |
| TIC7108 | | | | | | | + | + | | |
| TIC7109 | | | | | | | | + | | + |
| TIC7110 | + | | | + | | | | + | | + |
| TIC7111 | | | | | | | | + | | + |
| TIC7589 | | | | | | | | | | |
| TIC9258 | | | | | | | | | | |
| TIC9259 | | | | | | | | | | |

As can be seen in Tables 10 and 11, proteins from the TIC6280 and TIC7016 protein toxin classes demonstrated activity against a broad range of pests, some toxins exhibiting activity against insect pests of all three represented families: Coleoptera, Hemiptera, and Lepidoptera. Some variability was observed with respect to activity of proteins derived from the TIC7109, TIC7110, and TIC7111 coding sequences, even though all three sequences encoded the same protein. This variability may be due to differences in the protein preparation resulting from expression in the *E. coli* host, or subsequent purification. In addition, not all preparations were assayed against all insect pests. Therefore, the activity observed for TIC7110 is used as representative of the activity of the toxin protein encoded by all four coding sequences.

Example 3

Design of Synthetic Coding Sequences Encoding Proteins from the TIC6280 and TIC7016 Protein Toxin Classes for Expression in Plant Cells This Example describes the design of synthetic DNA sequences encoding proteins from the TIC6280 and TIC7016 protein toxin classes used for expression of the protein in transformed plant cells.

Synthetic coding sequences are constructed for use in expression of the encoded protein in plants, and can be cloned into binary plant transformation vectors, and used to transform plant cells. The synthetic sequences are synthesized according to methods generally described in U.S. Pat. No. 5,500,365, avoiding certain inimical problem sequences such as ATTTA and A/T rich plant polyadenylation sequences while preserving the amino acid sequence of the original protein. The synthetic coding sequences presented in Table 12 encode plant version proteins of certain proteins from the TIC6280 and TIC7016 protein toxin classes.

TABLE 12

Synthetic coding sequences designed for expression in a plant cell.

| Toxin | Synthetic Coding Sequence SEQ ID NO: | Protein SEQ ID NO: |
|---|---|---|
| TIC6280 | 43 | 23 |
| TIC6282 | 44 | 27 |
| TIC6283 | 45 | 29 |
| TIC7016PL | 46 | 47 |
| TIC7017PL | 48 | 49 |
| TIC7108PL | 50 | 51 |
| TIC7110PL | 52 | 53 |

The synthetic coding sequences were cloned into plant binary transformation vectors using methods known in the art. The resulting binary vectors comprised a first transgene cassette comprising a plant expressible promoter, optionally operably linked 5' to an intron, operably linked 5' to a synthetic coding sequence encoding TIC6280, or TIC6282, TIC6283, TIC7016, TIC7017, TIC7108, or TIC7110 operably linked 5' to a 3' UTR; and a second transgene cassette used for selection of transformed plant cells using glyphosate selection or antibiotic selection using an antibiotic such as spectinomycin.

Example 4

Assay of Activity Against Coleopteran Pests Using Stably Transformed Corn Plants Expressing Proteins from the TIC6280 and TIC7016 Toxin Protein Classes This Example describes the assay of activity against Coleopteran insect pests in corn plants stably transformed to express proteins from the TIC6280 and TIC7016 protein toxin classes.

Binary plant transformation vectors comprising transgene cassettes designed to express proteins from the TIC6280 and TIC7016 protein toxin classes are cloned using methods known in the art. The resulting vectors are used to stably transform corn plants. Pesticidal activity is assayed against Coleopteran pests feeding on the roots of the stably transformed corn plants.

The binary vectors described in Example 3 are used to stably transform corn plants. Single T-DNA insertion events are selected and grown. R$_0$ stably transformed plants are used to assay for Coleopteran resistance as well as generating F$_1$ progeny. Multiple single copy events are selected from each binary vector transformation. A portion of those events arising from each binary vector transformation are used in the Coleopteran assay, while another portion of events are used to generate $F_1$ progeny for further testing.

The $R_0$ assay plants are transplanted to eight inch pots. The plants are inoculated with eggs from Western Corn Rootworm (*Diabrotica virgifera virgifera*, WCR). The eggs are incubated for approximately ten days prior to inoculation to allow hatching to occur four days after inoculation to ensure a sufficient number of larvae survive and are able to attack the corn roots. The transformed plants are inoculated at approximately V2 to V3 stage. The plants are grown after infestation for approximately twenty eight days. The plants are removed from the pots with the roots being carefully washed to remove all soil. The damage to the roots is assessed using a damage rating scale of 1-5, as presented in Table 13. Comparison is also made to a negative control to assure the assay has been performed properly. Low root damage scores indicate resistance conferred by the protein from the TIC6280 and TIC7016 classes to the Coleopteran pest. Multiple $R_0$ events for each binary vector transformation are used in the WCR assay. Those $R_0$ events which demonstrate a lower root damage rating score than the controls are interpreted as to providing resistance against the CRW.

TABLE 13

$R_0$ root damage rating scores.

| Root Damage Score | Description |
| --- | --- |
| 1 | No visible feeding |
| 2 | Some feeding; no pruning |
| 3 | Pruning of at least one root |
| 4 | Entire node pruned |
| 5 | More than one node pruned |

A portion of the $R_0$ stably transformed events arising from each binary vector transformation are used to produce $F_1$ progeny. The $R_0$ stably transformed plants are allowed to self-fertilize, producing $F_1$ progeny. The $F_1$ seed is planted. Heterozygous plants are identified through molecular methods known in the art and used for assay against WCR, as well as ELISA expression measurements of protein from the TIC6280 and TIC7016 protein classes. A portion of the heterozygous $F_1$ progeny from each event is used for insect assay, while another portion is used to measure toxin protein expression.

Eggs from Western Corn Rootworm (*Diabrotica virgifera virgifera*, WCR) are incubated for approximately ten days to allow hatching within four days after inoculation. The plants are inoculated at approximately V2 to V3 stage. For WCR, each pot is inoculated with about two thousand eggs. The plants are grown after infestation for approximately twenty eight days. The plants are removed from the pots with the roots being carefully washed to remove all soil. The damage to the roots is assessed using a damage rating scale of 0-3, as presented in Table 14. Comparison is made to the negative control to assure the assay has been performed properly. Low root damage scores indicated resistance conferred by the protein from the TIC6280 and TIC7016 protein toxin classes to the Coleopteran pest.

TABLE 14

$F_1$ root damage rating scores.

| Root Damage Score | Description |
| --- | --- |
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

Activity against other corn rootworm species can be assayed in a similar manner as that described above for WCR. For example, root damage rating scores can be derived using colonies of *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*). Inoculation amounts, egg hatch conditions, and duration of feeding may vary depending upon the biological characteristics of the specific rootworm species.

Example 5

Assay of Activity Against Lepidopteran Pests Using Stably Transformed Corn, Soybean, or Cotton Plants Expressing Protein from the TIC6280 and TIC7016 Protein Toxin Classes This Example describes the assay of activity against Lepidopteran insect pests in corn, soybean or cotton plants stably transformed to express proteins from the TIC6280 and TIC7016 protein toxin classes.

Binary plant transformation vectors comprising transgene cassettes designed to express proteins from the TIC6280 and TIC7016 protein toxin classes are cloned using methods known in the art. The resulting vectors are used to stably transform corn plants. Pesticidal activity is assayed against Lepidopteran pests feeding on leaf disc tissue derived from the stably transformed corn, soybean, or cotton plants.

The binary vectors described in Example 3 are used to stably transform corn, soybean, or cotton plants. Single T-DNA insertion events are selected and grown. The $R_0$ stably transformed plants are allowed to grow to a selected vegetative stage of growth. Bioassays using plant leaf disks are performed analogous to those described in U.S. Pat. No. 8,344,207. A non-transformed plant is used to obtain tissue to be used as a negative control. Multiple transformation events from each binary vector are assessed against Lepidopteran insect pest species such as, but not limited to, Soybean looper (SBL, Chrysodeixis *includens*), European corn borer (ECB, *Ostrinia nubilalis*), Tobacco budworm (TBW, *Heliothis virescens*), Corn earworm (CEW, *Helicoverpa zea*), Fall armyworm (FAW, *Spodoptera frugiperda*), Southern Army Worm (SAW, *Spodoptera eridania*), Southwestern Corn Borer (SWC, *Diatraea grandiosella*), Diamondback Moth (*Plutella xylostella*), and Velvet Bean Catapillar (*Anticarsia gemmatalis*).

The insect pests are observed for mortality and stunting caused by ingestion of the presented leaf discs expressing the proteins from the TIC6280 and TIC7016 protein toxin classes and compared to leaf discs derived from non-transformed corn, soybean or cotton plants.

Example 6

Assay of the Activity of Proteins from the TIC6280 and TIC7016 Protein Toxin Classes Against Hemipteran Pests in Stably Transformed Soybean Plants This Example describes the assay of activity against Hemipteran insect pests in soybean plants stably transformed to express proteins from the TIC6280 and TIC7016 protein toxin classes.

Soybean plants are transformed using binary plant transformation vectors similar to those as described in Example 3. The transformed soybean plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the developing seeds and pods of the soybean plant. To assay for activity against Stink Bugs, R5 stage pods are harvested from the transgenic soybean plants expressing proteins from the TIC6280 and TIC7016 protein toxin classes and placed in a covered Petri dish or large multi-well plate containing a layer of either agar or wet paper to provide humidity to the feeding environment. Second instar Stink Bug nymphs are placed in the Petri dish or large multi-well plate. A cover providing for the exchange of oxygen while preventing desiccation is placed over the feeding environment. The Stink Bug nymphs are allowed to feed for several days. Measurements of stunting and mortality are taken and compared to Stink Bugs nymphs feeding on pods from untransformed soybean plants.

Alternatively, assay of activity can also be performed on whole stably transformed plants. Transformed plants expressing protein from the TIC6280 and TIC7016 protein toxin classes are grown in a growth chamber or in the greenhouse. At R5 stage, the plants are enclosed in a cage made from breathable plastic "pollination" sheets (Vilutis and Company Inc, Frankfort, IL). The sheet sleeves are secured to the main stem just above the soil surface using a Velcro® tie. Each plant is infested with a specific number of second instar Stink Bug nymphs. The nymphs are released into each individual cage through a small slit on the cage side and then the cage is securely closed ensuring the insects will not escape, and the nymphs are allowed to feed on the soybean pods for several days to a week or more. Observations are taken each day to determine measurements of stunting and mortality. At the end of the feeding period, the live and dead nymphs are collected. The plants are cut below the cages and moved to a laboratory where the insects are collected for each plant. Before opening the cage, the plants are vigorously shaken to ensure all of the insects fall off from their feeding sites to the base of the cage. Then the cage base is opened and all plant material is removed and placed on a black sheet. The insects can be collected using an aspirator or some other means. The number of insects and their developmental stage is recorded for each plant. Also, the number and developmental stage of dead nymphs is also recorded. These measurements are compared to the measurements obtained from negative control, un-transformed plants.

Delays in development of the Stink Bug nymphs (stunting) or mortality are interpreted as an indication of toxicity if, when compared to the un-transformed controls, there is a significant difference.

Example 7

Assay of the Activity of Proteins from the TIC6280 and TIC7016 Toxin Protein Classes Against Hemipteran Pests in Stably Transformed Corn Plants This Example describes the assay of activity against Hemipteran insect pests in corn plants stably transformed to express proteins from the TIC6280 and TIC7016 toxin protein classes.

Corn plants are transformed using binary plant transformation vectors as described in Example 3. The transformed corn plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the young corn plants in late spring or early summer, resulting in holes in the leaf, and if severe, deformed plants. In late summer, Stink Bugs typically feed on the ear itself, directly destroying the kernels.

One method to assay for Stink Bug activity is to expose the Stink Bug nymphs to leaf discs derived from stably transformed corn plants expressing proteins from the TIC6280 and TIC7016 protein toxin classes in large multi-well plates. Second stage instar Stink Bug nymphs are placed in large multi-well plates with leaf discs derived from the stably transformed corn plants and allowed to feed for several days. Measurements of stunting and mortality are taken and compared to Stink Bug nymphs who have fed on un-transformed corn leaf discs.

Alternatively, whole transformed plants can be used to assay for Stink Bug activity. Stably transformed corn plants expressing proteins from the TIC6280 and TIC7016 protein toxin classes are enclosed in cages in a similar manner as described for soybean plants in Example 4. Second instar nymphs are introduced to V3 stage corn plants and allowed to feed for several days to a week. After the prescribed feeding period, the nymphs are collected as described in Example 4. Measurements of stunting and mortality are compared to un-transformed control plants.

To assay Stink Bug activity using stably transformed corn ears, a similar approach can be taken as that of assaying in V3 stage plants. The developing corn ears of stably transformed corn plants expressing proteins from the TIC6280 and TIC7016 protein toxin classes are encapsulated using sheets of material that permit the free exchange of air while preventing escape of the Stink Bug nymphs. The encapsulated ears are infested with second instar stage Stink Bug nymphs and allowed to feed on the developing kernels of the ear for several days to a week. Measurements of stunting and mortality are compared to un-transformed control plant ears.

Example 8

Fusion Proteins and Operons Derived from Proteins from the TIC6280 and TIC7016 Protein Toxin Classes This Example describes the design of synthetic DNA sequences encoding fusion proteins comprising a protein from the TIC7016 protein toxin class fused to a protein from the TIC6280 protein toxin class, as well as operons comprising coding sequences encoding a toxin from the TIC7016 protein toxin class and a toxin from the TIC6280 protein toxin class.

The coding sequences encoding proteins from the TIC6280 and TIC7016 protein toxin classes can be used to make fusion proteins comprising two toxin proteins; a first toxin protein being a protein from the TIC7016 protein toxin class; and a second toxin protein being a protein from the TIC6280 protein toxin class. The fusion protein may increase the spectrum of activity and/or provide for multiple modes of action against an insect pest species. The first and second toxin proteins can be selected from the same bacterial species from which they were initially isolated or, alternatively, the first and second toxin proteins can be selected from different bacterial species from which the respective toxins were first isolated.

Various types of fusions can be made using cloning methods known in the art. Exemplary sequences of three types of fusion proteins (direct fusion, fusion with cleavable linker, and fusion with a flexible linker) are presented in Table 15. The fusion proteins presented in Table 15 demonstrate fusion proteins that are derived from a protein from the TIC7016 protein toxin class fused to a protein from the TIC6280 protein toxin class, which proteins have been isolated from the same Lysinibacillus sphaericus species.

A direct fusion toxin coding sequence comprises two toxin protein coding sequences operably linked, in frame, and contiguous, resulting in a coding sequence encoding a fusion protein in which both toxin proteins are directly fused to make one large toxin protein. Directly fused fusion protein coding sequences are represented by SEQ ID NOs: 54, 60, and 66 and encode the fusion proteins presented as SEQ ID NOs:55, 61, and 67.

A fusion protein comprising a cleavable linker, herein presented as Linker 1 encoded by SEQ ID NO:72 and encoding the linker amino acid sequence presented as SEQ ID NO:73, is operably linked and in frame between the first and second toxin protein coding sequences. When ingested by the insect, enzymes present in the insect gut cleave the linker, thus releasing the two toxin proteins from each other and permitting each to bind to its respective receptor. Fusion proteins comprising a cleavable linker are represented by SEQ ID NOs:56, 62, and 68 and encode the fusion proteins presented as SEQ ID NOs:57, 63, and 69.

A fusion protein comprising a flexible linker, herein presented as Linker 2 encoded by SEQ ID NO:74 and encoding the linker amino acid sequence presented as SEQ ID NO:75, is operably linked and in frame between the first and second toxin protein coding sequences. The flexible linker allows for proper folding of each respective toxin protein in the fusion and provides a flexible amino acid region that permits each toxin protein to bind to its respective receptor. Fusion proteins comprising a flexible linker are represented by SEQ ID NOs:58, 64, and 70 and encode the fusion proteins presented as SEQ ID NOs:59, 65, and 71.

Fusion proteins can also be synthesized from any protein from the TIC7016 protein toxin class and any protein from the TIC6280 protein toxin class to increase the spectrum of activity and provide additional modes of activity against an insect pest. Table 16 shows a collection of potential fusion proteins that can be derived using a coding sequence encoding TIC7016, TIC7017, TIC7108, TIC7110, or TIC7589 fused to a coding sequence encoding TIC6280, TIC6281, TIC6282, or TIC6283.

TABLE 15

Fusion toxin protein encoding and protein sequences.

| Fusion Protein Sequence | Type of Fusion | Coding Sequence SEQ ID NO: | Protein SEQ ID NO: | First Protein | Linker | Second Protein | Ls Species |
|---|---|---|---|---|---|---|---|
| TIC7110-TIC6280F1 | Direct | 54 | 55 | TIC7110 | None | TIC6280 | AG0067H07 |
| TIC7110-TIC6280F2 | Cleavable Linker | 56 | 57 | TIC7110 | Linker 1 | TIC6280 | AG0067H07 |
| TIC7110-TIC6280F3 | Flexible Linker | 58 | 59 | TIC7110 | Linker 2 | TIC6280 | AG0067H07 |
| TIC7111-TIC6282F1 | Direct | 60 | 61 | TIC7111 | None | TIC6282 | AG0069H08 |
| TIC7111-TIC6282F2 | Cleavable Linker | 62 | 63 | TIC7111 | Linker 1 | TIC6282 | AG0069H08 |
| TIC7111-TIC6282F3 | Flexible Linker | 64 | 65 | TIC7111 | Linker 2 | TIC6282 | AG0069H08 |
| TIC7109-TIC6281F1 | Direct | 66 | 67 | TIC7109 | None | TIC6281 | AG0067H03 |
| TIC7109-TIC6281F2 | Cleavable Linker | 68 | 69 | TIC7109 | Linker 1 | TIC6281 | AG0067H03 |
| TIC7109-TIC6281F3 | Flexible Linker | 70 | 71 | TIC7109 | Linker 2 | TIC6281 | AG0067H03 |

TABLE 16

Potential fusion toxin proteins derived from proteins from the TIC6280 and TIC7016 protein toxin classes

| Fusion Protein | First Protein | Linker | Second Protein | Fusion Protein | First Protein | Linker | Second Protein |
|---|---|---|---|---|---|---|---|
| TIC7016-TIC6280F1 | TIC7016 | None | TIC6280 | TIC7108-TIC6282F1 | TIC7108 | None | TIC6282 |
| TIC7016-TIC6280F2 | TIC7016 | Linker 1 | TIC6280 | TIC7108-TIC6282F2 | TIC7108 | Linker 1 | TIC6282 |
| TIC7016-TIC6280F3 | TIC7016 | Linker 2 | TIC6280 | TIC7108-TIC6282F3 | TIC7108 | Linker 2 | TIC6282 |
| TIC7016-TIC6281F1 | TIC7016 | None | TIC6281 | TIC7108-TIC6283F1 | TIC7108 | None | TIC6283 |
| TIC7016-TIC6281F2 | TIC7016 | Linker 1 | TIC6281 | TIC7108-TIC6283F2 | TIC7108 | Linker 1 | TIC6283 |
| TIC7016-TIC6281F3 | TIC7016 | Linker 2 | TIC6281 | TIC7108-TIC6283F3 | TIC7108 | Linker 2 | TIC6283 |
| TIC7016-TIC6282F1 | TIC7016 | None | TIC6282 | TIC7110-TIC6280F1 | TIC7110 | None | TIC6280 |
| TIC7016-TIC6282F2 | TIC7016 | Linker 1 | TIC6282 | TIC7110-TIC6280F2 | TIC7110 | Linker 1 | TIC6280 |
| TIC7016-TIC6282F3 | TIC7016 | Linker 2 | TIC6282 | TIC7110-TIC6280F3 | TIC7110 | Linker 2 | TIC6280 |
| TIC7016-TIC6283F1 | TIC7016 | None | TIC6283 | TIC7110-TIC6281F1 | TIC7110 | None | TIC6281 |
| TIC7016-TIC6283F2 | TIC7016 | Linker 1 | TIC6283 | TIC7110-TIC6281F2 | TIC7110 | Linker 1 | TIC6281 |
| TIC7016-TIC6283F3 | TIC7016 | Linker 2 | TIC6283 | TIC7110-TIC6281F3 | TIC7110 | Linker 2 | TIC6281 |
| TIC7017-TIC6280F1 | TIC7017 | None | TIC6280 | TIC7110-TIC6282F1 | TIC7110 | None | TIC6282 |
| TIC7017-TIC6280F2 | TIC7017 | Linker 1 | TIC6280 | TIC7110-TIC6282F2 | TIC7110 | Linker 1 | TIC6282 |
| TIC7017-TIC6280F3 | TIC7017 | Linker 2 | TIC6280 | TIC7110-TIC6282F3 | TIC7110 | Linker 2 | TIC6282 |
| TIC7017-TIC6281F1 | TIC7017 | None | TIC6281 | TIC7110-TIC6283F1 | TIC7110 | None | TIC6283 |
| TIC7017-TIC6281F2 | TIC7017 | Linker 1 | TIC6281 | TIC7110-TIC6283F2 | TIC7110 | Linker 1 | TIC6283 |
| TIC7017-TIC6281F3 | TIC7017 | Linker 2 | TIC6281 | TIC7110-TIC6283F3 | TIC7110 | Linker 2 | TIC6283 |
| TIC7017-TIC6282F1 | TIC7017 | None | TIC6282 | TIC7589-TIC6280F1 | TIC7589 | None | TIC6280 |
| TIC7017-TIC6282F2 | TIC7017 | Linker 1 | TIC6282 | TIC7589-TIC6280F2 | TIC7589 | Linker 1 | TIC6280 |
| TIC7017-TIC6282F3 | TIC7017 | Linker 2 | TIC6282 | TIC7589-TIC6280F3 | TIC7589 | Linker 2 | TIC6280 |
| TIC7017-TIC6283F1 | TIC7017 | None | TIC6283 | TIC7589-TIC6281F1 | TIC7589 | None | TIC6281 |
| TIC7017-TIC6283F2 | TIC7017 | Linker 1 | TIC6283 | TIC7589-TIC6281F2 | TIC7589 | Linker 1 | TIC6281 |
| TIC7017-TIC6283F3 | TIC7017 | Linker 2 | TIC6283 | TIC7589-TIC6281F3 | TIC7589 | Linker 2 | TIC6281 |
| TIC7108-TIC6280F1 | TIC7108 | None | TIC6280 | TIC7589-TIC6282F1 | TIC7589 | None | TIC6282 |
| TIC7108-TIC6280F2 | TIC7108 | Linker 1 | TIC6280 | TIC7589-TIC6282F2 | TIC7589 | Linker 1 | TIC6282 |
| TIC7108-TIC6280F3 | TIC7108 | Linker 2 | TIC6280 | TIC7589-TIC6282F3 | TIC7589 | Linker 2 | TIC6282 |
| TIC7108-TIC6281F1 | TIC7108 | None | TIC6281 | TIC7589-TIC6283F1 | TIC7589 | None | TIC6283 |
| TIC7108-TIC6281F2 | TIC7108 | Linker 1 | TIC6281 | TIC7589-TIC6283F2 | TIC7589 | Linker 1 | TIC6283 |
| TIC7108-TIC6281F3 | TIC7108 | Linker 2 | TIC6281 | TIC7589-TIC6283F3 | TIC7589 | Linker 2 | TIC6283 |

Coding sequences encoding proteins from the TIC6280 and TIC7016 protein toxin classes can be used to make artificial operons used for bacterial expression comprising two toxin proteins; a first toxin protein being selected from the TIC7016 toxin protein class; and a second toxin protein being selected from the TIC6280 toxin protein class. The first and second toxin proteins can be selected from the same bacterial species from which they were initially isolated or, alternatively, the first and second toxin proteins can be selected from different bacterial species from which the respective toxins were first isolated. The two coding sequences would be linked using a linker, for example, the Operon_Linker presented as SEQ ID NO:79. Operon_Linker comprises a stop codon at the 5' end of the sequence to allow for termination of transcription of the first toxin protein coding sequence. Examples of operons derived from proteins from the TIC7016 and TIC680 protein toxin classes isolated from the same Lysinibacillus sphaericus species are presented in Table 17.

TABLE 17

Representative operon sequences.

| Operon Sequence | Nucleotide SEQ ID NO: | First Protein | Linker | Second Protein | Ls Species |
|---|---|---|---|---|---|
| TIC7110-TIC6280operon | 76 | TIC7110 | Operon_Linker | TIC6280 | AG0067H07 |
| TIC7111-TIC6282operon | 77 | TIC7111 | Operon_Linker | TIC6282 | AG0069H08 |
| TIC7109-TIC6281operon | 78 | TIC7110 | Operon_Linker | TIC6280 | AG0067H03 |

Artificial operon sequences can also be derived from toxin protein coding sequences derived from any protein from the TIC6280 and TIC7016 protein toxin classes. Table 18 shows a collection of potential artificial operons that can be derived using a coding sequence encoding TIC7016, or TIC7016, or TIC7108, or TIC7110, or TIC7589 fused to a coding sequence encoding TIC6280, or TIC6281, or TIC6282, or TIC6283.

TABLE 18

Potential operon sequences derived from a protein from the TIC7016 toxin protein class and a protein from the TIC6280 protein toxin class.

| Operon Sequence | First Protein | Linker | Second Protein |
|---|---|---|---|
| TIC7016-TIC6280operon | TIC7016 | Operon_Linker | TIC6280 |
| TIC7016-TIC6281operon | TIC7016 | Operon_Linker | TIC6281 |
| TIC7016-TIC6282operon | TIC7016 | Operon_Linker | TIC6282 |
| TIC7016-TIC6283operon | TIC7016 | Operon_Linker | TIC6283 |
| TIC7017-TIC6280operon | TIC7017 | Operon_Linker | TIC6280 |
| TIC7017-TIC6281operon | TIC7017 | Operon_Linker | TIC6281 |
| TIC7017-TIC6282operon | TIC7017 | Operon_Linker | TIC6282 |
| TIC7017-TIC6283operon | TIC7017 | Operon_Linker | TIC6283 |
| TIC7108-TIC6280operon | TIC7108 | Operon_Linker | TIC6280 |
| TIC7108-TIC6281operon | TIC7108 | Operon_Linker | TIC6281 |
| TIC7108-TIC6282operon | TIC7108 | Operon_Linker | TIC6282 |
| TIC7108-TIC6283operon | TIC7108 | Operon_Linker | TIC6283 |
| TIC7110-TIC6281operon | TIC7110 | Operon_Linker | TIC6281 |
| TIC7110-TIC6282operon | TIC7110 | Operon_Linker | TIC6282 |
| TIC7110-TIC6283operon | TIC7110 | Operon_Linker | TIC6283 |
| TIC7589-TIC6280operon | TIC7589 | Operon_Linker | TIC6280 |
| TIC7589-TIC6281operon | TIC7589 | Operon_Linker | TIC6281 |
| TIC7589-TIC6282operon | TIC7589 | Operon_Linker | TIC6282 |
| TIC7589-TIC6283operon | TIC7589 | Operon_Linker | TIC6283 |

Example 9

TIC7016 is Active Against Thrips

This Example describes the bioassay of activity of TIC7016 against Thysanopteran insect pests using bacterial preparations of TIC7016 protein.

Histidine tagged protein preparations of TIC7016 protein, TIC7016-His (SEQ ID NO:10), were provided in an insect diet and used to assay activity of TIC7016 against the Thysanopteran pest species Western Flower Thrips (*Frankliniella occidentalis*) and Tobacco Thrips (*Frankliniella fusca*). Sixteen Western Flower Thrips and twenty one Tobacco Thrips were allowed to feed on the insect diet for ten days. The numbers of living Thrips were recorded at the first, fifth, seventh, and tenth day after infestation and compared to controls wherein the Thrips fed on an identical diet without toxin. The observed percent mortality is presented in Table 19.

TABLE 19

Percent Thrips mortality over ten days fed on diet containing TIC7016-His.

| | Western Flower Thrips | | Tobacco Thrips | |
|---|---|---|---|---|
| Day | Buffer | TIC7016-His | Buffer | TIC7016-His |
| 1 | 9.50% | 4.76% | 0.00% | 12.50% |
| 5 | 19.04% | 23.81% | 4.76% | 43.75% |
| 7 | 28.57% | 57.14% | 19.05% | 50.00% |
| 10 | 38.10% | 85.71% | 33.33% | 75.00% |

As can be seen in Table 19, with respect to Western Flower Thrips, activity was apparent by the seventh and tenth day of feeding. For Tobacco Thrips, activity was apparent at the fifth, seventh, and tenth day of feeding. The insect toxin, TIC7016 is active against Thysanopteran insect pests.

Example 10

TIC7016PL is Active Against Tarnished Plant Bug (*Lygus lineolaris*) in Stably Transformed Cotton Plants This Example describes the bioassay of activity of TIC7016PL against the Hemipteran insect pest, Tarnished plant bug (TPB, *Lygus lineolaris*) using whole transformed cotton plants expressing TIC7016PL protein.

Cotton plants were transformed with two different binary plant transformation vectors (Construct 1 and Construct 2) used for expression of the TIC7016PL protein. Cotton $R_1$ transformed events were used for assay of activity against the Hemipteran insect pest, Tarnished plant bug (TPB, *Lygus lineolaris*). The binary transformation vectors comprised a first transgene cassette used for expression of the TIC7016PL toxin protein plant expressable promoter, operably linked 5' to a leader, operably linked 5' to an intron, operably linked 5' to a synthetic coding sequence used for expression of TIC7016PL protein in plant cells (SEQ ID NO:46), operably linked 5' to a 3' UTR; and a second transgene cassette used for selection of transformed plant cells using spectinomycin selection.

To assay for efficacy against Tarnished plant bug (TPB, *Lygus lineolaris*), five $R_1$ seeds were sown in 10 inch pots for each of the transgenic cotton events. An untransformed DP393 cotton variety was used as a negative control. Plants were maintained in an environment chamber with a photoperiod of sixteen (16) hours of light at thirty two (32) degrees Celsius and eight (8) hours of dark at twenty three (23) degrees Celsius, and a light intensity between eight hundred (800) and nine hundred (900) micro-Einsteins. At forty (40) to forty five (45) days after planting, the individual plants were enclosed in a cage made from breathable plastic "pollination" sheets (Vilutis and Company Inc, Frankfort, IL). The sheet sleeves were secured to the main stem just above the soil surface using a Velcro® tie. Two pairs of sexually mature male and female *Lygus lineolaris* adults (six days old) from a laboratory culture were collected into a fourteen milliliter round-bottom plastic tube (Becton Dickinson Labware, Franklin Lakes, NJ) and used for each plant. The adults were released into each individual cage through a small slit on the cage side and then the cage was securely closed ensuring the insects would not escape. The insects were allowed to mate and the plants were kept in the cage for twenty one (21) days.

At twenty two (22) days, the plants were then cut below the cages and moved to a laboratory where the insects were collected for each plant and counted. Before opening the cage, the plants were vigorously shaken to ensure all of the insects fell off from their feeding sites to the base of the cage. Then the cage base was opened and all plant material removed and placed on a black sheet. The insects were collected using an aspirator. The plant was then thoroughly inspected to recover any remaining insects. The number of insects collected and their developmental stage were recorded for each plant. The insect counts were divided into several groups based upon the size and maturity of the *Lygus*: small nymphs, large nymphs, and adults. Table 20 and FIG. 1 shows the results of the assay. In FIG. 1 the error bars represent the standard error of the mean (also presented as "SEM" in Table 20).

TABLE 20

Average number of *Lygus lineolaris* (Tarnished plant bug) recovered from caged transformed cotton plants expressing TIC7016PL.

| Construct | Event | Number of Plants | Small nymph Mean | Large Nymph Mean | $R_1$ Adult Mean | Total $R_1$ Mean | SEM |
|---|---|---|---|---|---|---|---|
| Construct 1 | Event 1 | 5 | 1.6 | 2 | 4.4 | 8 | 2.3022 |
|  | Event 2 | 5 | 5.2 | 4.2 | 1.4 | 10.8 | 3.3377 |
| Construct 2 | Event 3 | 5 | 2.6 | 3.2 | 0.8 | 6.6 | 2.358 |
| None | Negative Control | 10 | 11.3 | 8.9 | 5.1 | 25.3 | 2.9061 |

As can be seen in Table 20 and FIG. 1, expression of TIC7016PL in stably transformed cotton plants provides resistance to Tarnished plant bug (TPB, *Lygus lineolaris*). Fewer TPB nymphs and adults survived on the cotton plants expressing TIC7016PL than the controls.

Assay against Western tarnished plant bug (WTP, *Lygus hesperus*) can also be performed against stably transformed cotton plants expressing TIC7016PL protein as described above.

Example 11

TIC7108PL, TIC7110PL, TIC7016PL, and TIC7017PL are Active Against Western Corn Rootworm in Stably Transformed Corn Plants This Example describes the bioassay of activity of TIC7017PL against the Coleopteran insect pest, Western Corn Rootworm (WCR, *Diabrotica virgifera virgifera*) in root feeding assays against TIC7108PL, TIC7110PL, TIC7016PL, and TIC7017PL expressing corn roots.

Corn plants were transformed with binary plant transformation vectors used for the expression of TIC7108PL (Construct 3), TIC7110PL (Construct 4), TIC7016PL (Construct 5), and TIC7017PL (Constructs 6 through 11). The binary plant transformation vectors comprised a first transgene cassette for the expression of TIC7108PL, TIC7110PL, TIC7016PL, or TIC7017PL toxin protein which comprised a plant expressable promoter, operably linked 5' to a leader sequence, operably linked 5' to an intron, operably linked 5' to a synthetic coding sequence encoding TIC7108PL (SEQ ID NO:50), TIC7110PL (SEQ ID NO:52), TIC7016PL (SEQ ID NO:46), or TIC7017PL (SEQ ID NO:48), operably linked 5' to a 3' UTR; and a second transgene cassette for the selection of transformed plant cells using glyphosate selection.

Corn plant cells were transformed with the binary transformation vector described above and induced to form whole $R_0$ transformed plant events. Single and double copy $R_0$ transformed events were selected for the CRW assay. The $R_0$ root feeding assay was that as described in Example 4 above, wherein root damage ratings were assessed using a rating scale of 1-5 as presented in Table 13 of Example 4. Non-transformed corn plants were used as a negative control. Table 21 shows the average root damage rating for each binary transformation vector construct and the control. With respect to the $R_0$ root damage ratings, a score of 1 to 3.5 indicates activity; whereas a score of 3.6 to 5 indicates low activity or no activity.

TABLE 21

Root damage rating score for $R_0$ transformed events expressing TIC7108PL, TIC7110PL, TIC7016PL, and TIC7017PL.

| Construct | Toxin | RDR |
|---|---|---|
| Construct 3 | TIC7108PL | 3.4 |
| Construct 4 | TIC7110PL | 3.5 |
| Construct 5 | TIC7016PL | 3.3 |
| Construct 6 | TIC7017PL | 2.6 |
| Construct 7 | TIC7017PL | 3.4 |
| Construct 8 | TIC7017PL | 3.4 |
| Construct 9 | TIC7017PL | 3.3 |
| Construct 10 | TIC7017PL | 3.4 |
| Construct 11 | TIC7017PL | 3.4 |
| Negative Control |  | 3.8 |

As can be seen in Table 21, stably transformed corn plants expressing TIC7108PL, TIC7110PL, TIC7016PL, and TIC7017PL demonstrated activity against Western Corn Rootworm (*Diabrotica virgifera virgifera*).

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide encoding a pesticidal protein, wherein:
   a. said pesticidal protein comprises an amino acid sequence selected from the group consisting of: SEQ ID NOs:39 and 53;
   b. said pesticidal protein comprises an amino acid sequence having at least 95 % amino acid sequence identity to an amino acid sequence selected from the group consisting of: SEQ ID NOs:39 and 53; or
   c. said polynucleotide comprises a nucleotide sequence selected from the group consisting of: SEQ ID NOs:38 and 52.

2. The recombinant nucleic acid molecule of claim 1, wherein said recombinant nucleic acid molecule:
   a. comprises a sequence that functions to express the pesticidal protein in a plant;
   b. is expressed in a plant cell to produce a pesticidally effective amount of the pesticidal protein; or
   c. is in operable linkage to a vector, and said vector is selected from the group consisting of a plasmid, phagemid, bacmid, cosmid, and a bacterial or yeast artificial chromosome.

3. The recombinant nucleic acid molecule of claim 1, further characterized in that said recombinant nucleic acid molecule is present within a host cell, wherein said host cell is selected from the group consisting of a bacterial and a plant cell.

4. The recombinant nucleic acid molecule of claim 3, wherein the bacterial host cell is from a genus of bacteria selected from the group consisting of *Agrobacterium*, *Rhizobium*, *Bacillus*, *Brevibacillus*, *Escherichia*, *Pseudomonas*, *Klebsiella*, and *Erwinia*;
   and wherein said *Bacillus* species is a *Bacillus cereus* or a *Bacillus thuringiensis*, said *Brevibacillus* is a *Brevibacillus laterosperous*, and said *Escherichia* is an *Escherichia coli*.

5. The recombinant nucleic acid molecule of claim 3, wherein said plant cell is a dicotyledonous or a monocotyledonous plant cell.

6. The recombinant nucleic acid molecule of claim 5, wherein said plant host cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

7. The recombinant nucleic acid molecule of claim 1, wherein said pesticidal protein exhibits activity against an insect species of the order of Coleoptera.

8. The recombinant nucleic acid molecule of claim 7, wherein said insect species is Western Corn Rootworm or Colorado Potato Beetle.

9. The recombinant nucleic acid molecule of claim 1, wherein said pesticidal protein exhibits activity against an insect species of the order of Lepidoptera.

10. The recombinant nucleic acid molecule of claim 9, wherein said insect species is Velvet bean caterpillar, Tobacco budworm, Soybean looper, or Diamondback Moth.

11. The recombinant nucleic acid molecule of claim 1, wherein said pesticidal protein exhibits activity against an insect species of the order of Hemiptera.

12. The recombinant nucleic acid molecule of claim 11, wherein said insect species is Southern Green Stinkbug, Neotropical Brown Stinkbug, Western Tarnished Plant Bug, and Tarnished Plant Bug.

13. A plant comprising a recombinant nucleic acid molecule comprising a heterologous promoter operably linked to a polynucleotide encoding a pesticidal protein, wherein:
   a. said pesticidal protein comprises an amino acid sequence selected from the group consisting of: SEQ ID NOs:39 and 53;
   b. said pesticidal protein comprises an amino acid sequence having at least 95 % or about 100% amino acid sequence identity to an amino acid sequence selected from the group consisting of: SEQ ID NOs:39 and 53;
   c. said polynucleotide comprises a nucleotide sequence selected from the group consisting of: SEQ ID NOs:38 and 52; or
   d. said plant exhibits a detectable amount of said pesticidal protein, wherein the pesticidal protein comprises an amino acid sequence selected from the group consisting of: SEQ ID NOs:39 and 53.

14. The plant of claim 13, wherein said plant is a monocot plant or a dicot plant.

15. The plant of claim 13, wherein the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

16. A seed from the plant of claim 13, wherein said seed comprises said recombinant nucleic acid molecule.

17. An insect inhibitory composition comprising the recombinant nucleic acid molecule of claim 1.

18. The insect inhibitory composition of claim 17, further comprising a nucleotide sequence encoding at least one other pesticidal agent that is different from said pesticidal protein.

19. The insect inhibitory composition of claim 18, wherein said at least one other pesticidal agent is selected from the group consisting of an insect inhibitory protein, an insect inhibitory dsRNA molecule, and an ancillary protein.

20. The insect inhibitory composition of claim 18, wherein said at least one other pesticidal agent exhibits activity against one or more pest species of the orders Lepidoptera, Coleoptera, or Hemiptera.

21. The insect inhibitory composition of claim 20, wherein said at least one other pesticidal agent is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-R1 and variants thereof, IP3 and variants thereof, DIG-3, DIG-5, DIG-10 and a DIG-1.

22. A commodity product that comprises the recombinant nucleic acid molecule of claim 1.

23. The commodity product of claim 22, wherein the commodity product is selected from the group consisting of commodity corn bagged by a grain handler, corn flakes, corn cakes, corn flour, corn meal, corn syrup, corn oil, corn silage, corn starch, corn cereal, whole or processed cotton seed, cotton oil, lint, seeds and plant parts processed for feed or food, fiber, paper, biomasses, and fuel products, fuel derived from cotton oil, pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

24. A method of producing seed comprising:
  a. planting at least one seed from the plant of claim 15;
  b. growing at least one plant from said seed; and
  c. harvesting seed from said plant, wherein said harvested seed comprises the recombinant nucleic acid molecule.

25. A transgenic plant resistant to insect infestation, wherein the cells of said transgenic plant comprise:
  a. a recombinant nucleic acid molecule encoding an insecticidally effective amount of a pesticidal protein, wherein the pesticidal protein comprises an amino acid sequence selected from the group consisting of: SEQ ID NOs:39 and 53; or
  b. an insecticidally effective amount of a pesticidal protein comprising an amino acid sequence having at least 95 % or about 100% amino acid sequence identity to an amino acid sequence selected from the group consisting of: SEQ ID NOs:39 and 53.

26. A method for controlling a Coleopteran, a Lepidopteran, or a Hemipteran species pest or controlling a Coleopteran a Lepidopteran, or a Hemipteran species infestation of a plant, said method comprising contacting the pest with the recombinant nucleic acid molecule of claim 1 and the pesticidal protein encoded by the recombinant nucleic acid molecule.

* * * * *